US012590131B2

(12) United States Patent
Yount et al.

(10) Patent No.: US 12,590,131 B2
(45) Date of Patent: Mar. 31, 2026

(54) ANTIMICROBIAL PEPTIDES WITH ALPHA-CORE HELICES

(71) Applicant: THE LUNDQUIST INSTITUTE FOR BIOMEDICAL INNOVATION AT HARBOR-UCLA MEDICAL CENTER, Torrance, CA (US)

(72) Inventors: Nannette Y. Yount, San Juan Capistrano, CA (US); Michael R. Yeaman, Redondo Beach, CA (US)

(73) Assignee: Lundquist Institute for Biomedical Innovation at Harbor-UCLA Medical Center, Torrance, CA (US)

( * ) Notice: Subject to any disclaimer, the term of this patent is extended or adjusted under 35 U.S.C. 154(b) by 0 days.

(21) Appl. No.: 18/636,117

(22) Filed: Apr. 15, 2024

(65) Prior Publication Data

US 2024/0279292 A1     Aug. 22, 2024

Related U.S. Application Data

(60) Continuation of application No. 18/053,981, filed on Nov. 9, 2022, now Pat. No. 11,987,607, which is a division of application No. 16/612,242, filed as application No. PCT/US2018/032133 on May 10, 2018, now abandoned.

(60) Provisional application No. 62/505,013, filed on May 11, 2017.

(51) Int. Cl.

| | |
|---|---|
| *A61K 38/17* | (2006.01) |
| *C07K 14/435* | (2006.01) |
| *C07K 14/46* | (2006.01) |
| *C07K 14/465* | (2006.01) |
| *C07K 14/47* | (2006.01) |
| *G16B 15/20* | (2019.01) |

(52) U.S. Cl.
CPC .... C07K 14/4723 (2013.01); C07K 14/43518 (2013.01); C07K 14/43522 (2013.01); C07K 14/43568 (2013.01); C07K 14/43572 (2013.01); C07K 14/43581 (2013.01); C07K 14/463 (2013.01); C07K 14/465 (2013.01); G16B 15/20 (2019.02)

(58) Field of Classification Search
None
See application file for complete search history.

(56) References Cited

U.S. PATENT DOCUMENTS

| | | |
|---|---|---|
| 5,607,914 A | 3/1997 | Rao et al. |
| 7,739,055 B2 | 6/2010 | Stephanopoulos et al. |
| 7,807,876 B1 | 10/2010 | Navarro et al. |
| 9,133,257 B2 | 9/2015 | Yeaman et al. |

| | | |
|---|---|---|
| 2010/0076173 A1 | 3/2010 | Stephanopoulos et al. |
| 2015/0232521 A1 | 8/2015 | Yeaman et al. |
| 2017/0121384 A1 | 5/2017 | Yount et al. |

FOREIGN PATENT DOCUMENTS

| | | |
|---|---|---|
| KR | 20030061718 | 7/2003 |
| WO | WO 2016197049 | 12/2016 |
| WO | WO 2017048092 | 3/2017 |

OTHER PUBLICATIONS

Saumya, Donna et al, "Acute septicemia caused by *Stretococcus gallolyticus* subsp. pasteurianus in turkey poults." Avian Dis. (2014) 58 p318-322.*
Linch, Stefanie N. et al, "Interleukin 5 is protective during sepsis in an eosinophil independent manner." Am. J. Respir. Crit. Care Med. (2012) 186(3) p. 246-254.*
Uniprot database entry GINOU6, downloaded Apr. 3, 2025.*
Novelli, Andrea et al, "Pharmacokinetic evaluation of meropenem and imipenem in critically ill patients with sepsis." Clin. Pharmacokinet. (2006) 44(5) p. 539-549.*
Takatsu, Kiyoshi, "Interleukin-5 and il-5 receptor in health and disease." Proc. Jpn. Acad. Ser. B (2011) 87(8) p. 463-485.*
Lowe, Derek, "Not alphafold's fault." blog "In the pipeline" entry of Sep. 7, 2022.*
Guo, Haiwei H. et al, "Protein tolerance to random amino acid change." PNAS (2004) 101(25) p. 9205-9210.*
Yampolsky, Lev Y. et al, "THe exchangeability of amino acids in proteins." Genetics (2006) 170 p. 1459-1472.*
Database UniProt [online] Accession No. G1 N9U6, "RecName: Full=Interleukin-5 {ECO:0000256: RuleBase: RU363136}; AltName: Full=Eosinophil differentiation factor {ECO:0000256: RuleBase:RU363136}," Oct. 19, 2011.
Database Geneseq [online] Accession No. AAP60411, "Exon 4 of human interferon-gamma," Mar. 25, 2003.
Database UniProt [online] Accession No. W2G110, "SubName: Full=Uncharacterized protein {ECO:0000313: Embl: ETK76743. 1}," Mar. 19, 2014.
Database UniProt [online] Accession No. W2Y3P7, "SubName: Full=Uncharacterized protein {ECO:0000313: EMBL: ETP29352. 1}," Mar. 19, 2014.
Database Geneseq [online] Accession No. AAM05438, "Peptide #4120 encoded by probe for measuring breast gene Expression," Oct. 9, 2001.
Database UniProt [online] Accession No. W2Z9T6, "SubName: Full=Uncharacterized protein ECO:0000313IEMBL:ETP42979. 1}," Mar. 19, 2014.
Database UniProt [online] Accession No. A0A081A496, "SubName: Full=Uncharacterized protein ECO:0000313IEMBL:ETO73707. 1}," Oct. 29, 2014.
Bairoch et al., "The SWISS-PROT protein sequence database and its supplement TrEMBL in 2000", Nucleic Acids Res, Jan. 1, 2000, vol. 28, No. 1, pp. 45-48.
International Search Report and Written Opinion for PCT/US2018/032133 dated Oct. 18, 2018, 15 pages.

* cited by examiner

*Primary Examiner* — Fred H Reynolds

(74) *Attorney, Agent, or Firm* — Sheppard Mullin Richter & Hampton LLP

(57) ABSTRACT

Computational systems and methods are described for identifying new α-helical antimicrobial peptides using a systemic consensus formula. Newly identified α-helical antimicrobial peptides are tested experimentally and show potent microbiocidal activities.

8 Claims, 14 Drawing Sheets

Specification includes a Sequence Listing.

| Type | Position | Residues (top → bottom) |
|---|---|---|
| X | 1 | (blank) |
| POL | 2 | K, R, H, E, D, N, Q, S, T, A, G |
| HYD | 3 | F, W, Y, V, I, L, M, C, A, G |
| HYD | 4 | F, W, V, I, L, M, C, A, G |
| POL | 5 | K, R, H, E, D, N, Q, S, T, A, G |
| POL | 6 | K, R, H, E, D, N, Q, S, T, A, G |
| HYD | 7 | F, W, V, I, L, M, C, A, G |
| HYD | 8 | F, W, Y, V, I, L, M, C, A, G |
| POL | 9 | K, R, H, E, D, N, Q, S, T, A, G |
| X | 10 | (blank) |
| HYD | 11 | F, W, Y, V, I, L, M, C, A, G |
| POL | 12 | K, R, H, E, D, N, Q, S, T, A, G |
| POL | 13 | K, R, H, E, D, N, Q, S, T, A, G |
| HYD | 14 | F, W, Y, V, I, L, M, C, A, G |
| HYD | 15 | F, W, Y, V, I, L, M, C, A, G |
| POL | 16 | K, R, H, E, D, N, Q, S, T, A, G |
| POL | 17 | K, R, H, E, D, N, Q, S, T, A, G |
| HYD | 18 | F, W, Y, V, I, L, M, G, A, G |

FIG. 1B

| P | P | H | X | P | H | H | P |
|---|---|---|---|---|---|---|---|
| 4 | 5 | 6 | 7 | 8 | 9 | 10 | 11 |
| K | K | | | K | X | | K |
| R | R | F | F | R | | F | R |
| H | H | W | W | H | | W | H |
| E | E | Y | Y | E | | Y | E |
| D | D | V | V | D | | V | D |
| N | N | N | N | N | | N | N |
| Q | Q | L | L | Q | | L | Q |
| S | S | M | M | S | | M | S |
| T | T | C | C | T | | C | T |
| A | A | A | A | A | | A | A |
| G | G | G | G | G | | G | G |

| Peptide (Common Name, *Species*) |
|---|
| Ponericin-G4 (Ponerine ant, *Pachycondyla goeldii*) |
| Uperin 3.2 (Toadlet, *Uperoleia inundata*) |
| Cecropin (Bombyx mori (Silk moth) |
| Cyanophylyctin (Skittering frog, *Euphlyctis cyanophlyctis*) |
| Pandinin-1 (Emperor scorpion) |
| Cathelicidin (Bornean orangutan, *Pongo pygmaeus*) |
| Ocellatin-2 (Argus frog, *Leptodactylus ocellatus*) |
| Ascaphin-6 (Coastal tailed frog, *Ascaphus truei*) |
| Dermadistinctin-L (Monkey frog, Phyllomedusa distincta) |
| Bactericidin (Tobacco hawkmoth, *Manduca sexta*) |
| Cecropin-D-like peptide (Greater wax moth, *Galleria mellonella*) |
| Pseudin-1 (Paradoxical frog, *Pseudis paradoxa*) |
| Caerin-1.4 (Centralian tree frog, *Litoria gilleni*) |
| Brevinin-2Ec (Marsh frog, *Pelophylas ridibundus*) |
| Pleuocidin (Winter flounder, *Pleuronectes americanus*) |
| Chemokine Platelet Basic Protein CXCL7 (Pig, Sus scrofa) |
| Clavanin-A (Sea squirt, Styela clava) |
| Chemokine IL-8 (Human, *Homo sapiens*) |

FIG. 2 (Cont.)

tIL-5 hIL-7 hIL-13 hIL-21 bIFN-γ hIFN-γ

Pp-1

Pp-2

Pp-3

Pp-4

ANTIMICROBIAL PEPTIDES WITH ALPHA-CORE HELICES

CROSS REFERENCE TO RELATED APPLICATIONS

This application is a continuation of U.S. application Ser. No. 18/053,981 filed Nov. 9, 2022, now U.S. Pat. No. 11,987,607, issued May 21, 2024, which is a division of U.S. application Ser. No. 16/612,242, filed Nov. 8, 2019, now abandoned which is the U.S. national stage application of International Application No. PCT/US2018/032133, filed May 10, 2018, which claims the benefit under 35 U.S.C. § 119(e) of U.S. Provisional Application No. 62/505,013, filed May 11, 2017, the contents of each of which are incorporated by reference in their entirety into the present disclosure.

REFERENCE TO AN ELECTRONIC SEQUENCE LISTING

The contents of the electronic sequence listing (0WVR-254302-US3_Sequence Listing; Size: 5,244,323 bytes; and Date of Creation: Apr. 15, 2024) is herein incorporated by reference in its entirety.

BACKGROUND

Antimicrobial host defense peptides (AHDPs) are an evolutionarily ancient arm of host defense that first arose in prokaryotes as a means to neutralize microbial competitors. Subsequently, similar peptides evolved in all classes of eukaryotes where they continue to act as a first line of defense against microbial invaders. AHDPs from nearly all organisms are typically small in size, cationic and amphipathic, properties that are thought to be essential for their microbicidal activities. Cationicity is thought to confer selectivity towards microorganisms, given their relatively electronegative surface charge and membrane potential. Amphipathicity has been shown to be an important feature by which AHDPs can successfully associate with and permeabilize target microbial membranes.

Given that eukaryotic AHDPs act on rapidly-evolving bacterial targets, they must necessarily react in kind to retain their potency. This host-microbe arms race has led to positive selective pressure allowing for a very high degree of mutational tolerance within AHAPs, which have been shown to be some of the most rapidly evolving sequences studied to date. When compounded over an evolutionary time scale, this process has generated an exceptionally diverse repertoire of eukaryotic sequences and structures capable of exerting microbicidal effects.

The inherent diversity in eukaryotic AHDPs has made the identification of common microbicidal motifs and SARs elusive. While a number of research groups have utilized computational and/or QSAR methods in an attempt to characterize such motifs, they have largely been focused on identifying improved drug candidates. As a result, while these investigations have identified numerous optimized or improved peptide-based therapeutics, the unifying physico-chemical and three-dimensional features that confer microbicidal activity to native peptides have yet to be fully defined.

SUMMARY

The present disclosure describes the identification of a consensus formula representing α-helical antimicrobial peptides (AHAPs) from broad classes of higher eukaryotes. When this formula is applied as a component of a logical search method against proteomic databases, it consistently retrieves a majority of the known AHAP families. Furthermore, this consensus formula helped identify a number of putative novel microbicidal peptides, as well as covert antimicrobial activities within proteins for which no such activity has yet been assigned. In accordance with one embodiment of the present disclosure, therefore, provided are microbicidal peptides, compositions, methods, and uses, and computer systems and methods for identifying consensus formulae and for searching microbicidal peptides.

In one embodiment, the present disclosure provides a peptide comprising an amino acid sequence selected from the group consisting of SEQ ID NO: 1-14, and an amino acid derived from anyone of SEQ ID NO: 1-14 with one amino acid substitution, wherein the peptide is not longer than 100 amino acid residues in length.

In some embodiments, the peptide has antimicrobial activity. In some embodiments, the peptide comprises the amino acid sequence of anyone of SEQ ID NO: 1-14. In some embodiments, the peptide comprises the amino acid sequence of SEQ ID NO: 13 or 14.

In some embodiments, the peptide is not longer than 75 amino acid residues in length. In some embodiments, the peptide is not longer than 60 amino acid residues in length.

Also provided, in some embodiments, is a peptide comprising an amino acid sequence of SEQ ID NO:19-6860 or an amino acid derived from a sequence of SEQ ID NO:19-6860 with one amino acid substitution, wherein the peptide is not longer than 100 amino acid residues in length.

Also provided, in some embodiments, is a fusion peptide comprising a first fragment selected from the sequences of SEQ ID NO:19-6860 or an amino acid derived from a sequence of SEQ ID NO:19-6860 with one amino acid substitution, and a second fragment having antimicrobial activity, wherein the fusion peptide is not longer than 100 amino acid residues in length. In some embodiments, the second fragment comprises a gamma-core motif comprising two anti-parallel β-sheets interposed by a short turn region with a GXC or CXG sequence pattern integrated into one of the β-sheets. In some embodiments, the gamma-core motif comprises CPTAQLIATLKNGRKICLDLQ (SEQ ID NO: 15) or a first amino acid sequence having at least 85% sequence identity to SEQ ID NO: 15.

In some embodiments, the peptide or fusion peptide includes one or more non-natural amino acid residues.

Also provided, in one embodiment, is a composition comprising the peptide or the fusion peptide and a pharmaceutically acceptable carrier. In some embodiments, the composition further comprises an antimicrobial agent. In some embodiments, the antimicrobial agent is selected from the group consisting of imipenem, ceftazidime, colistin, chloroquine, artemisinin, vancomycin and daptomycin.

Also provided, is one embodiment, is a method of treating an infection in a patient in need thereof, comprising administering to the patient an effective amount of the composition. In some embodiments, the infection is caused by a Gram-negative bacterium, a Gram-positive bacterium or a fungus.

Computer-implemented methods are also provided. In one embodiment, a method of identifying a peptide having antimicrobial activity is provided, comprising: identifying a consensus formula from aligned amino acid sequences known to have an antimicrobial activity; tuning the consensus formula with a test search against a plurality of proteins with known antimicrobial activity; and searching in a protein database, with one or more processors, for amino acid fragments matching the consensus formula, wherein the search takes as input one or more criteria selected from the group consisting of location of the fragment in a protein, size of the protein, organism of the protein, and signal peptide of the protein.

In some embodiments, the tuning comprising shortening the length of the consensus formula or changing substation options at one or more amino acid residues.

In another embodiment, a computer-implemented method of identifying an α-helical antimicrobial peptide is provided, comprising: searching in a protein database, with one or more processors, for amino acid fragments matching a consensus formula: X-[VILMCFWYAG]-[KRHEDNQSTAG]-[KRHEDNQSTAG]-[VILMCFWYAG]-[VILMCFWYAG]-[KRHEDNQSTAG]-[KRHEDNQSTAG]-[VILMCFWYAG]-X-[KRHEDNQSTAG]-[VILMCFWYAG](SEQ ID NO:6861), wherein X denotes any amino acid residue; filtering the searched fragments based on presence of a signal peptide in the respective protein; and evaluating the searched fragments for one or more criteria selected from the group consisting of: hydrophobic moment; mean hydrophobicity; net charge; frequencies or ratio of K and R; and isoelectric point.

BRIEF DESCRIPTION OF THE DRAWINGS

Certain features of various embodiments of the present technology are set forth with particularity in the appended claims. A better understanding of the features and advantages of the technology will be obtained by reference to the following detailed description that sets forth illustrative embodiments, in which the principles of the technology are utilized, and the accompanying drawings of which:

FIGS. 1A and 1B show graphic representations of α-core sequence formula. 1A. Helical wheel depiction of the 18 residue α-core sequence formula. 1B. Schematic representing linear formula. Hydrophobic residues (F, W, Y, V, I, L, M, C, A, G) are in various shades of green, with greater hydrophobicity indicated by increasingly darker hues. Hydrophilic residues (K, R, H, E, D, N, Q, S, T, A, G) are represented by: blue—cationic; red—anionic; orange—uncharged polar. Alanine (light green) and glycine (yellow) are included with both hydrophilic and hydrophobic groups. H—hydrophobic; P—polar.

DETAILED DESCRIPTION

Figure 1A:
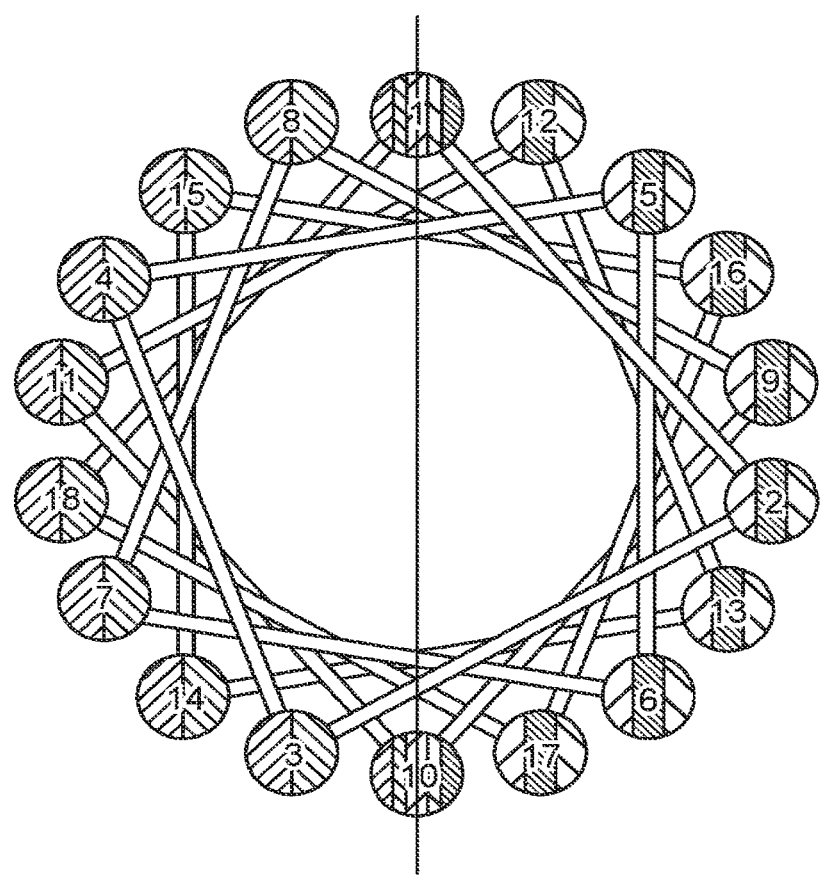

It is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

It must be noted that as used herein and in the appended claims, the singular forms "a", "an", and "the" include plural referents unless the context clearly dictates otherwise. Thus, for example, reference to "a peptide" includes a plurality of peptides.

1. Definitions

Unless defined otherwise, all technical and scientific terms used herein have the same meaning as commonly understood by one of ordinary skill in the art to which this disclosure belongs. As used herein the following terms have the following meanings.

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel character-istic(s) claimed. "Consisting of" shall mean excluding more than trace elements of other ingredients and substantial method steps. Embodiments defined by each of these tran-sition terms are within the scope of this disclosure.

The term "about" when used before a numerical desig-nation, e.g., temperature, time, amount, and concentration, including range, indicates approximations which may vary by (+) or (−) 10%, 5% or 1%.

As used herein, the term "sequence identity" refers to a level of amino acid residue or nucleotide identity between two peptides or between two nucleic acid molecules. When a position in the compared sequence is occupied by the same base or amino acid, then the molecules are identical at that position. A peptide (or a polypeptide or peptide region) has a certain percentage (for example, at least about 60%, or at least about 65%, or at least about 70%, or at least about 75%, or at least about 80%, or at least about 83%, or at least about 85%, or at least about 90%, or at least about 95%, or at least about 98% or at least about 99%) of "sequence identity" to another sequence means that, when aligned, that percentage of bases (or amino acids) are the same in comparing the two sequences. It is noted that, for any sequence ("reference sequence") disclosed in this application, sequences having at least about 60%, or at least about 65%, or at least about 70%, or at least about 75%, or at least about 80%, or at least about 83%, or at least about 85%, or at least about 90%, or at least about 95%, or at least about 98% or at least about 99% sequence identity to the reference sequence are also within the disclosure.

Likewise, the present disclosure also includes sequences that have one, two, three, four, or five substitution, deletion or addition of amino acid residues or nucleotides as com-pared to the reference sequences.

In any of the embodiments described herein, analogs of a peptide comprising any amino acid sequence described herein are also provided, which have at least about 80%, or at least about 83%, or at least about 85%, or at least about 90%, or at least about 95%, or at least about 98%, or at least about 99% sequence identity to any of reference amino acid sequences. In some embodiments, the analogs include one, two, three, four, or five substitution, deletion or addition of amino acid residues as compared to the reference sequences. In some embodiments, the substitution is a conservative substitution.

As used herein the term "amino acid" refers to either natural and/or unnatural or synthetic amino acids, including glycine and both the D and L optical isomers, amino acid analogs and peptidomimetics. In some embodiments, non-natural amino acids are useful for tuning or engineering the helix or other secondary or tertiary structures of a peptide or protein for desired antimicrobial properties.

As is well-known in the art, a "conservative substitution" of an amino acid or a "conservative substitution variant" of a peptide refers to an amino acid substitution which main-tains: 1) the secondary structure of the peptide; 2) the charge or hydrophobicity of the amino acid; and 3) the bulkiness of the side chain or any one or more of these characteristics. Illustratively, the well-known terminologies "hydrophilic residues" relate to serine or threonine. "Hydrophobic resi-dues" refer to leucine, isoleucine, phenylalanine, valine or alanine, or the like. "Positively charged residues" relate to lysine, arginine, ornithine, or histidine. "Negatively charged residues" refer to aspartic acid or glutamic acid. Residues having "bulky side chains" refer to phenylalanine, trypto-phan or tyrosine, or the like. A list of illustrative conserva-tive amino acid substitutions is given in Table A.

TABLE A

| For Amino Acid | Replace With |
| --- | --- |
| Alanine | D-Ala, Gly, Aib, β-Ala, L-Cys, D-Cys |
| Arginine | D-Arg, Lys, D-Lys, Orn D-Orn |
| Asparagine | D-Asn, Asp, D-Asp, Glu, D-Glu Gln, D-Gln |
| Aspartic Acid | D-Asp, D-Asn, Asn, Glu, D-Glu, Gln, D-Gln |
| Cysteine | D-Cys, S-Me-Cys, Met, D-Met, Thr, D-Thr, L-Ser, D-Ser |
| Glutamine | D-Gln, Asn, D-Asn, Glu, D-Glu, Asp, D-Asp |
| Glutamic Acid | D-Glu, D-Asp, Asp, Asn, D-Asn, Gln, D-Gln |
| Glycine | Ala, D-Ala, Pro, D-Pro, Aib, β-Ala |
| Isoleucine | D-Ile, Val, D-Val, Leu, D-Leu, Met, D-Met |
| Leucine | Val, D-Val, Met, D-Met, D-Ile, D-Leu, Ile |
| Lysine | D-Lys, Arg, D-Arg, Orn, D-Orn |
| Methionine | D-Met, S-Me-Cys, Ile, D-Ile, Leu, D-Leu, Val, D-Val |
| Phenylalanine | D-Phe, Tyr, D-Tyr, His, D-His, Trp, D-Trp |
| Proline | D-Pro |
| Serine | D-Ser, Thr, D-Thr, allo-Thr, L-Cys, D-Cys |
| Threonine | D-Thr, Ser, D-Ser, allo-Thr, Met, D-Met, Val, D-Val |
| Tyrosine | D-Tyr, Phe, D-Phe, His, D-His, Trp, D-Trp |
| Valine | D-Val, Leu, D-Leu, Ile, D-Ile, Met, D-Met |

Alternatively, non-limiting examples of conservative amino acid substitutions are provided in Table B below, where a similarity score of 0 or higher indicates conservative substitution between the two amino acids.

TABLE B

|  | C | G | P | S | A | T | D | E | N | Q | H | K | R | V | M | I | L | F | Y | W |
| --- | --- | --- | --- | --- | --- | --- | --- | --- | --- | --- | --- | --- | --- | --- | --- | --- | --- | --- | --- | --- |
| W | −8 | −7 | −6 | −2 | −6 | −5 | −7 | −7 | −4 | −5 | −3 | −3 | 2 | −6 | −4 | −5 | −2 | 0 | 0 | 17 |
| Y | 0 | −5 | −5 | −3 | −3 | −3 | −4 | −4 | −2 | −4 | 0 | −4 | −5 | −2 | −2 | −1 | −1 | 7 | 10 |  |
| F | −4 | −5 | −5 | −3 | −4 | −3 | −6 | −5 | −4 | −5 | −2 | −5 | −4 | −1 | 0 | 1 | 2 | 9 |  |  |
| L | −6 | −4 | −3 | −3 | −2 | −2 | −4 | −3 | −3 | −2 | −2 | −3 | −3 | 2 | 4 | 2 | 6 |  |  |  |
| I | −2 | −3 | −2 | −1 | −1 | 0 | −2 | −2 | −2 | −2 | −2 | −2 | −2 | 4 | 2 | 5 |  |  |  |  |
| M | −5 | −3 | −2 | −2 | −1 | −1 | −3 | −2 | 0 | −1 | −2 | 0 | 0 | 2 | 6 |  |  |  |  |  |
| V | −2 | −1 | −1 | −1 | 0 | 0 | −2 | −2 | −2 | −2 | −2 | −2 | −2 | 4 |  |  |  |  |  |  |
| R | −4 | −3 | 0 | 0 | −2 | −1 | −1 | −1 | 0 | 1 | 2 | 3 | 6 |  |  |  |  |  |  |  |
| K | −5 | −2 | −1 | 0 | −1 | 0 | 0 | 0 | 1 | 1 | 0 | 5 |  |  |  |  |  |  |  |  |
| H | −3 | −2 | 0 | −1 | −1 | −1 | 1 | 1 | 2 | 3 | 6 |  |  |  |  |  |  |  |  |  |
| Q | −5 | −1 | 0 | −1 | 0 | −1 | 2 | 2 | 1 | 4 |  |  |  |  |  |  |  |  |  |  |
| N | −4 | 0 | −1 | 1 | 0 | 0 | 2 | 1 | 2 |  |  |  |  |  |  |  |  |  |  |  |

TABLE B-continued

| | C | G | P | S | A | T | D | E | N | Q | H | K | R | V | M | I | L | F | Y | W |
|---|---|---|---|---|---|---|---|---|---|---|---|---|---|---|---|---|---|---|---|---|
| E | -5 | 0 | -1 | 0 | 0 | 0 | 3 | 4 | | | | | | | | | | | | |
| D | -5 | 1 | -1 | 0 | 0 | 0 | 4 | | | | | | | | | | | | | |
| T | -2 | 0 | 0 | 1 | 1 | 3 | | | | | | | | | | | | | | |
| A | -2 | 1 | 1 | 1 | 2 | | | | | | | | | | | | | | | |
| S | 0 | 1 | 1 | 1 | | | | | | | | | | | | | | | | |
| P | -3 | -1 | 6 | | | | | | | | | | | | | | | | | |
| G | -3 | 5 | | | | | | | | | | | | | | | | | | |
| C | 12 | | | | | | | | | | | | | | | | | | | |

Alternatively, non-limiting examples of conservative amino acid substitutions include substitutions of a polar amino acid with a different polar amino acid, or substitutions of a hydrophobic amino acid with a different hydrophobic amino acid, as illustrated in Table C below. Each of the polar amino acids or hydrophobic amino acids, in some embodiments, can be substituted with Ala or Gly.

TABLE C

| Polar amino acids | K, R, H, E, D, N, Q, S, T (or substituted with A or G) |
|---|---|
| Hydrophobic amino acids | V, I, L, M, C, F, W, Y (or substituted with A or G) |

As used herein, the term "composition" refers to a preparation suitable for administration to an intended patient for therapeutic purposes that contains at least one pharmaceutically active ingredient, including any solid form thereof. The composition may include at least one pharmaceutically acceptable component to provide an improved formulation of the compound, such as a suitable carrier. In certain embodiments, the composition is formulated as a film, gel, patch, or liquid solution.

As used herein, the term "pharmaceutically acceptable" indicates that the indicated material does not have properties that would cause a reasonably prudent medical practitioner to avoid administration of the material to a patient, taking into consideration the disease or conditions to be treated and the respective route of administration. For example, it is commonly required that such a material be essentially sterile.

2. Antimicrobial α-Helical Antimicrobial Peptides

The present disclosure, in some embodiments, describes a computational approach for generating a systemic formula from known α-helical antimicrobial peptides and using the formula to screen for new α-helical antimicrobial peptides. The systematic formula integrates features of idealized amphipathic and/or antimicrobial helices spanning up to 18 positions of canonical right-handed α-helices. Results demonstrate that nearly all families of known antimicrobial α-helical peptides align with the formula. In addition, many previously uncharacterized sequences were predicted to have direct antimicrobial activity. Synthesis of selected candidates and in vitro efficacy against human pathogens affirmed the veracity of model predictions and established validity of the α-core formula and search strategy. As a result, novel protein and peptide families and their specific sequences are identified as having potent and direct microbicidal efficacy that heretofore had not been ascribed.

The identified protein and peptide families and their specific sequences are provided in Tables 2-4 and SEQ ID NO:518-6860. In some embodiments, provided is an isolated peptide comprising an amino acid sequence of Table 2, 3 or 4 or any one of SEQ ID NO:518-6860, or an amino acid derived therefrom with one, two or three amino acid substitution. In some embodiments, the substitution is a conservative substitution. In some embodiments, the substitution is the replacement of a polar amino acid with a different polar amino acid (or A or G), or the replacement of a hydrophobic amino acid with a different hydrophobic amino acid (or A or G).

In some embodiments, provided is an isolated peptide comprising an amino acid sequence selected from the group consisting of SEQ ID NO: 1-14 and an amino acid derived from anyone of SEQ ID NO: 1-14 with one, two or three amino acid substitution. In some embodiments, the substitution is a conservative substitution. In some embodiments, the substitution is the replacement of a polar amino acid with a different polar amino acid (or A or G), or the replacement of a hydrophobic amino acid with a different hydrophobic amino acid (or A or G). In some embodiments, the peptide comprises the amino acid sequence of anyone of SEQ ID NO: 1-14.

In some embodiments, the peptide is a fragment or fusion peptide described from natural proteins. In some embodiments, the peptide differs from natural proteins by at least an amino acid substation, addition or deletion.

In some embodiments, the peptide is not longer than 100 amino acid residues in length. In some embodiments, the peptide is not longer than 95, 90, 85, 80, 75, 70, 65, 60, 55, 50, 45, 40, 35, 30 or 25 amino acid resides in length. In some embodiments, the peptide has antimicrobial activity.

Fusion peptides are also described. In one embodiment, the present disclosure provides a fusion peptide comprising a first fragment selected from the sequences of Table 2, 3 or 4 or any one of SEQ ID NO:518-6860 or an amino acid derived from a sequence of Table 2, or 3 or any one of SEQ ID NO:518-6860 with one, or two or three amino acid substitution, and a second fragment having antimicrobial activity. In some embodiments, the second fragment comprises a gamma-core motif comprising two anti-parallel β-sheets interposed by a short turn region with a GXC or CXG sequence pattern integrated into one of the β-sheets.

As used herein, the terms "gamma-core motif," or "γ-core," and equivalents thereof refer to a multidimensional protein signature, in particular a multidimensional antimicrobial signature, that is characterized by two anti-parallel β-sheets interposed by a short turn region with a conserved GXC (dextromeric) or CXG (levomeric) sequence pattern integrated into one β-sheet. Additional features that characterize the γ-core motif include a hydrophobic bias toward the C-terminal aspect and cationic charge positioned at the inflection point and termini of the β-sheet domains, polarizing charge along the longitudinal axis of the γ-core.

The kinocidin γ-core ($\gamma_{KC}$ core) signature is an iteration of the antimicrobial peptide γ-core ($\gamma_{AP}$), conforming to an anti-parallel β-hairpin comprised of a 13-17 amino acid pattern with a central hydrophobic region typically flanked by basic residues. The $\gamma_{KC}$ core motif can be characterized by the following consensus sequence formula:

(SEQ ID NO: 6862)

$$NH_2 \; [C]-[X_{10-13}]-[GX_{2-3}C]-[X_2]-[P] \; COOH$$

Human IL-8, which contains the kinocidin γ-core ($\gamma_{KC}$ core) signature, has the sequence:

(SEQ ID NO: 6863)

$$NH_2 \; CANTEIIVKLSDGRELCLDP \; COOH$$

This fragment of the IL-8 sequence is consistent with the consensus $\gamma_{KC}$-core motif. Furthermore, many kinocidins exhibit a recurring amino acid position pattern, consistent with the consensus $\gamma_{KC}$ core formula:

(SEQ ID NO: 6864)

$$NH_2 \; CX_4Z_3X_{0-2}[K^{81}]X_{1-3}G][K^{72}][B^{86}][Z^{92}]C[Z^{86}][D^{86}][P^{95}] \; COOH$$

(SEQ ID NO: 6865)

R          N where Z represents the hydrophobic residues A, F, I, L, V, W, Y; B represents the charged or polar residues D, E, H, K, N, R, Q; C, P, or G correspond to cysteine, proline, or glycine, respectively, X indicates variable amino acid position; and numeric superscripts of bracketed positions indicate relative frequency in percent, with common alternate residues listed beneath.

In one embodiment, the gamma-core motif comprises CPTAQLIATLKNGRKICLDLQ (SEQ ID NO: 15) or a first amino acid sequence having at least 85% sequence identity to SEQ ID NO: 15. In one aspect, variants of the γ-core can include CPTAQLIATLKNGRKICLDLQP (SEQ ID NO: 16), CPTAQLIATLKNGRKICLDLQAP (SEQ ID NO: 17) and CPTAQLIATLKNGRKICLDLQA (SEQ ID NO: 18).

A linker can optionally be included between the first fragment and the second fragment, which is preferably 10 amino acids or fewer in length. In some aspect, the spacer is 9, 8, 6, 5, 4, 3, 2 amino acids in length or shorter. The spacer can include any amino acids, such as Ala, Pro, Cys, and Gly.

In some embodiments, the fusion peptide has antimicrobial activity. In some embodiments, the peptides may be conjugated to therapeutic agents, prodrugs, peptides, proteins, enzymes, viruses, lipids, biological response modifiers, pharmaceutical agents, or PEG.

The peptides may be conjugated or fused to a therapeutic agent, which may include detectable labels such as radioactive labels, an immunomodulator, a hormone, an enzyme, an oligonucleotide, a photoactive therapeutic or diagnostic agent, a cytotoxic agent, which may be a drug or a toxin, an ultrasound enhancing agent, a non-radioactive label, a combination thereof and other such agents known in the art. The peptides can be detectably labeled by coupling it to a chemiluminescent compound. The presence of the chemiluminescent-tagged antigen-binding polypeptide is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

3. Synthesis of Antimicrobial Peptides

The peptides described herein can be ordered from a commercial source or partially or fully synthesized using methods well known in the art (e.g., chemical and/or biotechnological methods). In certain embodiments, the peptides are synthesized according to solid phase peptide synthesis protocols that are well known in the art. In another embodiment, the peptide is synthesized on a solid support according to the well-known Fmoc protocol, cleaved from the support with trifluoroacetic acid and purified by chromatography according to methods known to persons skilled in the art. In other embodiments, the peptide is synthesized utilizing the methods of biotechnology that are well known to persons skilled in the art. In one embodiment, a DNA sequence that encodes the amino acid sequence information for the desired peptide is ligated by recombinant DNA techniques known to persons skilled in the art into an expression plasmid (for example, a plasmid that incorporates an affinity tag for affinity purification of the peptide), the plasmid is transfected into a host organism for expression, and the peptide is then isolated from the host organism or the growth medium, e.g., by affinity purification.

The peptides can be also prepared by using recombinant expression systems. Generally, this involves inserting the nucleic acid molecule into an expression system to which the molecule is heterologous (i.e., not normally present). One or more desired nucleic acid molecules encoding a peptide of the disclosure may be inserted into the vector. When multiple nucleic acid molecules are inserted, the multiple nucleic acid molecules may encode the same or different peptides. The heterologous nucleic acid molecule is inserted into the expression system or vector in proper sense (5'→3') orientation relative to the promoter and any other 5' regulatory molecules, and correct reading frame.

Purified peptides may be obtained by several methods. The peptide is preferably produced in purified form (preferably at least about 80% or 85% pure, more preferably at least about 90% or 95% pure) by conventional techniques. Depending on whether the recombinant host cell is made to secrete the peptide into growth medium (see U.S. Pat. No. 6,596,509 to Bauer et al., which is hereby incorporated by reference in its entirety), the peptide can be isolated and purified by centrifugation (to separate cellular components from supernatant containing the secreted peptide) followed by sequential ammonium sulfate precipitation of the supernatant. The fraction containing the peptide is subjected to gel filtration in an appropriately sized dextran or polyacrylamide column to separate the peptides from other proteins. If necessary, the peptide fraction may be further purified by HPLC.

4. Antimicrobial Compositions and Formulations

Compositions and formulations that include any one or more of the peptides as disclosed herein are also provided. In one embodiment, the composition includes any one or more of the peptides and a pharmaceutically acceptable carrier.

"Pharmaceutically acceptable carriers" refers to any diluents, excipients, or carriers that may be used in the compositions of the disclosure. Pharmaceutically acceptable carriers include ion exchangers, alumina, aluminum stearate, lecithin, serum proteins, such as human serum albumin, buffer substances, such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Suitable pharmaceutical carriers are described in *Remington's Pharmaceutical Sciences*, Mack Publishing Company, a standard reference text in this field. They are preferably selected with respect to the intended form of administration, that is, oral tablets, capsules, elixirs, syrups and the like, and consistent with conventional pharmaceutical practices.

The pharmaceutical compositions of the disclosure can be manufactured by methods well known in the art such as conventional granulating, mixing, dissolving, encapsulating, lyophilizing, or emulsifying processes, among others. Compositions may be produced in various forms, including granules, precipitates, or particulates, powders, including freeze dried, rotary dried or spray dried powders, amorphous powders, injections, emulsions, elixirs, suspensions or solutions. Formulations may optionally contain stabilizers, pH modifiers, surfactants, bioavailability modifiers and combinations of these.

Pharmaceutical formulations may be prepared as liquid suspensions or solutions using a sterile liquid, such as oil, water, alcohol, and combinations thereof. Pharmaceutically suitable surfactants, suspending agents or emulsifying agents, may be added for oral or parenteral administration. Suspensions may include oils, such as peanut oil, sesame oil, cottonseed oil, corn oil and olive oil. Suspension preparation may also contain esters of fatty acids, such as ethyl oleate, isopropyl myristate, fatty acid glycerides and acetylated fatty acid glycerides. Suspension formulations may include alcohols, such as ethanol, isopropyl alcohol, hexadecyl alcohol, glycerol and propylene glycol. Ethers, such as poly(ethyleneglycol), petroleum hydrocarbons, such as mineral oil and petrolatum, and water may also be used in suspension formulations.

The compositions of this disclosure are formulated for pharmaceutical administration to a mammal, preferably a human being. Such pharmaceutical compositions of the disclosure may be administered in a variety of ways, preferably parenterally.

Sterile injectable forms of the compositions of this disclosure may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation. Compounds may be formulated for parenteral administration by injection such as by bolus injection or continuous infusion. A unit dosage form for injection may be in ampoules or in multi-dose containers.

In addition to dosage forms described above, pharmaceutically acceptable excipients and carriers and dosage forms are generally known to those skilled in the art and are included in the disclosure. It should be understood that a specific dosage and treatment regimen for any particular patient will depend upon a variety of factors, including the activity of the specific peptide employed, the age, body weight, general health, sex and diet, renal and hepatic function of the patient, and the time of administration, rate of excretion, drug combination, judgment of the treating physician or veterinarian and severity of the particular disease being treated.

In some embodiments, the composition can further include a secondary antimicrobial agent. Non-limiting examples of such agents include imipenem, ceftazidime, colistin, chloroquine, artemisinin, vancomycin and daptomycin.

5. Therapeutic Methods

Methods of using the peptides, compositions and formulations of the present disclosure are also described. In one embodiment, the methods are for preventing or treating an infection of a microorganism. The microorganism can be a bacterium, such as a Gram-negative bacterium or a Gram-positive bacterium, a fungus, or a parasite.

The peptides, compositions and formulations are also useful for treating a disease or condition associated with an infection, such as wound abscess, catheter biofilm, pneumonia, and bacteremia.

In some embodiments, the treatment methods further include administration, concurrently or sequentially, of a second secondary antimicrobial agent. Non-limiting examples of such agents include imipenem, ceftazidime, colistin, chloroquine, artemisinin, vancomycin and daptomycin.

The peptides, compositions and formulations of the disclosure may be administered to the systemic circulation via parental administration. The term "parenteral" as used herein includes subcutaneous, intravenous, intramuscular, intra-articular, intra-synovial, intrasternal, intrathecal, intra-hepatic, intralesional and intracranial injection or infusion techniques. However, in cases where the infection is local (e.g., on the skin), the composition may be administered locally, such as topically.

6. Computational System and Methods

Figure 10:
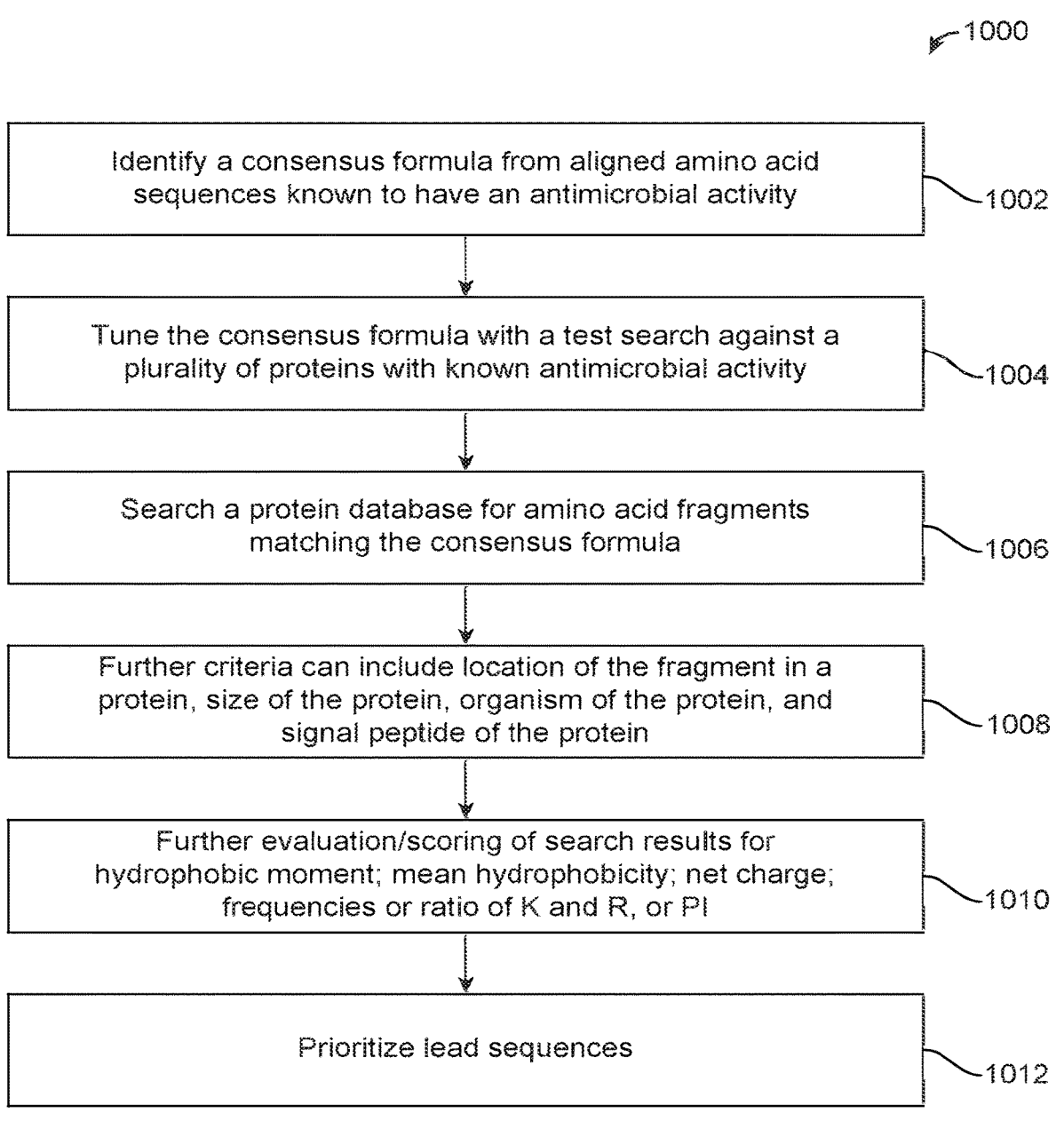
FIG. 10 illustrates an example process flow chart of a method, according to some implementations.

The present disclosure, in some embodiments, provides computer-implemented methods for identifying antimicrobial sequences and related systems and non-transitory computer-readable media. In one embodiment, a computer-implemented method of identifying a peptide having antimicrobial activity is provided, as illustrated in FIG. 10 which is a process flow chart of a method 1000. The various processing operations and/or data flows depicted in FIG. 10

(and in the other drawing figures) are described in greater detail herein. The described operations may be accomplished using some or all of the system components described in detail above and, in some implementations, various operations may be performed in different sequences and various operations may be omitted. Additional operations may be performed along with some or all of the operations shown in the depicted flow diagrams. One or more operations may be performed simultaneously. Accordingly, the operations as illustrated (and described in greater detail below) are exemplary by nature and, as such, should not be viewed as limiting.

At step 1002, pursuant to a user command, the system, such as personal computing device, identifies a consensus formula from aligned amino acid sequences known to have an antimicrobial activity, such as those known as α-helical antimicrobial peptides. An example formula is X-[VILMCFWYAG]-[KRHEDNQSTAG]-[KRHEDNQSTAG]-[VILMCFWYAG]-[VILMCFWYAG]-[KRHEDNQSTAG]-[KRHEDNQSTAG]-[VILMCFWYAG]-X-[KRHEDNQSTAG]-[VILMCFWYAG](SEQ ID NO:6861), wherein X denotes any amino acid residue. The formula can be tested with a dataset that include known antimicrobial peptides and the formula can be further tuned (step 1004). For instance, the formula may be shortened or lengthened, or certain amino acid residues can include more or fewer substitutions.

The formula can then be used to search in a protein database (step 1006) for sequences or fragment that match the requirement of the formula. In some embodiments, the search query include one or more criteria such as location of the fragment in a protein, size of the protein, and organism of the protein (step 1008). In particular, in one embodiment, the search results are further evaluated for the presence of a signal peptide in the corresponding protein.

In some embodiments, the search results are further evaluated with respect to their biological, chemical, physical or sequential properties. Example properties include, without limitation, hydrophobic moment; mean hydrophobicity; net charge; frequencies or ratio of K and R; and isoelectric point (PI). Each of these evaluation scores can be used for prioritizing, ranking, filtering the search results (step 1012). Optionally, some of the search results are synthesized and tested in the lab for their antimicrobial activities.

Figure 11:
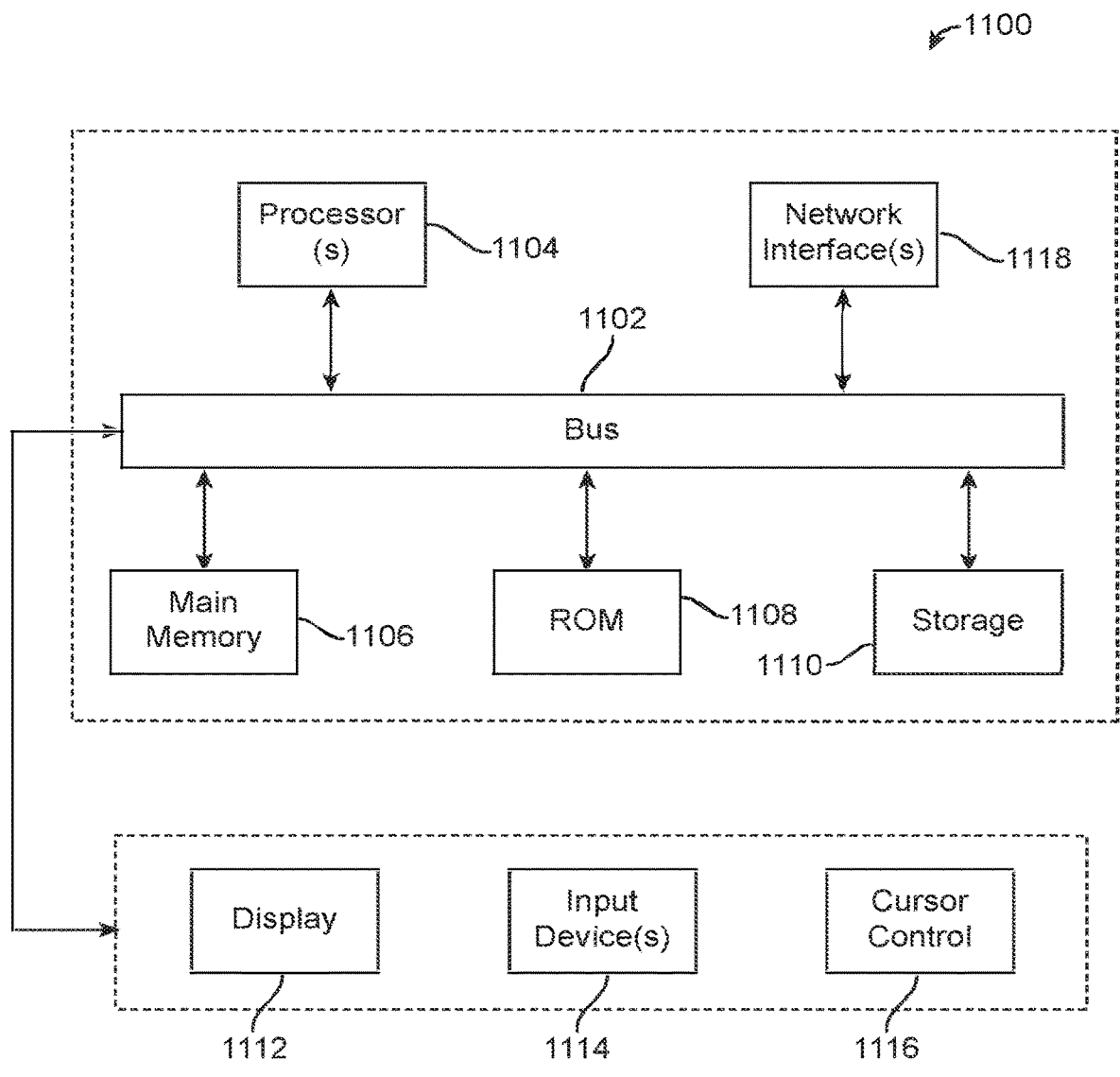
FIG. 11 illustrates a block diagram of an example computer system in which any of the implementations described herein may be implemented.

FIG. 11 depicts a block diagram of an example computer system 1100 in which any of the embodiments described herein may be implemented. The computer system 1100 includes a bus 1102 or other communication mechanism for communicating information, one or more hardware processors 1104 coupled with bus 1102 for processing information. Hardware processor(s) 1104 may be, for example, one or more general purpose microprocessors.

The computer system 1100 also includes a main memory 1106, such as a random access memory (RAM), cache and/or other dynamic storage devices, coupled to bus 1102 for storing information and instructions to be executed by processor 1104. Main memory 1106 also may be used for storing temporary variables or other intermediate information during execution of instructions to be executed by processor 1104. Such instructions, when stored in storage media accessible to processor 1104, render computer system 1100 into a special-purpose machine that is customized to perform the operations specified in the instructions.

The computer system 1100 further includes a read only memory (ROM) 1108 or other static storage device coupled to bus 1102 for storing static information and instructions for processor 1104. A storage device 1110, such as a magnetic disk, optical disk, or USB thumb drive (Flash drive), etc., is provided and coupled to bus 1102 for storing information and instructions.

The computer system 1100 may be coupled via bus 1102 to a display 1112, such as a cathode ray tube (CRT) or LCD display (or touch screen), for displaying information to a computer user. An input device 1114, including alphanumeric and other keys, is coupled to bus 1102 for communicating information and command selections to processor 1104. Another type of user input device is cursor control 1116, such as a mouse, a trackball, or cursor direction keys for communicating direction information and command selections to processor 1104 and for controlling cursor movement on display 1112. This input device typically has two degrees of freedom in two axes, a first axis (e.g., x) and a second axis (e.g., y), that allows the device to specify positions in a plane. In some embodiments, the same direction information and command selections as cursor control may be implemented via receiving touches on a touch screen without a cursor.

The computing system 1100 may include a user interface module to implement a GUI that may be stored in a mass storage device as executable software codes that are executed by the computing device(s). This and other modules may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables.

In general, the word "module," as used herein, refers to logic embodied in hardware or firmware, or to a collection of software instructions, possibly having entry and exit points, written in a programming language, such as, for example, Java, C or C++. A software module may be compiled and linked into an executable program, installed in a dynamic link library, or may be written in an interpreted programming language such as, for example, BASIC, Perl, or Python. It will be appreciated that software modules may be callable from other modules or from themselves, and/or may be invoked in response to detected events or interrupts. Software modules configured for execution on computing devices may be provided on a computer readable medium, such as a compact disc, digital video disc, flash drive, magnetic disc, or any other tangible medium, or as a digital download (and may be originally stored in a compressed or installable format that requires installation, decompression or decryption prior to execution). Such software code may be stored, partially or fully, on a memory device of the executing computing device, for execution by the computing device. Software instructions may be embedded in firmware, such as an EPROM. It will be further appreciated that hardware modules may be comprised of connected logic units, such as gates and flip-flops, and/or may be comprised of programmable units, such as programmable gate arrays or processors. The modules or computing device functionality described herein are preferably implemented as software modules, but may be represented in hardware or firmware. Generally, the modules described herein refer to logical modules that may be combined with other modules or divided into sub-modules despite their physical organization or storage.

The computer system 1100 may implement the techniques described herein using customized hard-wired logic, one or more ASICs or FPGAs, firmware and/or program logic which in combination with the computer system causes or programs computer system 1100 to be a special-purpose machine. According to one embodiment, the techniques herein are performed by computer system 1100 in response to processor(s) 1104 executing one or more sequences of one or more instructions contained in main memory 1106. Such instructions may be read into main memory 1106 from another storage medium, such as storage device 1110. Execution of the sequences of instructions contained in main memory 1106 causes processor(s) 1104 to perform the process steps described herein. In alternative embodiments, hard-wired circuitry may be used in place of or in combination with software instructions.

The term "non-transitory media," and similar terms, as used herein refers to any media that store data and/or instructions that cause a machine to operate in a specific fashion. Such non-transitory media may comprise non-volatile media and/or volatile media. Non-volatile media includes, for example, optical or magnetic disks, such as storage device 1110. Volatile media includes dynamic memory, such as main memory 1106. Common forms of non-transitory media include, for example, a floppy disk, a flexible disk, hard disk, solid state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge, and networked versions of the same.

Non-transitory media is distinct from but may be used in conjunction with transmission media. Transmission media participates in transferring information between non-transitory media. For example, transmission media includes coaxial cables, copper wire and fiber optics, including the wires that comprise bus 1102. Transmission media can also take the form of acoustic or light waves, such as those generated during radio-wave and infra-red data communications.

Various forms of media may be involved in carrying one or more sequences of one or more instructions to processor 1104 for execution. For example, the instructions may initially be carried on a magnetic disk or solid state drive of a remote computer. The remote computer can load the instructions into its dynamic memory and send the instructions over a telephone line using a modem. A modem local to computer system 1100 can receive the data on the telephone line and use an infra-red transmitter to convert the data to an infra-red signal. An infra-red detector can receive the data carried in the infra-red signal and appropriate circuitry can place the data on bus 1102. Bus 1102 carries the data to main memory 1106, from which processor 1104 retrieves and executes the instructions. The instructions received by main memory 1106 may retrieves and executes the instructions. The instructions received by main memory 1106 may optionally be stored on storage device 1110 either before or after execution by processor 1104.

The computer system 1100 also includes a communication interface 1118 coupled to bus 1102. Communication interface 1118 provides a two-way data communication coupling to one or more network links that are connected to one or more local networks. For example, communication interface 1118 may be an integrated services digital network (ISDN) card, cable modem, satellite modem, or a modem to provide a data communication connection to a corresponding type of telephone line. As another example, communication interface 1118 may be a local area network (LAN) card to provide a data communication connection to a compatible LAN (or WAN component to communicated with a WAN). Wireless links may also be implemented. In any such implementation, communication interface 1118 sends and receives electrical, electromagnetic or optical signals that carry digital data streams representing various types of information.

A network link typically provides data communication through one or more networks to other data devices. For example, a network link may provide a connection through local network to a host computer or to data equipment operated by an Internet Service Provider (ISP). The ISP in turn provides data communication services through the world wide packet data communication network now commonly referred to as the "Internet". Local network and Internet both use electrical, electromagnetic or optical signals that carry digital data streams. The signals through the various networks and the signals on network link and through communication interface 1118, which carry the digital data to and from computer system 1100, are example forms of transmission media.

The computer system 1100 can send messages and receive data, including program code, through the network(s), network link and communication interface 1118. In the Internet example, a server might transmit a requested code for an application program through the Internet, the ISP, the local network and the communication interface 1118.

The received code may be executed by processor 1104 as it is received, and/or stored in storage device 1110, or other non-volatile storage for later execution.

Each of the processes, methods, and algorithms described in the preceding sections may be embodied in, and fully or partially automated by, code modules executed by one or more computer systems or computer processors comprising computer hardware. The processes and algorithms may be implemented partially or wholly in application-specific circuitry.

The various features and processes described above may be used independently of one another, or may be combined in various ways. All possible combinations and sub-combinations are intended to fall within the scope of this disclosure. In addition, certain method or process blocks may be omitted in some implementations. The methods and processes described herein are also not limited to any particular sequence, and the blocks or states relating thereto can be performed in other sequences that are appropriate. For example, described blocks or states may be performed in an order other than that specifically disclosed, or multiple blocks or states may be combined in a single block or state. The example blocks or states may be performed in serial, in parallel, or in some other manner. Blocks or states may be added to or removed from the disclosed example embodiments. The example systems and components described herein may be configured differently than described. For example, elements may be added to, removed from, or rearranged compared to the disclosed example embodiments.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Any process descriptions, elements, or blocks in the flow diagrams described herein and/or depicted in the attached figures should be understood as potentially representing modules, segments, or portions of code which include one or more executable instructions for implementing specific logical functions or steps in the process. Alternate implementations are included within the scope of the embodiments described herein in which elements or functions may be deleted, executed out of order from that shown or discussed, including substantially concurrently or in reverse order, depending on the functionality involved, as would be understood by those skilled in the art.

It should be emphasized that many variations and modifications may be made to the above-described embodiments, the elements of which are to be understood as being among other acceptable examples. All such modifications and variations are intended to be included herein within the scope of this disclosure. The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

Engines, Components, and Logic

Certain embodiments are described herein as including logic or a number of components, engines, or mechanisms. Engines may constitute either software engines (e.g., code embodied on a machine-readable medium) or hardware engines. A "hardware engine" is a tangible unit capable of performing certain operations and may be configured or arranged in a certain physical manner. In various example embodiments, one or more computer systems (e.g., a standalone computer system, a client computer system, or a server computer system) or one or more hardware engines of a computer system (e.g., a processor or a group of processors) may be configured by software (e.g., an application or application portion) as a hardware engine that operates to perform certain operations as described herein.

In some embodiments, a hardware engine may be implemented mechanically, electronically, or any suitable combination thereof. For example, a hardware engine may include dedicated circuitry or logic that is permanently configured to perform certain operations. For example, a hardware engine may be a special-purpose processor, such as a Field-Programmable Gate Array (FPGA) or an Application Specific Integrated Circuit (ASIC). A hardware engine may also include programmable logic or circuitry that is temporarily configured by software to perform certain operations. For example, a hardware engine may include software executed by a general-purpose processor or other programmable processor. Once configured by such software, hardware engines become specific machines (or specific components of a machine) uniquely tailored to perform the configured functions and are no longer general-purpose processors. It will be appreciated that the decision to implement a hardware engine mechanically, in dedicated and permanently configured circuitry, or in temporarily configured circuitry (e.g., configured by software) may be driven by cost and time considerations.

Accordingly, the phrase "hardware engine" should be understood to encompass a tangible entity, be that an entity that is physically constructed, permanently configured (e.g., hardwired), or temporarily configured (e.g., programmed) to operate in a certain manner or to perform certain operations described herein. As used herein, "hardware-implemented engine" refers to a hardware engine. Considering embodiments in which hardware engines are temporarily configured (e.g., programmed), each of the hardware engines need not be configured or instantiated at any one instance in time. For example, where a hardware engine comprises a general-purpose processor configured by software to become a special-purpose processor, the general-purpose processor may be configured as respectively different special-purpose processors (e.g., comprising different hardware engines) at different times. Software accordingly configures a particular processor or processors, for example, to constitute a particular hardware engine at one instance of time and to constitute a different hardware engine at a different instance of time.

Hardware engines can provide information to, and receive information from, other hardware engines. Accordingly, the described hardware engines may be regarded as being communicatively coupled. Where multiple hardware engines exist contemporaneously, communications may be achieved through signal transmission (e.g., over appropriate circuits and buses) between or among two or more of the hardware engines. In embodiments in which multiple hardware engines are configured or instantiated at different times, communications between such hardware engines may be achieved, for example, through the storage and retrieval of information in memory structures to which the multiple hardware engines have access. For example, one hardware engine may perform an operation and store the output of that operation in a memory device to which it is communicatively coupled. A further hardware engine may then, at a later time, access the memory device to retrieve and process the stored output. Hardware engines may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented engines that operate to perform one or more operations or functions described herein. As used herein, "processor-implemented engine" refers to a hardware engine implemented using one or more processors.

Similarly, the methods described herein may be at least partially processor-implemented, with a particular processor or processors being an example of hardware. For example, at least some of the operations of a method may be performed by one or more processors or processor-implemented engines. Moreover, the one or more processors may also operate to support performance of the relevant operations in a "cloud computing" environment or as a "software as a service" (SaaS). For example, at least some of the operations may be performed by a group of computers (as examples of machines including processors), with these operations being accessible via a network (e.g., the Internet) and via one or more appropriate interfaces (e.g., an Application Program Interface (API)).

The performance of certain of the operations may be distributed among the processors, not only residing within a single machine, but deployed across a number of machines.

In some example embodiments, the processors or processor-implemented engines may be located in a single geographic location (e.g., within a home environment, an office environment, or a server farm). In other example embodiments, the processors or processor-implemented engines may be distributed across a number of geographic locations.

Language

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Although an overview of the subject matter has been described with reference to specific example embodiments, various modifications and changes may be made to these embodiments without departing from the broader scope of embodiments of the present disclosure. Such embodiments of the subject matter may be referred to herein, individually or collectively, by the term "invention" merely for convenience and without intending to voluntarily limit the scope of this application to any single disclosure or concept if more than one is, in fact, disclosed.

The embodiments illustrated herein are described in sufficient detail to enable those skilled in the art to practice the teachings disclosed. Other embodiments may be used and derived therefrom, such that structural and logical substitutions and changes may be made without departing from the scope of this disclosure. The Detailed Description, therefore, is not to be taken in a limiting sense, and the scope of various embodiments is defined only by the appended claims, along with the full range of equivalents to which such claims are entitled.

It will be appreciated that an "engine," "system," "data store," and/or "database" may comprise software, hardware, firmware, and/or circuitry. In one example, one or more software programs comprising instructions capable of being executable by a processor may perform one or more of the functions of the engines, data stores, databases, or systems described herein. In another example, circuitry may perform the same or similar functions. Alternative embodiments may comprise more, less, or functionally equivalent engines, systems, data stores, or databases, and still be within the scope of present embodiments. For example, the functionality of the various systems, engines, data stores, and/or databases may be combined or divided differently.

"Open source" software is defined herein to be source code that allows distribution as source code as well as compiled form, with a well-publicized and indexed means of obtaining the source, optionally with a license that allows modifications and derived works.

The data stores described herein may be any suitable structure (e.g., an active database, a relational database, a self-referential database, a table, a matrix, an array, a flat file, a documented-oriented storage system, a non-relational No-SQL system, and the like), and may be cloud-based or otherwise.

EXAMPLES

Example 1. Identification of New Antimicrobial α-Core Helices

This example describes an experiment in which a consensus sequence formula was developed and used to search for new α-helical antimicrobial peptides (AHAPs) having microbiocidal activities.

Among the most potent natural antibiotics known to date include α-helical host defense peptides. These peptides effect a first line of defense against invading pathogens and have been isolated from species ranging from microbes to man. While many prior investigations have analyzed individual and class-specific properties through which these peptides convey function, machine-learning strategies to define unifying principles and underlying structure activity relationships (SARs) have been limited. In this example, a systematic formula encompassing features of idealized amphipathic and/or antimicrobial helices that span up to 18 positions of canonical right-handed α-helices was designed. The formula was then applied to search known protein databases seeking known as well as unforeseen proteins or peptides fulfilling its structural signature. Results demonstrate that nearly all families of known antimicrobial α-helical peptides align with this formula. Interestingly, logical search algorithms using this formula discovered many previously uncharacterized sequences predicted to have direct antimicrobial activity. Laboratory studies affirmed the veracity of predictions and established validity of the α-core formula and search strategy. As a result, new protein and peptide families and specific sequences are identified as having potent and direct microbicidal efficacy that heretofore had not been ascribed.

Methods and Materials

Identification of the α-Core Formula

To identify a consensus formula that was representative of nearly all classes of AHAPs, multiple sequence alignments with prototypical α-helical peptides using CLUSTAL W (www.ebi.ac.uk) were carried out. Alignments were then manually adjusted at certain positions using MEGA 6. Through iterative refinements of this process, an 18 residue generalized amphipathic formula emerged with sequence degeneracies at each position that was representative of nearly all classes of AHAPs. This formula can initiate at any of the positions that make up a standardized 18 residue α-helical wheel.

Assignment of Residue Polarity within the α-Core Formula

Within the formula, individual residues were categorized as either hydrophobic or hydrophilic as per the Wimley-White hydrophobicity scale, a scale that has been empirically derived and includes contributions from the peptide bond. One exception was for alanine (A), which was also included with the hydrophobic residues as per the Eisenberg and Kyte-Doolittle hydrophobicity scales. This assignment was made in-part due to preliminary studies that frequently localized alanine to the hydrophobic facet of many antimicrobial peptides.

Accuracy of Formula in Retrieving Helical Sequences

The amphipathic helical consensus formula above was queried against the PDB 3D database (www.wwpdb.org) to assess the fidelity of the formula in identifying helical domains. The first 100 non-redundant retrieved structures were scored for helicity of the target sequence. Proteins were considered to be a positive hit if the target sequence was more than 75% helical.

Use of α-Core Formula as a Database Query

The α-core sequence formula was used with the Scan-Prosite (prosite.expasy.org) tool to carry out iterative pattern searches of the UniProtKB Swiss-Prot database. While initial searches queried the database with varying lengths of the amphipathic sequence formula, it was ultimately found that a relatively short query sequence of 12 residues was most efficient at retrieving the majority of antimicrobial peptide sequences. Iteration 1 of this query sequence is listed below:

```
                                (SEQ ID NO: 6861)
  X-[VILMCFWYAG]-[KRHEDNQSTAG]-[KRHEDNQSTAG]-

[VILMCFWYAG]-[VILMCFWYAG]-[KRHEDNQSTAG]-

[KRHEDNQSTAG]-[VILMCFWYAG]-X-[KRHEDNQSTAG]-

[VILMCFWYAG]
```

After this optimization process, the sequence formula was used as a query against the UniProtKB Swiss-Prot and TrEMBL databases. The formula was advanced one position at a time through 18 iterations to represent an entire 18-residue helical wheel span. ScanProsite search results were further limited by: 1) protein size (<200 residues); 2) eukaryotic organisms; and 3) localization of the pattern to the C-terminal region using a "X(0,50)>" logical operator.

Signal Peptide and Biophysical Parameter Determination

Retrieved datasets were additionally screened for the presence of a signal peptide using SignalP 4.1 (www.cbs.dtu.dk). Hydrophobic moment ($\mu$H), mean hydrophobicity (H), net charge (Q-K and R (+1); H (+0.5); D and E (−1)) and K and R residue frequency were determined in batch using Python algorithms created for this purpose. PI was determined using the ExPasy Compute PI tool (web.expasy.org).

Candidate Peptides and HDPs

Select candidate microbicidal peptides were commercially synthesized by BioMatik (Biomatik USA, Wilmington, Delaware). Lyophilized peptides were reconstituted with ddIH20 and stored in aliquots at −20° C. LL-37 (Peptides International, Louisville, KY), a prototypic human AHAP, was used as a comparator in microbicidal assays.

Assay for Antimicrobial Activity

Putative antimicrobial peptides were assayed for microbicidal activity using a well-established radial diffusion method modified to pH 5.5 or 7.5. A panel of microorganisms was tested: Gram-positive *Staphylococcus aureus* (ISP 479C, ISP 479R); Gram-negative *Salmonella typhimurium* (MS 5996s, MS 14028), *Pseudomonas aeruginosa* (PA01), *Acinetobacter baumanni* (19606) and the fungus *Candida albicans* (36082S, 36082R). Logarithmic phase organisms were inoculated ($10^6$ CFU/ml) into buffered agarose, and poured into plates. Peptides (10 µg) were introduced into wells in the seeded matrix, and incubated for 3 h at 37° C. Nutrient overlay medium was applied, and assays incubated at 37° C. or 30° C. for bacteria or fungi, respectively. After 24*h*, zones of inhibition were measured. Independent experiments were repeated a minimum of two times.

Results

Derivation and Iterative Refinement of the α-Core Sequence Formula

Figure 2:
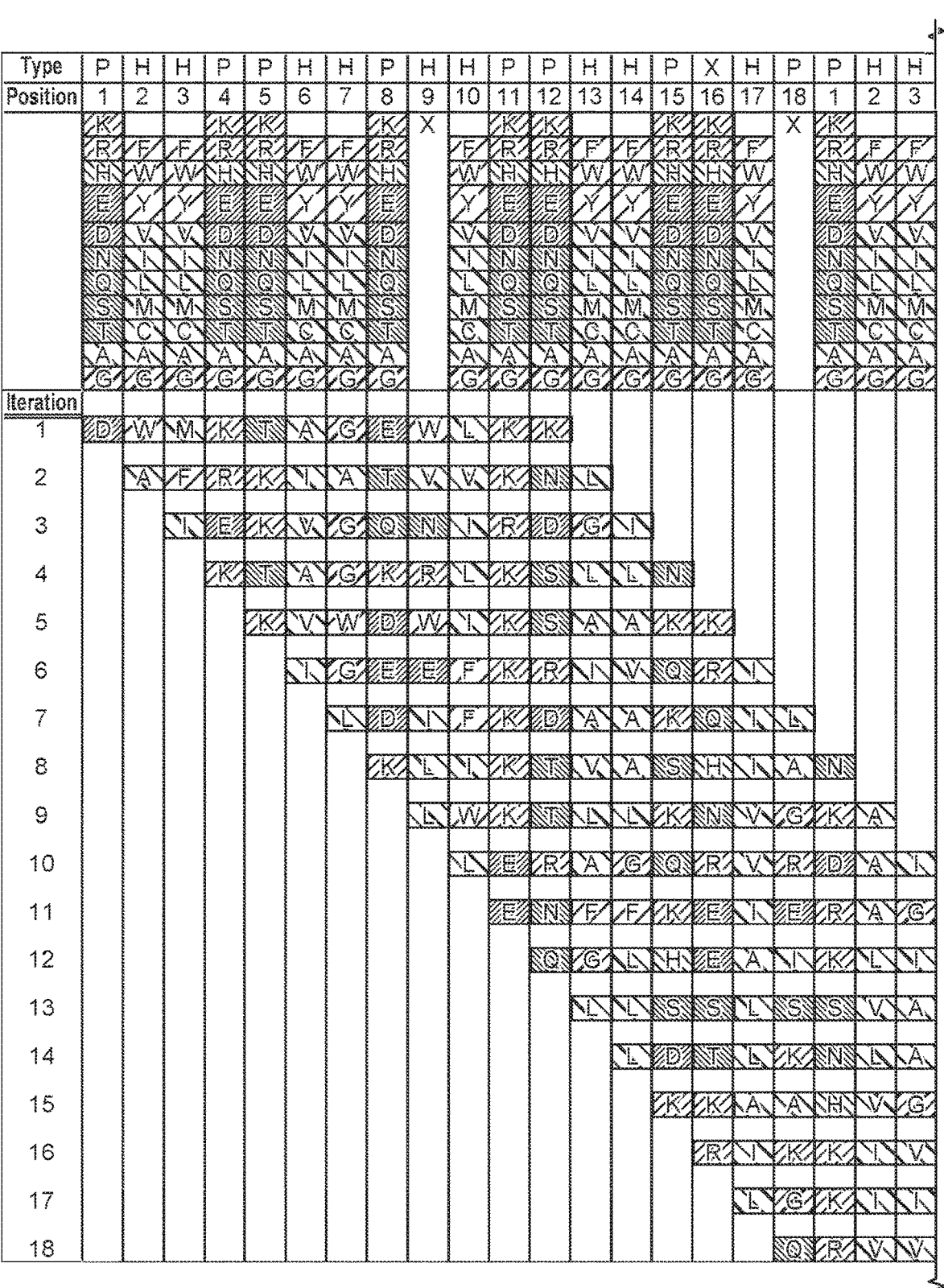
FIG. 2 shows the alignment of prototypic AHAPs with α-core sequence formula. 18 initiation points (SEQ ID NO:6867-6884) for the scanning iterative α-core formula are shown, representing the process by which the ProSite pattern search tool was utilized to query the SwissProt database. Coloration is as per FIG. 1A-1B.

In initial studies, alignments with prototypic representatives from all of the major classes of AHAPs were carried out to identify conserved sequence elements. This analysis revealed that nearly all of these prototypes could be aligned with a degenerate sequence formula wherein either polar or non-polar residues were assigned to positions along an amphipathic helix. Peptides adhered to this formula ranging from a minimal 11 to maximal 16 residue span corresponding to 3 to 4.5 turns of an α-helix. Based on this analysis, a consensus formula representative of nearly all of the major classes of AHAPs was extracted (FIGS. 1A-B and 2).

Once this preliminary consensus was defined, it was further refined by testing its efficiency to return α-helical domains when used as a query against the PDB protein structure database. As a baseline, versions of the formula lacking known helix breakers proline and glycine were carried out. Results of these analyses revealed that the efficiency of the formula in retrieving α-helical domains was very high, identifying these motifs (defined as spans that were at least 75% helical) with a frequency of 92-94%.

As many AHAPs are known to contain proline and glycine residues, subsequent tests to evaluate the impact of these residues on the efficiency of the formula were carried out. When proline was included within the sequence formula, α-helical domains within target sequences were retrieved less than 10% of the time. These findings strongly support the theory that proline, due to its side chain and steric constraints, is inconsistent with stable α-helix formation. Because of this, proline was excluded from the formula.

In contrast when glycine was allowed within the sequence formula, queries against the structure database revealed two different outcomes depending on whether targets had been determined in aqueous or non-polar environments. For structures determined in aqueous environments, the sequence formula retrieved α-helical domains approximately 74% of the time when a single glycine was present; a value that was reduced to 40% when two or more glycine residues were present. By comparison, when target structures were determined in non-polar environments (high levels of TFE, SDS, or micellar components), the presence of glycine had very little impact on peptide helicity. These studies revealed that the sequence formula retrieved α-helical domains approximately 92% if the time when as many as four glycine residues were present in the target sequence. Because of this, and since glycine is highly represented in AHAPs, this residue was included in the sequence formula. Moreover, a large number of biophysical studies have demonstrated that while many glycine-rich AHAPs are unstructured in aqueous environments, they nearly always adopt an α-helical conformation when interacting with the hydrophobic membrane environments of their microbial targets.

Alanine/Glycine Both Faces of Helix

Figure 3:
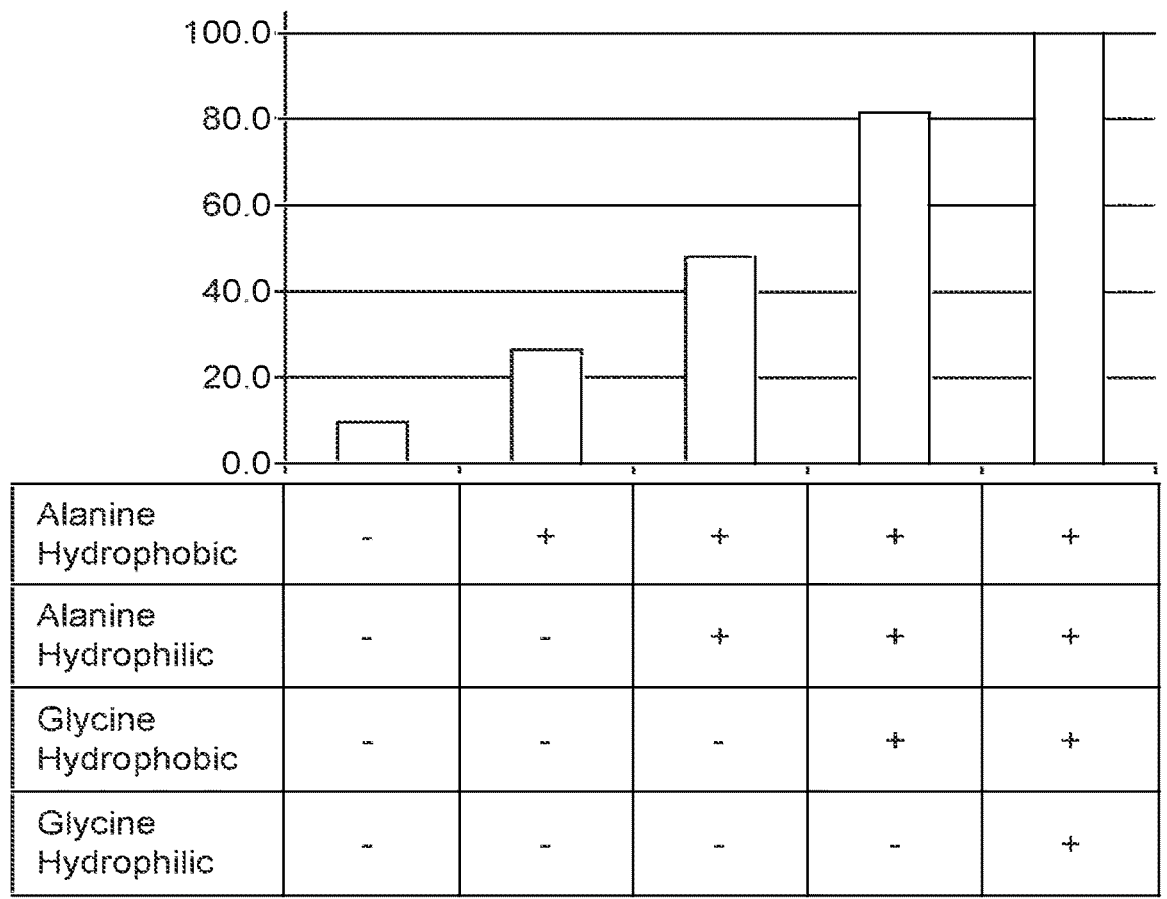
FIG. 3 illustrates the iterative optimization of the α-core formula. Iterative refinement of the α-core formula was carried out to assess the requirement for glycine and/or alanine as a component of either the polar (hydrophilic) or non-polar (hydrophobic) residue set. Percentage of returned sequences from a control AHAP dataset of more than 400 peptides are shown.

While the assignment of most residues to either the polar or non-polar residue group within the sequence formula was relatively straightforward based on the initial AHAP consensus and known residue-specific hydrophobicity values, the placement of alanine and glycine was less obvious due to their relatively neutral AG values in polar and non-polar environments. Because of this, the requirement for glycine and/or alanine on either the polar or non-polar face of the helix was assessed in an iterative manner via queries against a control dataset comprised of more than 400 AHAP peptides (FIG. 3). Preliminary versions of the formula, lacking alanine and glycine, failed to retrieve significant numbers (>10%) of the control AHAP study set (FIG. 3). The inclusion of alanine on the polar face of the amphipathic helix increased the retrieved fraction of peptides to 26%, and when alanine was added to both the polar and non-polar search terms the retrieved AHAPs increased to 48%. With respect to glycine a similar relationship was found. The addition of glycine to the polar face of the query sequence led to the identification of approximately 81% of the control AHAP dataset, and when glycine was included on both the polar and non-polar facets, the query retrieved close to 99% of the AHAP study set. As a result of this analysis, alanine and glycine were included as components of both the polar and non-polar query search terms.

α-Core Sequence Formula

Based on the above considerations, a linear α-core formula spanning all 18 positions of a canonical right-handed alpha helix was created, as shown below. When translated into three dimensions, the formula describes an idealized amphipathic helix, with distinct hydrophobic and hydrophilic facets. Positions in between the polar and nonpolar faces were assigned a value of "X" within the linear formula, leading to a polar angle (θ) maxima of 180° and minima of 140°. Due to the degenerate nature of the formula, each position along the helical span was represented by multiple polar or non-polar residues (below and FIGS. 1A-B and 2).

$$\text{Pos}_{(n\,0\text{-}17)} = [(\sin, n\delta), (\cos n\delta)]$$
$$\delta = 100 \text{ for standard } \alpha\text{-helix}$$

$$\begin{bmatrix} 1 & 2 & 3 & 4 & 5 & 6 & 7 & 8 & 9 & 10 & 11 & 12 & 13 & 14 & 15 & 16 & 17 & 18 \\ X\text{—}(P\text{—}H\text{—}H\text{—}P\text{—}P\text{—}H\text{—}H\text{—}P)\text{—}X\text{—}(H\text{—}P\text{—}P\text{—}H\text{—}H\text{—}P\text{—}P\text{—}H) \end{bmatrix}_{n=0\text{-}18}$$

P (polar) = [EDKRHQNTSAG]
H(hydrophobic = [VMCILFWYAG]

Primary Database Searches Using the α-Core Sequence Formula

Figure 4:
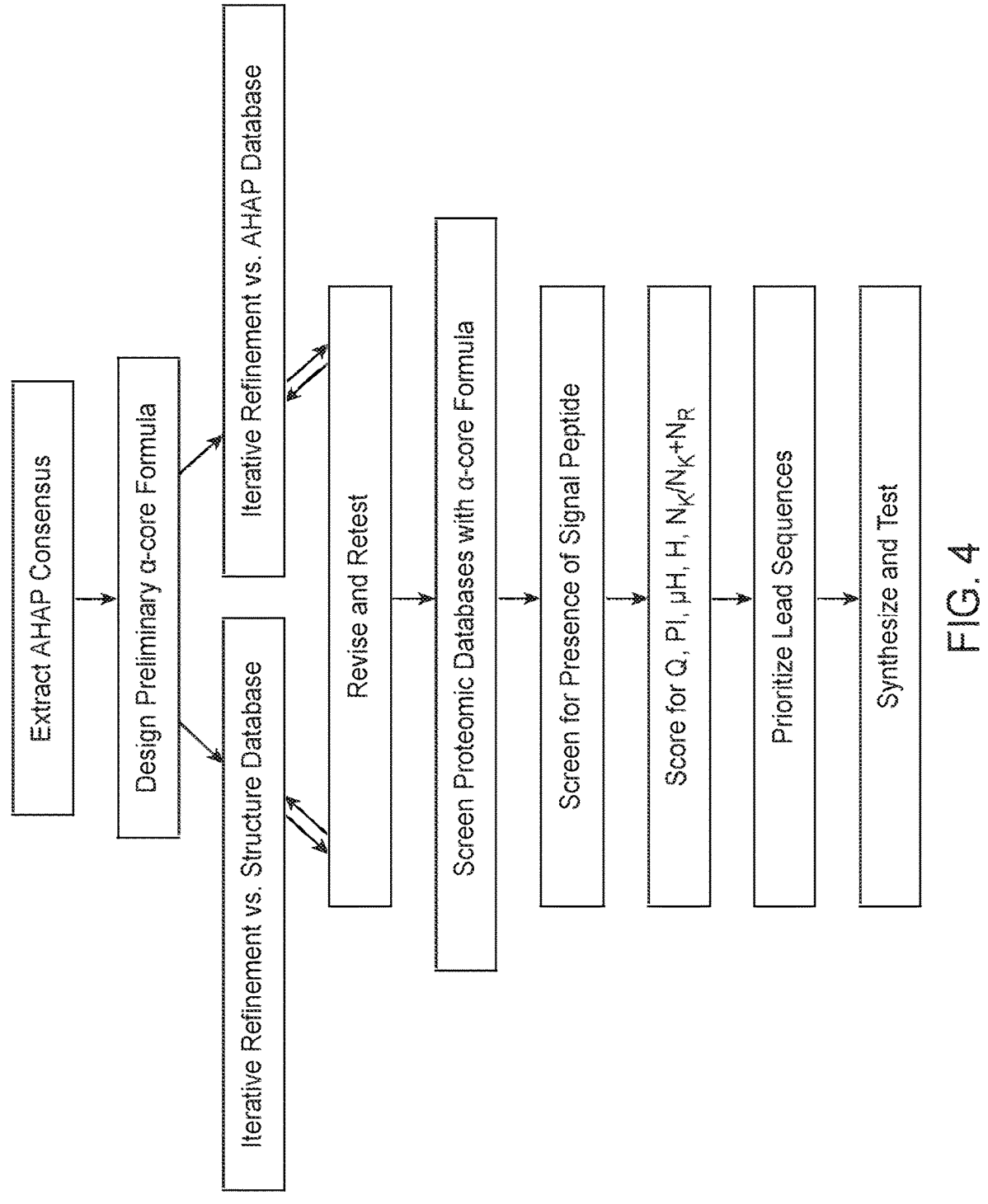
FIG. 4 illustrates a process of identifying new AHAP sequences.

Once refined, the α-core sequence formula was used as a query against the SwissProt and TrEMBL protein sequence databases (FIG. 4). As described in Methods, database queries were further limited to sequences that were eukaryotic in origin, less than 200 residues in length and within 50 residues of the C-terminus.

Returned raw datasets consisted of more than 70,000 sequences, often representing multiple target hits shifted along amphipathic helical spans of a single protein. Each of these returned hits was scored for hydrophobic moment, and sequences with the highest µH were extracted to generate a non-redundant dataset of approximately 13,000 unique sequences for downstream studies. Dataset proteins were also scored for the presence of a signal peptide, and sequences lacking this motif were removed to generate a final dataset of approximately 3,800 sequences.

Efficiency of the α-Core Sequence Formula

The results of the above database queries indicated that the amphipathic sequence algorithm was highly robust, retrieving members from nearly all of the known AHAP families (Table 1). Overall, the formula retrieved at least one member of more than 106 different helical peptide families representing approximately 94%, of all known AHAP classifications. Moreover, while the formula describes an idealized amphipathic helical structure, it nonetheless returned 827 individual antimicrobial peptide sequences, representing approximately 88% of all known AHAPs in the SwissProt database.

TABLE 1

α-Helical Peptide Families Retrieved with Alpha-Core Formula Search

|  | Class | Peptide | Organism |
|---|---|---|---|
| 1 | Cnidaria | Clavanins | Sea squirt |
| 2 | | Clavaspirin | Sea squirt |
| 3 | | Halocidin | Sea peach |
| 4 | | Halocyntin | Sea squirt |
| 5 | | Styelins | Sea squirt |
| 6 | Plants | Ginkbilobin | Ginko |
| 7 | | Thionin (helical domain) | Wheat |
| 8 | Arthropods | Amphipathic peptides | Scorpion |
| 9 | | Andropin | Fruit fly |
| 10 | | Anionic Antimicrobial peptide 2 | Moth |
| 11 | | Antifungal Protein MAF-1 | Fly |
| 12 | | Antimicrobial peptides (36.4, 143) | Scorpion |
| 13 | | Antimicrobial peptide ctriporin | Scorpion |
| 14 | | Antimicrobial peptide HsAp1 | Scorpion |
| 15 | | Bactericidin | Moth |
| 16 | | Bombolitin | Bee |
| 17 | | Cecropins | Moth/fly |

(SEQ ID NO: 6866)

TABLE 1-continued

α-Helical Peptide Families Retrieved with Alpha-Core Formula Search

|  | Class | Peptide | Organism |
|---|---|---|---|
| 18 | | Cecropin-D-like peptide | Moth |
| 19 | | Cryptonin | Cicada |
| 20 | | Cytotoxic linear peptide | Scorpion |
| 21 | | Decoralin | Wasp |
| 22 | | Dominulins | Wasp |
| 23 | | Eumenitins | Wasp |
| 24 | | Hadrurin | Scorpion |
| 25 | | Im-1 | Scorpion |
| 26 | | Imcroporin | Scorpion |
| 27 | | Lebocin-like peptide | Moth |
| 28 | | Mastoparans | Wasp |
| 29 | | Mastoparan-like peptides | Wasp |
| 30 | | Melittin | Bee |
| 31 | | Meucin-49 | Scorpion |
| 32 | | Moricins | Moth |
| 33 | | Moricin-like peptide A | Moth |
| 34 | | Mucroporin | Scorpion |
| 35 | | Mucroporin-like peptide | Scorpion |
| 36 | | Non-disulfide-bridged peptides | Scorpion |
| 37 | | Oxyopinin 4a | Spider |
| 38 | | Pandinin | Scorpion |
| 39 | | Parabutoporin | Scorpion |
| 40 | | Peptide BmKb1 | Scorpion |
| 41 | | Peptides Ctry | Scorpion |
| 42 | | Peptides Hp (Non-disulfide bridged) | Scorpion |
| 43 | | Pilosulins | Ant |
| 44 | | Ponericins | Ant |
| 45 | | Ponericin W-like | Scorpion |
| 46 | | Protonectin | Wasp |
| 48 | | Stomoxyn | fly |
| 49 | Fish | Chrysophsin | Sea Bream |
| 50 | | Pleurocidin | Flounder |
| 51 | | Pleurocidin-like peptide | Flounder |
| 52 | | Grammistins | Soapfish |

TABLE 1-continued

| | α-Helical Peptide Families Retrieved with Alpha-Core Formula Search | |
| Class | Peptide | Organism |
| --- | --- | --- |
| 53 | Pardaxins | Sole |
| 54 | Piscidin 3 | Striped bass |
| 55 Amphibians | Ascaphin | Frog |
| 56 | Aureins | Frog |
| 57 | Antimicrobial peptide PGQ | Frog |
| 58 | Antimicrobial peptides | Frog |
| 59 | Brevinins | Frog |
| 60 | Bombesin | Toad |
| 61 | Bombinins | Toad |
| 62 | Bombinin-like peptides | Toad |
| 63 | Caeridin | Frog |
| 64 | Caerins | Frog |
| 65 | Citropins | Frog |
| 66 | Cyanophlyctin | Frog |
| 67 | Dahleins | Frog |
| 68 | Dermadistinctins | Frog |
| 69 | Dermaseptins | Frog |
| 70 | Dermaseptin-like peptides | Frog |
| 71 | Dermatoxin | Frog |
| 72 | Distinctin-like peptide | Frog |
| 73 | Esculentins | Frog |
| 74 | Fallaxidins | Frog |
| 75 | Frenatins | Frog |
| 76 | Gaegurin | Frog |
| 77 | Grahamins | Frog |
| 78 | Guentherin | Frog |
| 79 | Hylins | Frog |
| 80 | Maximins | Toad |
| 81 | Nigrocins | Frog |
| 82 | Ocellatins | Frog |
| 83 | Palustrins | Frog |
| 84 | Phylloseptins | Frog |
| 85 | Pseudins | Frog |
| 86 | Prolevitide | Frog |
| 87 | Ranatuerins | Frog |
| 88 | Rugosins | Frog |
| 89 | Syphaxin | Frog |
| 90 | Temporins | Frog |
| 91 | Xenopsin | Frog |
| 92 | Uperins | Frog |
| 93 Reptiles | CRAMPs | Snake |
| 94 Birds | Cathelicidins | Chicken |
| 95 Mammals | Cathelicidins | Mammals |
| 96 | Cathelicidin related peptide SC5 | Sheep |
| 97 | CRAMP | Mouse |
| 98 | CAP-18 | Rabbit |
| 99 | PMAP-37 | Pig |
| 100 | Chemokines (helical domain) | Mammals |
| 101 | CXCL | |
| 102 | CCL | |
| 103 | XCL | |
| 104 | Granulysin | Human |
| 105 | Dermcidin | Human |
| 106 | NK-lysin | Horse |

Beyond retrieving a high proportion of known AHAPs, when limited to sequences with a PI of 8.5 or greater, the formula was also relatively specific in returning these sequences. Searches were carried out in several stages of either 0-50, or 51-200 residues, depending on whether a signal peptide test was applied. For the 0-50 residue set, approximately 71% of the retrieved sequences were known AHAPs; whereas, for the 51-200 residue set, approximately 27% of the identified sequences were α-helical antimicrobial proteins. Given that there are approximately 940 (see methods) named AHAPs in the 553,000 sequence SwissProt database (version 12-1-16), this represents and in-silico enrichment of approximately 130-fold.

With respect to other proteins retrieved by the sequence formula, the second most highly represented group were a variety of toxin peptides making up approximately 17% of the dataset. Beyond this, other protein families that were abundant in the retrieved dataset included: apovitellins, leptins, vasoactive intestinal proteins and uncharacterized proteins.

Residue Frequency

Figures 5A, 5B, 5C:
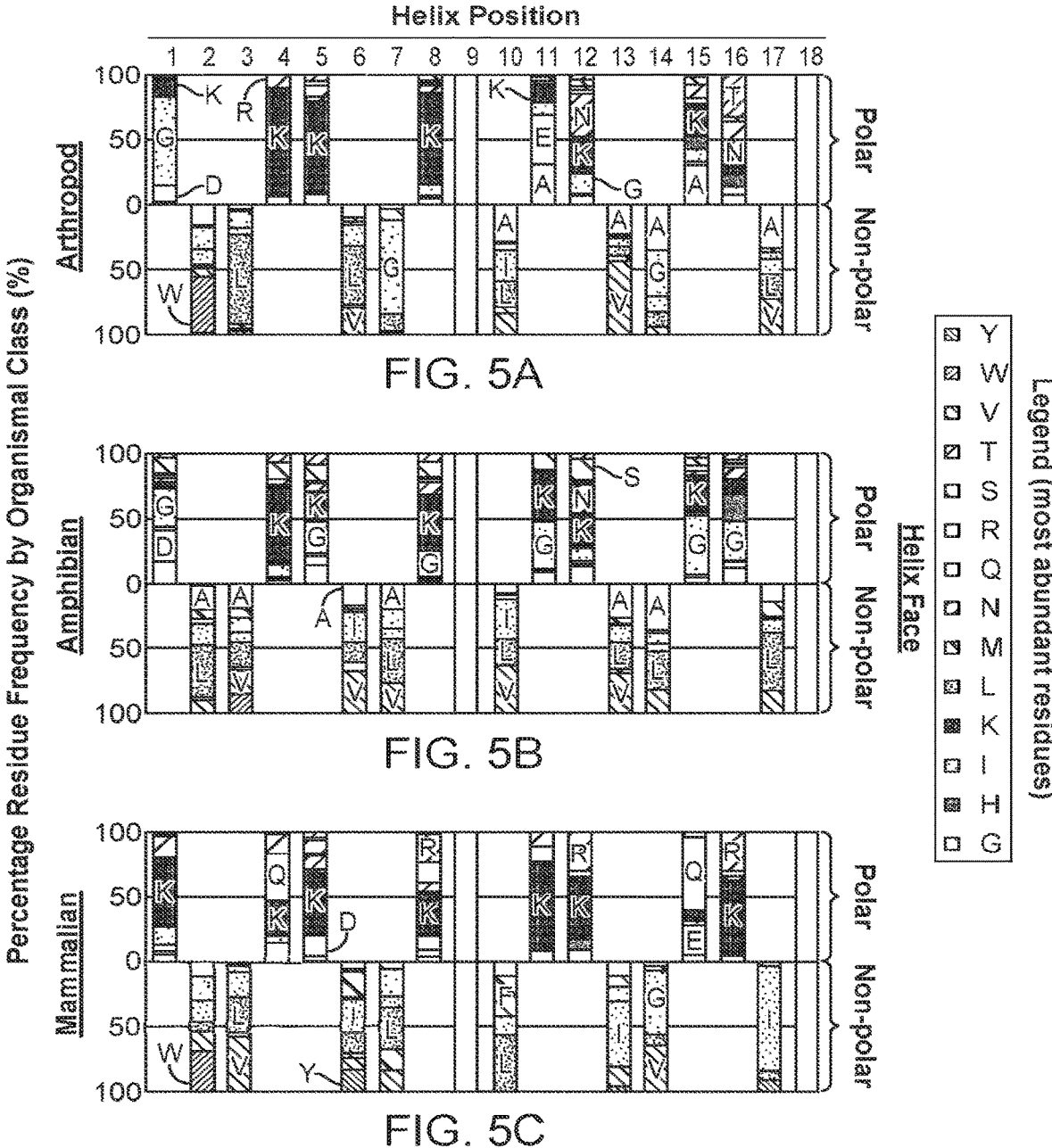
FIG. 5A-5C show the positional and spatial amphipathic residue frequency by class (arthropods, amphibians, higher vertebrates, respectively). Percentages of individual residues on either the polar or non-polar peptide face of study peptides are represented as various color blocks. Residues above the x-axis are found on the polar face of retrieved peptides and residues below the axis are found on the non-polar face.

Given that the α-core sequence formula returns aligned datasets, it was possible to score identified AHAP helices for the abundance of various residues at each position along an 18 residue amphipathic span. Moreover, given that the α-core formula identifies amphipathic patterns that are likely to form helices, it was also possible to make assumptions about the localization of specific resides to either the polar or non-polar facet of these structures. Due to the significant evolutionary distance between invertebrate and lower and higher vertebrate classes of AHAPs, the dataset was divided into three groups representing arthropod, amphibian and mammalian sequences (FIG. 5).

The analysis of residue frequency revealed a number of findings regarding the composition and hydrophilic and hydrophobic distribution of residues within returned AHAP helices. One finding of note was that glycine was highly represented in AHAPs of lower organisms, comprising approximately 30-35% of all residues in target amphipathic spans in arthropods and amphibians. While glycine was still abundant in mammals, it occurred less frequently representing about 15% of residues in the returned sequences.

It was also of interest to find that alanine, while abundant in amphipathic spans of arthropods and amphibians, was much less common in the identified sequences of mammals. Moreover, while alanine was found more frequently on the hydrophobic face of the peptide, it was also found with some frequency 10-30% on the polar face of peptides from arthropods and amphibians.

With respect to charged residues, it is of interest that lysine was the most abundant polar residue in non-mammalian species (30%) and was strongly preferred over arginine at an approximately 12:1 ratio. By contrast, in mammals this preference was markedly reduced, with this ratio decreasing to a 3:1 abundance of lysine to arginine. It is also of note to find negatively charged aspartic and glutamic acid residues within the returned sequences at a low frequency of approximately 5% in all species groups.

Biophysical Signatures

Beyond measuring the frequency of specific residues within returned AHAP helices, sequences were also scored for a number of biophysical parameters including: net charge (Q), isoelectric point (PI), hydrophobic moment (μH), hydrophobicity (H), and lysine to arginine (K/K+R) ratio.

In this analysis it was found that the average net charge for the AHAP subset of study helices (n=803) was +2.0. If only cationic sequences (Q>0.5; n=707) were considered this value rises to +2.7. By comparison the mean net charge for study toxin helices (n=717) was +1.3, and +0.6 for other study helices. With respect to hydrophobic moment, AHAP helices had an average μH of 0.52 while toxins had an average μH 0.42 and other peptides 0.39. While some reports suggest that mean hydrophobicity may be greater for toxins than for AHAPs, in this study values for hydrophobicity in the retrieved helices were similar, with an average H of 0.42 for AHAPs, and 0.34 for toxins as compared with other peptides (0.39).

Negative Gaussian Curvature

Figure 6:
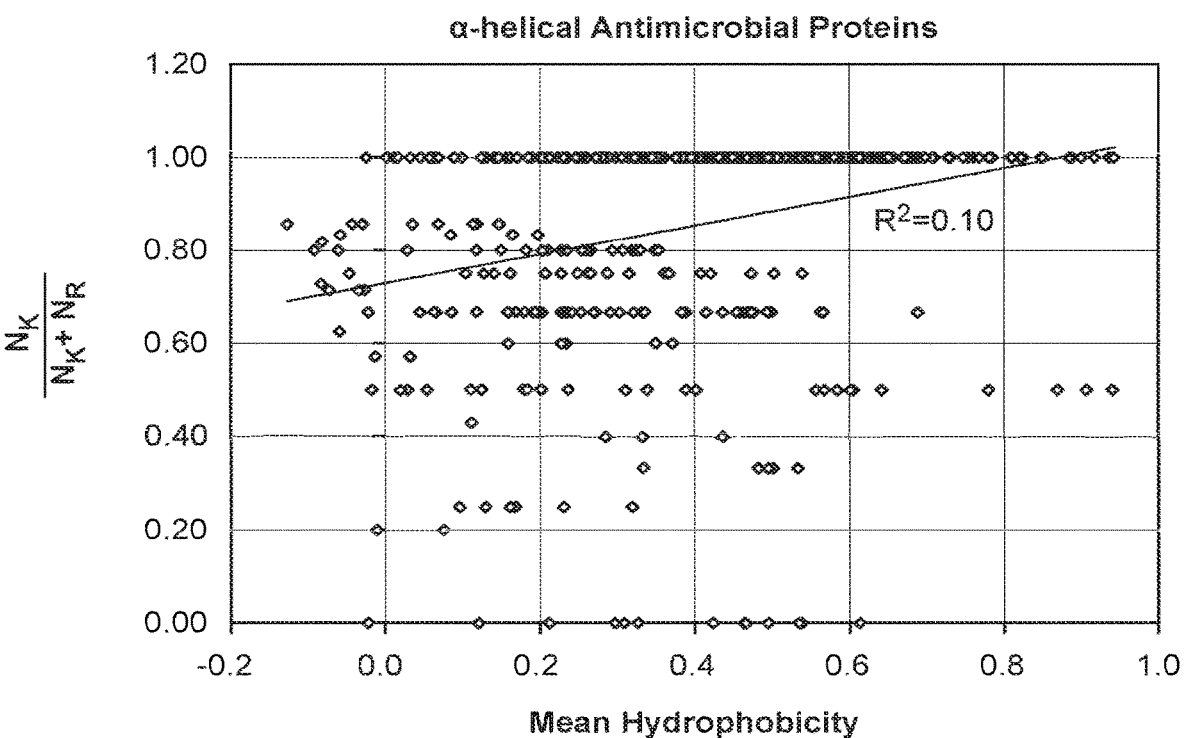
FIG. 6 shows the comparison of $N_K/N_K+N_R$ ratio and hydrophobicity in AHAP and toxin helices. Percentage of lysine ($N_K$) relative to arginine ($N_R$) expressed as ($N_K/N_K+N_R$) versus hydrophobicity (H) in study AHAPs and toxins. Preference of lysine as compared to arginine is reflected in an increased value of H for peptides capable of generating NGC in membranes as predicted by the saddle-splay rule.
Figure 6:
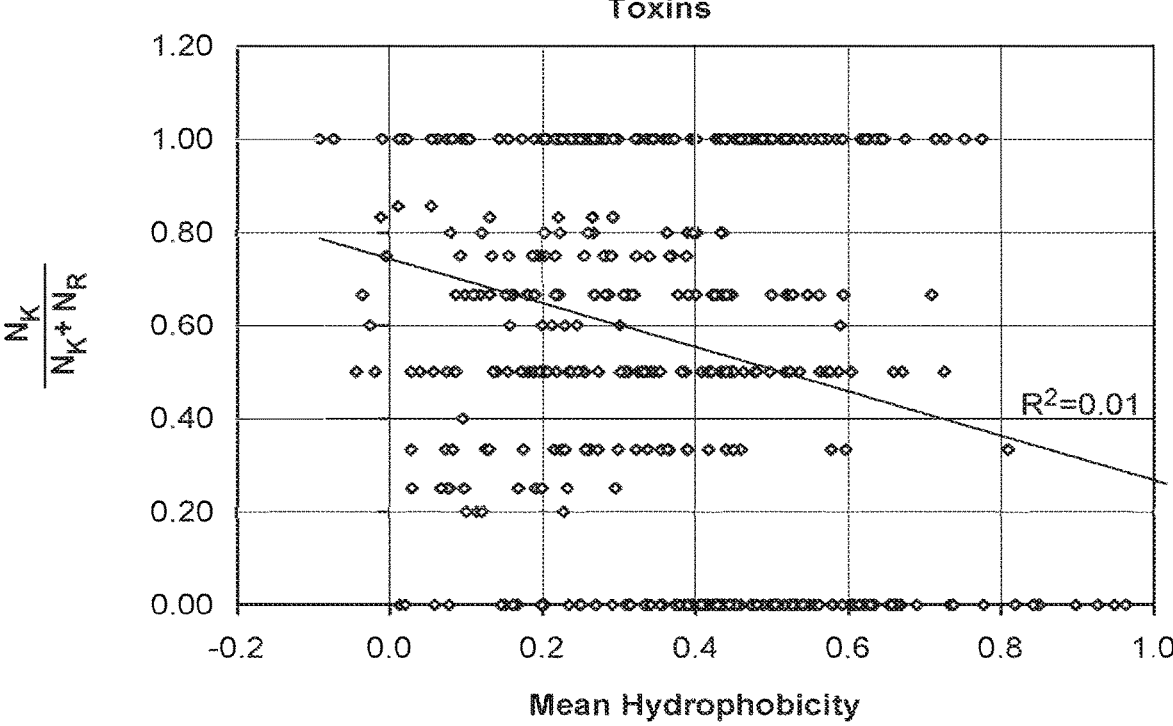

Retrieved sequences were also scored for their ratio of lysine to arginine ($N_K/N_K+N_R$) residues. Prior studies have demonstrated that the relative abundance of these residues can significantly impact the propensity of a given peptide to induce negative Gaussian curvature (NGC) in membranes, a phenomenon that is associated with pore formation and membrane permeabilization. Prior studies have demonstrated that the residue lysine is favored over arginine in AHAPs, a substitution that necessitates an increased level of peptide hydrophobicity to efficiently induce NGC. In the present example, retrieved AHAP helices largely adhered to this rule, demonstrating a modest positive association between $N_K/N_K+N_R$ ratio and peptide hydrophobicity (FIG. 6). By comparison, amphipathic helices from toxins did not comply with this observation, where a negative relationship between $N_K/N_K+N_R$ ratio and peptide hydrophobicity was found.

Application of the α-Core Sequence Formula to Retrieve Previously Uncharacterized Antimicrobial Sequences In addition to the known classes of antimicrobial proteins, the (α-core formula also retrieved many uncharacterized proteins, or proteins with an alternate primary function. Based on the efficiency with which the formula retrieved antimicrobial peptides, it was of interest to determine whether some of these additional sequences might represent: 1) as yet uncharacterized antimicrobial proteins; or 2) proteins with an assigned function that also have an as yet unidentified antimicrobial function or antimicrobial domain within a larger protein.

Figure 7:
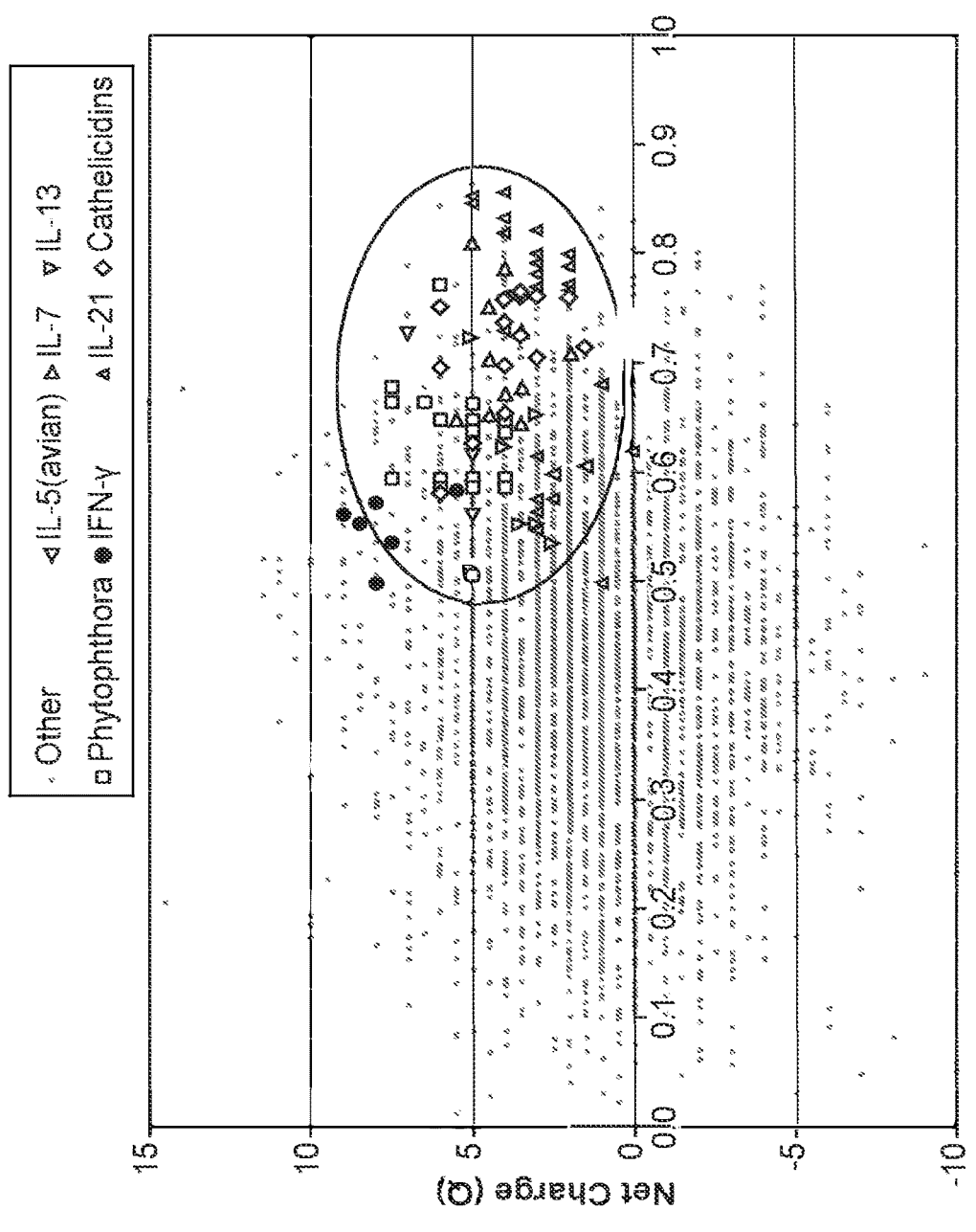
FIG. 7 shows the mapping of net charge vs. hydrophobic moment in study peptides (IL-5 (SEQ ID NO:1); IL-7 (SEQ ID NO:2); IL-13 (SEQ ID NO:3); IL-21 (SEQ ID NO:4); IFN-γ (bIFN-γ (SEQ ID NO:5); hIFN-γ (SEQ ID NO:6)); *Phytophthora* (Pp-1 (SEQ ID NO:7); Pp-2 (SEQ ID NO:8); Pp-3 (SEQ ID NO:9); Pp-4 (SEQ ID NO:10))). Values for net charge (Q) versus hydrophobic moment (H) are shown for the retrieved peptide dataset. All retrieved sequences are shown in gray. Peptide groups selected for further characterization are shown in color. For comparison, prototypic AHAPs are shown in pink.
Figure 8:
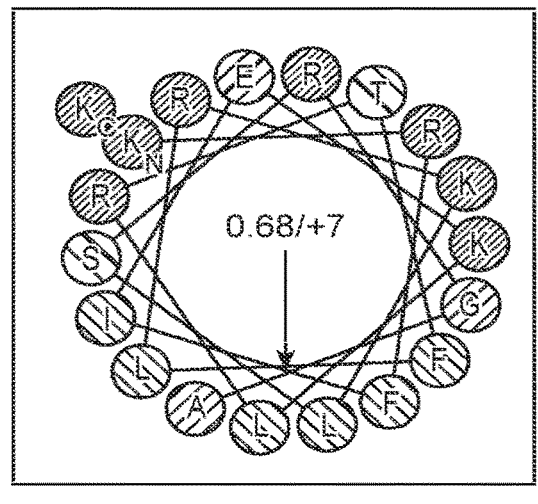
FIG. 8 shows helical wheel depiction of study test peptides (IL-5 (SEQ ID NO:1); IL-7 (SEQ ID NO:2); IL-13 (SEQ ID NO:3); IL-21 (SEQ ID NO:4); bIFN-γ (SEQ ID NO:5); hIFN-γ (SEQ ID NO:6); Pp-1 (SEQ ID NO:7); Pp-2 (SEQ ID NO:8); Pp-3 (SEQ ID NO:9); Pp-4 (SEQ ID NO:10)). Hydrophobic moment (H) and vector angle direction are indicated. Coloration: cationic full charge (KR)—blue, partial charge (H)—light blue; anionic—red; polar—yellow; tiny—gray; polar (NQ)—pink, (TS)—purple.
Figure 8:
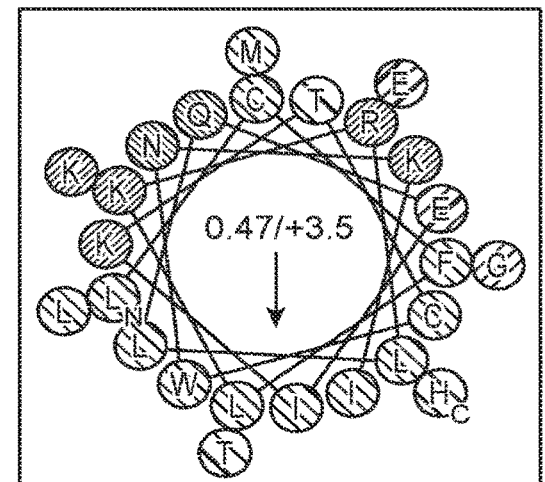
Figure 8:
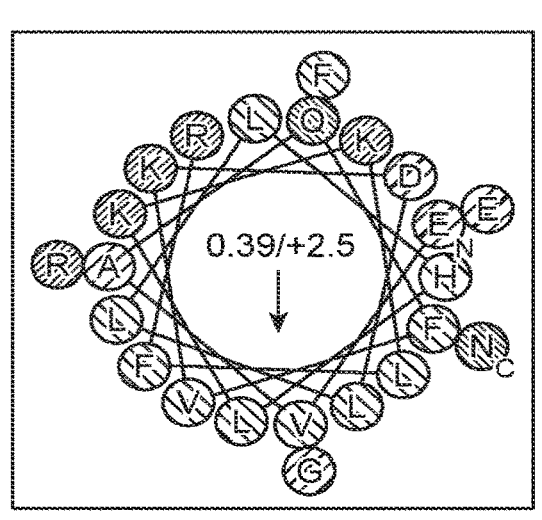
Figure 8:
Figure 8:
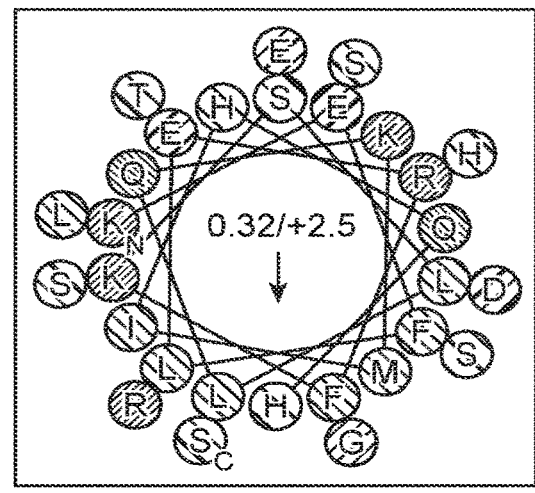
Figure 8:
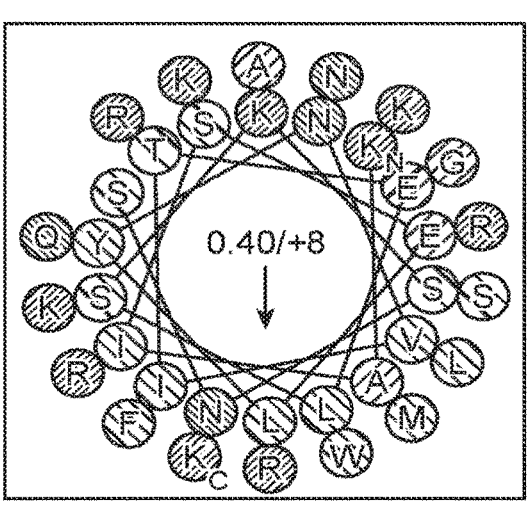
Figure 8:
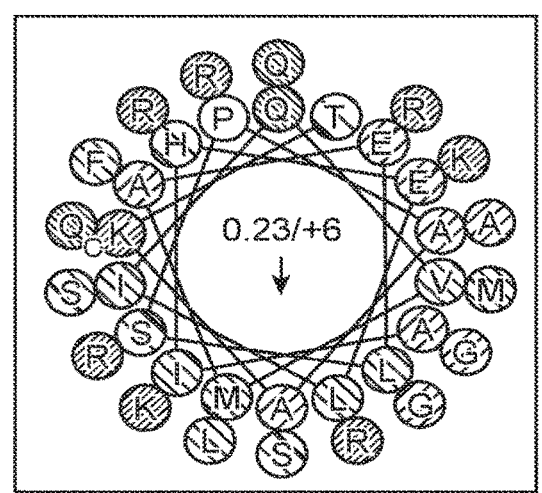
Figure 8:
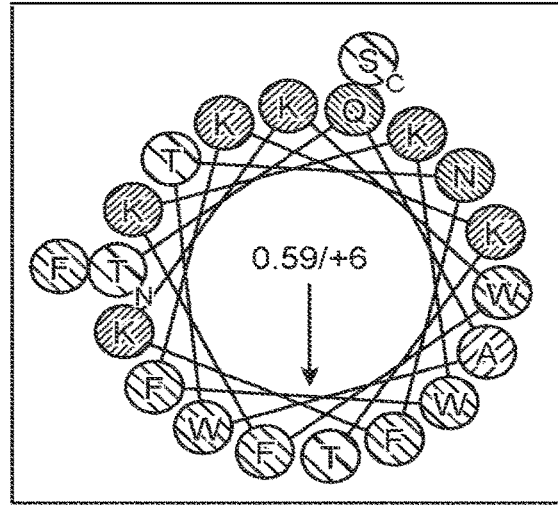
Figure 8:
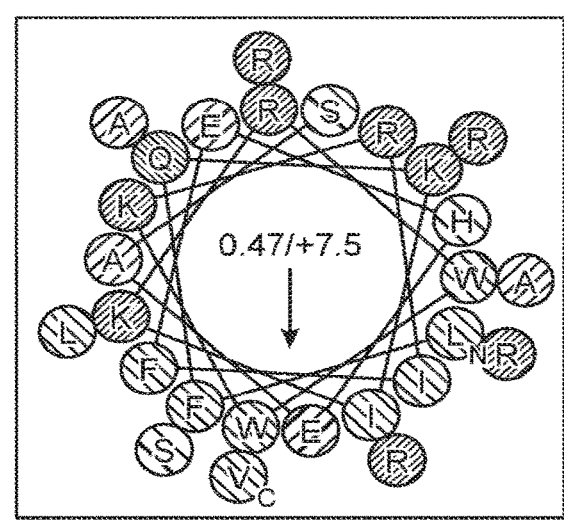
Figure 8:
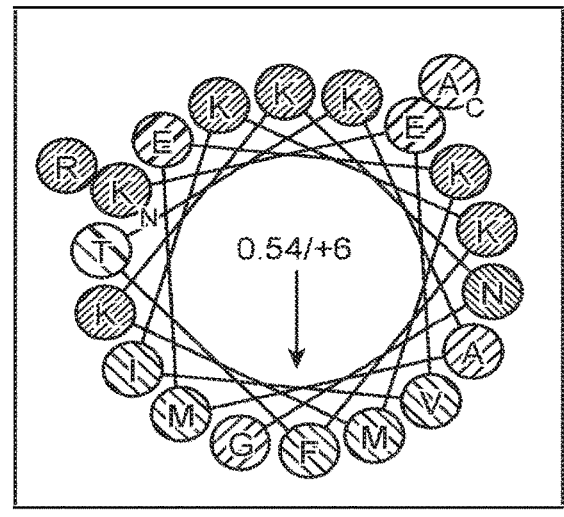
Figure 8:
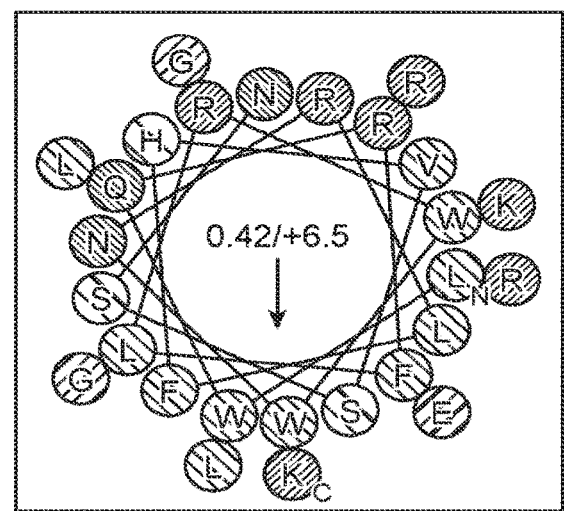

To identify putative microbicidal sequences, study set peptides were scored for the biophysical parameters described above (H, Q, H, K/K+R, PI) and analyzed to determine which factors and/or relationships were most efficient at separating known AHAPs from non-microbicidal sequences. Results from these analyses, demonstrated that mean amphipathicity (H) and either net charge (Q) (FIG. 7) or PI were the most efficient means of discriminating bonafide AHAPs from other sequences.

Based on the above analyses, dataset proteins were scored for either cationicity or PI and hydrophobic moment (Q*μH) or (PI*μH) and sequences of interest were prioritized. While this analysis retrieved many peptides of interest, several families of biological significance were consistently found amongst the top scoring sequences. These included members of the γ-chain-dependent interleukin family along with many interferon sequences. Moreover, a number of consistently high scoring peptides were also derived from the globally-impactful plant pathogen *Phytophthora parasitica.*

Given the above considerations, ten lead candidates representing these families were synthesized so that their antimicrobial properties could be determined (Table 2). As shown in Table 2, they included:

Interleukins
    IL-5—*Meleagris gallopavo* (common turkey) (SEQ ID NO:1)
    IL-7—human (SEQ ID NO:2)
    IL-13—human (SEQ ID NO:3)
    IL-21—human (SEQ ID NO:4)
Interferons
    IFN-γ—*Myotis davidii* (vesper bat) (SEQ ID NO:5)
    IFN-γ—human (SEQ ID NO:6)
*Phytophthora parasitica* uncharacterized sequences
    Pp-1—*P. parasitica* (SEQ ID NO:7)
    Pp-2—*P. parasitica* (SEQ ID NO:8)
    Pp-3—*P. parasitica* (SEQ ID NO:9)
    Pp-4—*P. parasitica* (SEQ ID NO:10)

Two additional candidates were identified when the localization of the pattern relative to the C-terminal region was relaxed. These two candidates, along with two respective longer versions are listed in Table 3. Additional listings of identified peptides are provided in Table 4, and SEQ ID NO:518-6029 (localization required) and SEQ ID NO:6030-6860 (localization requirement relaxed).

TABLE 2

Study set peptides

| Short Name | Peptide | Accession | Species | Sequence | Charge | μH | SEQ ID NO: |
|---|---|---|---|---|---|---|---|
| tIL-5 | IL-5 | G1N9U6 | *Meleagris gallopavo* | KRFIEKLRTF LRKLSRGAK | +7 | 0.68 | 1 |
| hIL7 | IL-7 | P13232 | *Homo sapiens* | LCFLKRLLQE IKTCWNKILM GTKEH | +3.5 | 0.47 | 2 |
| hIL-13 | IL-13 | P35225 | *Homo sapiens* | EVAQFVKDLL LHLKKLFREG RFN | +2.5 | 0.39 | 3 |
| hIL-21 | IL-21 | Q9HBE4 | *Homo sapiens* | KEFLERFKSL LQKMIHQHLS SRTHGSEDS | +2.5 | 0.32 | 4 |
| bIFN-γ | IFN-g | L5LME8 | *Myotis davidii* | KAISELYNVI TELSKSNSKM RKRRQNLFRG WKASK | +8 | 0.40 | 5 |
| hIFN-γ | IFN-g | P01579 | *Homo sapiens* | AIHELIQVMA ELSPAAKTGK RKRSQMLFRG RRASQ | +6 | 0.23 | 6 |
| Pp-1 | | W2QY53 | *Phytophthora parasitica* | TQAWTNFKKW FKKWFKKTFS | +6 | 0.59 | 7 |
| Pp-2 | | W2N8A5 | *Phytophthora parasitica* | LFQKIKRWWK RIFEHEASRS ARRLRAV | +7.5 | 0.47 | 8 |
| Pp-3 | | W2HTE6 | *Phytophthora parasitica* | KEVIKKFTKA MEKMKKNGRA | +6 | 0.54 | 9 |
| Pp-4 | | A0A080YYV3 | *Phytophthora parasitica* | LWQRFLRWWN RLFHVSSNRL LREGGKK | +6.5 | 0.42 | 10 |

TABLE 3

| | | | | | | | SEQ ID NO: |
|---|---|---|---|---|---|---|---|
| Peptide | Accession | Species | Sequence | Length | Charge | μH | |
| Dynorphin A (short) | P01213 | *Homo sapiens* | YGGFLRRIRP KLKWDNQ | 17 | +4 | 0.32 | 11 |
| Dynorphin (long) | P01213 | *Homo sapiens* | YGGFLRRIRP KLKWDNQKRY GGFLRRQFKV VT | 32 | +9 | 0.16 | 13 |
| Oncostatin M (short) | P13725 | *Homo sapiens* | KEFLERFKSL LQKMIHQHLS SRTHGSEDS | 29 | +2.5 | 0.32 | 12 |
| Oncostatin M (long) | P13725 | *Homo sapiens* | RFLHGYHRFM HSVGRVFSKW GESPNRSRRH SPHQALRKGV RRTRPSRKGK RLMTRGQLPR | 60 | +19.5 | 0.32 | 14 |

TABLE 4

Priority alpha core peptide sequences

| Accession # | Name | Comp Form Match | HM | Q | HM*Q | PI | SEQ ID NO: |
|---|---|---|---|---|---|---|---|
| W7G0H8 | Uncharacterized protein | RIKKFLKRCCKKIK | 0.82 | 8 | 6.52 | 6.17 | 19 |
| W4IIC4 | Uncharacterized protein | RIKKFLKRCCKKIK | 0.82 | 8 | 6.52 | 6.03 | 20 |
| A0A024W805 | Uncharacterized protein | RIKKFLKRCCKKIK | 0.82 | 8 | 6.52 | 6.03 | 21 |
| U3KN10 | Uncharacterized protein | FLKKLLQKIKTCWNKILRG IKE | 0.75 | 6 | 4.51 | 8.7 | 22 |
| A0A016VH75 | Uncharacterized protein | KRVKRFCKKACRKASQ | 0.56 | 8 | 4.47 | 9.2 | 23 |
| A0A016VGG2 | Uncharacterized protein | KRVKRFCKKACRKASQ | 0.56 | 8 | 4.47 | 9.2 | 24 |
| G1N9U6 | Uncharacterized protein | KNVKRFIEKLRTFLRKLS | 0.72 | 6 | 4.34 | 9.44 | 25 |
| Q8SUJ0 | Uncharacterized protein | LVRKIIKYCRKL | 0.86 | 5 | 4.28 | 5.53 | 26 |
| M1JIG5 | Uncharacterized protein | LVRKIIKYCRKL | 0.86 | 5 | 4.28 | 5.53 | 27 |
| T1HZ04 | Uncharacterized protein | FRRLCRNIKEVIKK | 0.85 | 5 | 4.25 | 6.15 | 28 |
| A0A080YVY9 | Uncharacterized protein | TQAWTNFKKWFKKWFKK | 0.69 | 6 | 4.13 | 9.23 | 29 |
| W2QY53 | Uncharacterized protein | TQAWTNFKKWFKKWFKK | 0.69 | 6 | 4.13 | 9.23 | 30 |
| W2W791 | Uncharacterized protein | TQAWTNFKKWFKKWFKK | 0.69 | 6 | 4.13 | 9.23 | 31 |
| W2G110 | Uncharacterized protein | TQAWTNFKKWFKKWFKK | 0.69 | 6 | 4.13 | 9.23 | 32 |
| E0AD11 | Interleukin-5 | VKKFIEKLRTFIRKL | 0.82 | 5 | 4.08 | 9.06 | 33 |
| Q5W4T8 | Interleukin-5 | VKKFIEKLRTFIRKL | 0.82 | 5 | 4.08 | 8.88 | 34 |
| F1P2P6 | Uncharacterized protein | VKKFIEKLRTFIRKL | 0.82 | 5 | 4.08 | 8.88 | 35 |

TABLE 4-continued

| | | Priority alpha core peptide sequences | | | | | |
|---|---|---|---|---|---|---|---|
| Accession # | Name | Comp Form Match | HM | Q | HM*Q | PI | SEQ ID NO: |
| A0A093FG05 | Interleukin-21 (Fragment) | KEFLKSFAKLIRKVIR | 0.80 | 5 | 4.02 | 9.54 | 36 |
| A0A094LKV9 | Interleukin-21 (Fragment) | KEFLKSFAKLIKKVIR | 0.80 | 5 | 4.01 | 9.57 | 37 |
| A0A091RQW4 | Interleukin-21 (Fragment) | KEFLKSFAKLIKKVIR | 0.80 | 5 | 4.01 | 9.49 | 38 |
| A0A091U0R6 | Interleukin-21 (Fragment) | KEFLKSFAKLIKKVIR | 0.80 | 5 | 4.01 | 9.44 | 39 |
| A0A091WDE2 | Interleukin-21 (Fragment) | KEFLKSFAKLIKKVIR | 0.80 | 5 | 4.01 | 9.37 | 40 |
| A0A091Q048 | Interleukin-21 (Fragment) | KEFLKSLAKLIKKVIR | 0.80 | 5 | 3.99 | 9.61 | 41 |
| Q32620 | Uncharacterized 3.3 kDa protein in psbT-psbN intergenic region (ORF27) | FFKWISKFIRRLSKCG | 0.79 | 5 | 3.95 | 10.74 | 42 |
| H2WTG9 | Uncharacterized protein | ANKANRMMRKIMRKL | 0.66 | 6 | 3.94 | 4.9 | 43 |
| F6W4B4 | Uncharacterized protein (Fragment) | WYQLIRTFGNLIHQKYRKL LEAYRKLR | 0.59 | 6.5 | 3.86 | 9.3 | 44 |
| P56478 | Interleukin-7 (IL-7) | FLKRLLREIKTCWNKILKG | 0.77 | 5 | 3.83 | 8.91 | 45 |
| Q544C8 | Interleukin 7 (Interleukin 7, isoform CRA_b) | FLKRLLREIKTCWNKILKG | 0.77 | 5 | 3.83 | 8.73 | 46 |
| P10168 | Interleukin-7 (IL-7) | FLKRLLREIKTCWNKILKG | 0.77 | 5 | 3.83 | 8.73 | 47 |
| A0A078IDV8 | BnaC03g69180D protein | IIKVITRALRGARRLLKY | 0.64 | 6 | 3.81 | 10.16 | 48 |
| G7MZL5 | Interleukin-7 (Fragment) | FLKRLLQKIKTCWNKIL | 0.76 | 5 | 3.79 | 9.21 | 49 |
| G7PC28 | Interleukin-7 (Fragment) | FLKRLLQKIKTCWNKIL | 0.76 | 5 | 3.79 | 9.07 | 50 |
| Q95J83 | Interleukin 7 | FLKRLLQKIKTCWNKIL | 0.76 | 5 | 3.79 | 9 | 51 |
| Q8HZN1 | Interleukin-7 | FLKRLLQKIKTCWNKIL | 0.76 | 5 | 3.79 | 9 | 52 |
| B6E124 | Interleukin-7 | FLKRLLQKIKTCWNKIL | 0.76 | 5 | 3.79 | 8.99 | 53 |
| A0A096N2Z5 | Uncharacterized protein | FLKRLLQKIKTCWNKIL | 0.76 | 5 | 3.79 | 9 | 54 |
| F7G6P7 | Uncharacterized protein (Fragment) | FLKRLLQKIKTCWNKIL | 0.76 | 5 | 3.79 | 8.81 | 55 |
| F7G6Q1 | Uncharacterized protein (Fragment) | FLKRLLQKIKTCWNKIL | 0.76 | 5 | 3.79 | 8.71 | 56 |

TABLE 4-continued

Priority alpha core peptide sequences

| Accession # | Name | Comp Form Match | HM | Q | HM*Q | PI | SEQ ID NO: |
|---|---|---|---|---|---|---|---|
| D0NCA0 | Putative uncharacterized protein | NGLFQKIKRWWKRIFDR | 0.75 | 5 | 3.73 | 10.62 | 57 |
| A0A093GP59 | Interferon alpha-2 (Fragment) | RRCLQLAHKVIRKL | 0.67 | 5.5 | 3.69 | 9.81 | 58 |
| H0Z3Q1 | Uncharacterized protein | FIKKLMTFIRKVLKT | 0.74 | 5 | 3.68 | 9.41 | 59 |
| L7NUA5 | Interleukin-7 variant 2 | FVKRLLDEIKTCWNKILRG AKK | 0.70 | 5 | 3.51 | 9.56 | 60 |
| L7NU76 | Interleukin-7 variant 5 | FVKRLLDEIKTCWNKILRG AKK | 0.70 | 5 | 3.51 | 9.48 | 61 |
| L7NU80 | Interleukin-7 variant 1 | FVKRLLDEIKTCWNKILRG AKK | 0.70 | 5 | 3.51 | 9.33 | 62 |
| L7NUC8 | Interleukin-7 variant 4 | FVKRLLDEIKTCWNKILRG AKK | 0.70 | 5 | 3.51 | 9.24 | 63 |
| L7NU82 | Interleukin-7 variant 3 | FVKRLLDEIKTCWNKILRG AKK | 0.70 | 5 | 3.51 | 9 | 64 |
| L7NU81 | Interleukin-7 variant 6 | FVKRLLDEIKTCWNKILRG AKK | 0.70 | 5 | 3.51 | 8.85 | 65 |
| H0VFS1 | Uncharacterized protein (Fragment) | FLKTLLQKIKTCWNKILRG | 0.68 | 5 | 3.40 | 9.27 | 66 |
| P48816 | Lysozyme (EC 3.2.1.17) (1,4-beta-N-acetylmuramidase) | ITKAAKCAKKIYKR | 0.56 | 6 | 3.37 | 9.06 | 67 |
| W2I7H3 | Uncharacterized protein | TQAWTNFKKWFKNWFKK | 0.67 | 5 | 3.36 | 8.34 | 68 |
| W2JZX5 | Uncharacterized protein | KEVIKKFTKAMEKMKK | 0.67 | 5 | 3.35 | 10.12 | 69 |
| W2VUY9 | Uncharacterized protein | KEVIKKFTKAMEKMKK | 0.67 | 5 | 3.35 | 10.12 | 70 |
| W2HTE6 | Uncharacterized protein | KEVIKKFTKAMEKMKK | 0.67 | 5 | 3.35 | 10.12 | 71 |
| A0A080Z0D6 | Uncharacterized protein | KEVIKKFTKAMEKMKK | 0.67 | 5 | 3.35 | 10.12 | 72 |
| W2FPC4 | Uncharacterized protein | KEVIKKFTKAMEKMKK | 0.67 | 5 | 3.35 | 9.91 | 73 |
| W2Y3P7 | Uncharacterized protein | KEVIKKFTKAMEKMKK | 0.67 | 5 | 3.35 | 9.91 | 74 |
| W2QT56 | Uncharacterized protein | KEVIKKFTKAMEKMKK | 0.67 | 5 | 3.35 | 9.91 | 75 |
| W2N8A5 | Uncharacterized protein | NGLFQKIKRWWKRIFEH | 0.74 | 4.5 | 3.34 | 10.43 | 76 |
| W2RAE5 | Uncharacterized protein | NGLFQKIKRWWKRIFEH | 0.74 | 4.5 | 3.34 | 10.43 | 77 |

TABLE 4-continued

Priority alpha core peptide sequences

| Accession # | Name | Comp Form Match | HM | Q | HM*Q | PI | SEQ ID NO: |
|---|---|---|---|---|---|---|---|
| W2WX61 | Uncharacterized protein | NGLFQKIKRWWKRIFEH | 0.74 | 4.5 | 3.34 | 10.43 | 78 |
| A0A081A496 | Uncharacterized protein | NGLFQKIKRWWKRIFEH | 0.74 | 4.5 | 3.34 | 10.31 | 79 |
| W2Z9T6 | Uncharacterized protein | NGLFQKIKRWWKRIFEH | 0.74 | 4.5 | 3.34 | 10.31 | 80 |
| P50718 | Lysozyme (EC 3.2.1.17) (1,4-beta-N-acetylmuramidase) | ITKASKCAKKIYKR | 0.55 | 6 | 3.33 | 9.15 | 81 |
| T0L7V9 | Uncharacterized protein | LWDKFQKFLKKVIRI | 0.82 | 4 | 3.30 | 6.88 | 82 |
| A0A072TQ32 | Transmembrane protein, putative | CNHMPNLLTRCLQRLKRLK | 0.60 | 5.5 | 3.28 | 10.05 | 83 |
| G7KJJ5 | Nodule Cysteine-Rich (NCR) secreted peptide | HSFYKCIDNLCKRFRR | 0.73 | 4.5 | 3.28 | 8.83 | 84 |
| A0A091WML3 | Interferon alpha-2 (Fragment) | MRRCLQLIDKVIRKL | 0.81 | 4 | 3.26 | 9.78 | 85 |
| A0A091K0Z9 | Interferon alpha-2 (Fragment) | MRRCLQLIDKVIRKL | 0.81 | 4 | 3.26 | 9.78 | 86 |
| A0A091JCY0 | Interferon epsilon (Fragment) | MRRCLQLIDKVIRKL | 0.81 | 4 | 3.26 | 9.76 | 87 |
| A0A091KMX5 | Interferon alpha-2 (Fragment) | MRRCLQLIDKVIRKL | 0.81 | 4 | 3.26 | 9.72 | 88 |
| A0A093RGB3 | Interferon alpha-2 (Fragment) | MRRCLQLIDKVIRKL | 0.81 | 4 | 3.26 | 9.63 | 89 |
| A0A091SY09 | Interferon alpha-2 (Fragment) | MRRCLQLIDKVIRKL | 0.81 | 4 | 3.26 | 9.62 | 90 |
| A0A094KQN9 | Interferon alpha-2 (Fragment) | MRRCLQLIDKVIRKL | 0.81 | 4 | 3.26 | 9.62 | 91 |
| A0A093L2W4 | Interferon alpha-2 (Fragment) | MRRCLQLIDKVIRKL | 0.81 | 4 | 3.26 | 9.6 | 92 |
| A0A093FC11 | Interferon alpha-2 (Fragment) | MRRCLQLIDKVIRKL | 0.81 | 4 | 3.26 | 9.55 | 93 |
| A0A087QSI7 | Interferon alpha-2 (Fragment) | MRRCLQLIDKVIRKL | 0.81 | 4 | 3.26 | 9.46 | 94 |
| A0A087VKA8 | Interferon omega-1 (Fragment) | MRRCLQFIDKVIRKL | 0.81 | 4 | 3.26 | 9.57 | 95 |

TABLE 4-continued

Priority alpha core peptide sequences

| Accession # | Name | Comp Form Match | HM | Q | HM*Q | PI | SEQ ID NO: |
|---|---|---|---|---|---|---|---|
| A0A091QVA3 | Interferon omega-1 (Fragment) | MRRCLQLIDKVIRKL | 0.81 | 4 | 3.26 | 9.65 | 96 |
| A0A091GAP8 | Interferon alpha-2 (Fragment) | MRRCLQLIEKVIRKL | 0.81 | 4 | 3.25 | 9.87 | 97 |
| A0A091L4R0 | Interleukin-21 (Fragment) | KEFLKSFEKLIKKVIR | 0.81 | 4 | 3.23 | 9.32 | 98 |
| A0A059BP64 | Uncharacterized protein | NLCKRACRTCCTHCRRVP | 0.59 | 5.5 | 3.22 | 8.61 | 99 |
| A0A091VJQ6 | Interferon alpha-2 (Fragment) | RRCLQLIDKVIRKL | 0.80 | 4 | 3.19 | 9.7 | 100 |
| A5JYR0 | Protein CO6C3.10 | YARRFSTLFRHLIKMI | 0.71 | 4.5 | 3.18 | 11.56 | 101 |
| A0A091JU23 | Interleukin-21 (Fragment) | REFLKSFAKLIKKVI | 0.79 | 4 | 3.16 | 9.41 | 102 |
| A0A093IE23 | Interferon alpha-2 (Fragment) | MRRCLQLIDKVMRKL | 0.79 | 4 | 3.16 | 9.65 | 103 |
| A0A091P9G9 | Interferon alpha-2 (Fragment) | MRRCLQLIDKVVRKL | 0.79 | 4 | 3.16 | 9.76 | 104 |
| A0A091U5M0 | Interferon alpha-2 (Fragment) | MRRCLQLIDKAIRKI | 0.79 | 4 | 3.14 | 9.65 | 105 |
| A0A093BUH7 | Interferon epsilon (Fragment) | MRRCLQLIDKAIRKL | 0.78 | 4 | 3.11 | 9.33 | 106 |
| A0A094KTL8 | Interferon alpha-2 (Fragment) | MRRCLQLIDKAIKKL | 0.78 | 4 | 3.11 | 9.55 | 107 |
| A0A091SBM1 | Interferon beta (Fragment) | MRRCLQLVDKVIRKL | 0.78 | 4 | 3.11 | 9.61 | 108 |
| A0A093HSG6 | Interferon alpha-2 (Fragment) | MRRCLQFVDKVIKRL | 0.78 | 4 | 3.10 | 9.49 | 109 |
| A0A091HDU2 | Interferon alpha-2 (Fragment) | MRRCLQLVDKVIRKL | 0.78 | 4 | 3.10 | 9.72 | 110 |
| G1PT51 | Uncharacterized protein | VKKAVKYLRTIMKS | 0.62 | 5 | 3.10 | 9.96 | 111 |
| A0A091UC07 | Interleukin-21 (Fragment) | KEFLKSFAKLIKQVIR | 0.78 | 4 | 3.10 | 9.61 | 112 |
| A0A094K224 | Interleukin-21 (Fragment) | KEFLKSFAKLIKQVIR | 0.78 | 4 | 3.10 | 9.54 | 113 |
| A0A093IDB2 | Interleukin-21 (Fragment) | KEFLKSFAKLIKQVIR | 0.78 | 4 | 3.10 | 9.52 | 114 |
| A0A091VRY9 | Interleukin-21 (Fragment) | KEFLKSFAKLIKQVIR | 0.78 | 4 | 3.10 | 9.46 | 115 |

TABLE 4-continued

Priority alpha core peptide sequences

| Accession # | Name | Comp Form Match | HM | Q | HM*Q | PI | SEQ ID NO: |
|---|---|---|---|---|---|---|---|
| O95399 | Urotensin-2 (Urotensin II) (U-II) (UII) | LSHLLARIWKPYKK | 0.68 | 4.5 | 3.05 | 4.37 | 116 |
| M7W4U4 | Lecithin: cholesterol acyltransferase family protein (Fragment) | LSIFAKCFHDLIKKFKKLG | 0.68 | 4.5 | 3.04 | 4.45 | 117 |
| A0A091M384 | Interferon omega-1 (Fragment) | MRRCLQLIDKVARKL | 0.75 | 4 | 3.01 | 9.62 | 118 |
| Q8HYR8 | IL-7 | LLQKIKTCWNKILRGIKE | 0.75 | 4 | 3.01 | 9.04 | 119 |
| L8IFQ4 | Interleukin-7 (Fragment) | LLQKIKTCWNKILRGIKE | 0.75 | 4 | 3.01 | 9.02 | 120 |
| P26895 | Interleukin-7 (IL-7) | LLQKIKTCWNKILRGIKE | 0.75 | 4 | 3.01 | 9.02 | 121 |
| P01588 | Erythropoietin (Epoetin) | FRKLFRVYSNFLRG | 0.75 | 4 | 3.00 | 8.75 | 122 |
| Q91Y32 | Interleukin-7 | FLKRLLREIKTCWNKILNS | 0.74 | 4 | 2.98 | 8.75 | 123 |
| R0LJN1 | Interferon alpha-2 (Fragment) | IRRCLQLIDKAVRKLY | 0.74 | 4 | 2.97 | 9.5 | 124 |
| A0A044QPZ9 | Uncharacterized protein | NFLSLIKKIFSVWKR | 0.74 | 4 | 2.96 | 8.47 | 125 |
| F7BPI0 | Uncharacterized protein | KIMRKIMTNLSRLC | 0.74 | 4 | 2.95 | 10.06 | 126 |
| A0A093EX75 | Interleukin-21 | KEFLKSFAKLIQKVIKS | 0.72 | 4 | 2.90 | 9.28 | 127 |
| A0A091E7E9 | Interleukin-5 (Fragment) | FIKKLMTFIQKVLKN | 0.72 | 4 | 2.88 | 9.13 | 128 |
| P0DKN3 | Turripeptide Lol11.2 (OL67) | RDAGRLLRSLKKLK | 0.57 | 5 | 2.87 | 8.7 | 129 |
| A0A091LVZ3 | Uncharacterized protein | KNATTFIKKLMTFIRKA | 0.57 | 5 | 2.84 | 9.2 | 130 |
| S9YX13 | Olfactory receptor 4A15 | GEMKNAMKKLWTRVRK | 0.57 | 5 | 2.83 | 9.46 | 131 |
| V9DV74 | Uncharacterized protein | TQAWTNFKKWFKKWFKE | 0.69 | 4 | 2.74 | 8.34 | 132 |
| W2KE58 | Uncharacterized protein | TQAWTNFKKWFKKWFKE | 0.69 | 4 | 2.74 | 8.34 | 133 |
| L8YAP6 | Interleukin-13 | EVAQFVKDLLRHLKRLYRH | 0.68 | 4 | 2.73 | 8.97 | 134 |
| Q6UXQ8 | Putative uncharacterized protein UNQ6190/PRO20217 | GAGRKVCAKLVKRL | 0.55 | 5 | 2.73 | 11.8 | 135 |
| U6CRU1 | Interleukin-7 | LLQKIKTCWNKILRGS | 0.68 | 4 | 2.71 | 9.03 | 136 |

TABLE 4-continued

Priority alpha core peptide sequences

| Accession # | Name | Comp Form Match | HM | Q | HM*Q | PI | SEQ ID NO: |
|---|---|---|---|---|---|---|---|
| D2HR10 | Putative uncharacterized protein (Fragment) | LLQKIKTCWNKILRGS | 0.68 | 4 | 2.71 | 9.7 | 137 |
| M3W2P1 | Uncharacterized protein | LLQKIKTCWNKILRGS | 0.68 | 4 | 2.71 | 9.15 | 138 |
| M4CA57 | Uncharacterized protein | NFIKRINDFLKKAKS | 0.67 | 4 | 2.69 | 9.89 | 139 |
| P13725 | Oncostatin-M (OSM) | RFLHGYHRFMHSVGRVFSK WGES | 0.60 | 4.5 | 2.69 | 10.6 | 140 |
| U5TZM0 | Interleukin-7 | LLQKIKTCWNKILRGAKEY | 0.67 | 4 | 2.68 | 8.85 | 141 |
| Q9N2G6 | Interleukin-7 (IL-7) | LLQKIKTCWNKILRGAKEY | 0.67 | 4 | 2.68 | 8.7 | 142 |
| K7GL89 | Uncharacterized protein | LLQKIKTCWNKILRGAKEY | 0.67 | 4 | 2.68 | 7.77 | 143 |
| K7GL01 | Uncharacterized protein (Fragment) | LLQKIKTCWNKILRGAKEY | 0.67 | 4 | 2.68 | 7.74 | 144 |
| A0A093PT39 | Interleukin-5 (Fragment) | FINKLMTFIRKALKP | 0.66 | 4 | 2.65 | 9.3 | 145 |
| Q91ZL2 | Interleukin 4 | LKDFLKSLKRIM | 0.88 | 3 | 2.64 | 9.27 | 146 |
| P81278 | Prolactin-releasing peptide (PrRP) (Prolactin-releasing hormone) [Cleaved into: Prolactin-releasing peptide PrRP31; Prolactin-releasing peptide PrRP20] | GRGIRPVGRFGRR | 0.53 | 5 | 2.63 | 11.42 | 147 |
| A0A080YYV3 | Uncharacterized protein | NGLWQRFLRWWNRLFH | 0.75 | 3.5 | 2.62 | 9.86 | 148 |
| W2VQZ9 | Uncharacterized protein | NGLWQRFLRWWNRLFH | 0.75 | 3.5 | 2.62 | 9.86 | 149 |
| W2PXT4 | Uncharacterized protein | NGLWQRFLRWWNRLFH | 0.75 | 3.5 | 2.62 | 9.69 | 150 |
| P86442 | Neuropeptide F (Lom-NPF) (NPF) (longNPF) | SADKFWRRFARR | 0.66 | 4 | 2.62 | 10.84 | 151 |
| B8BP19 | Putative uncharacterized protein | WSRWWSSCWRLWTRIY | 0.87 | 3 | 2.61 | 4.85 | 152 |
| W2ZYU4 | Uncharacterized protein | YLKEALSRFKSWLKR | 0.65 | 4 | 2.60 | 10.07 | 153 |

TABLE 4-continued

| | | Priority alpha core peptide sequences | | | | | |
|---|---|---|---|---|---|---|---|
| Accession # | Name | Comp Form Match | HM | Q | HM*Q | PI | SEQ ID NO: |
| Q9XTN0 | Peptidoglycan recognition protein | SPGRKLYNQIRRWP | 0.65 | 4 | 2.59 | 6.71 | 154 |
| X6P0L4 | Uncharacterized protein | KYGKSCEKAVHDLWHIIKK F | 0.64 | 4 | 2.58 | 8.2 | 155 |
| P24355 | 50S ribosomal protein L36, plastid | KVYSSVRKICKSCG | 0.64 | 4 | 2.57 | 11.06 | 156 |
| W2YJS0 | Uncharacterized protein | TQAWTNFKKWFKKMV | 0.64 | 4 | 2.55 | 5.08 | 157 |
| Q9BBQ2 | 50S ribosomal protein L36, chloroplastic | KIGASVRKICEKCR | 0.64 | 4 | 2.55 | 11.79 | 158 |
| W2HIB3 | Uncharacterized protein | GGGRDVLTRFKSWFKRVFG K | 0.50 | 5 | 2.52 | 8.39 | 159 |
| P50717 | Lysozyme (EC 3.2.1.17) (1,4-beta-N-acetylmuramidase) | ITKASTCAKKIFKR | 0.50 | 5 | 2.52 | 8.92 | 160 |
| A0A094LD69 | Uncharacterized protein (Fragment) | FIEKLMTFIRKALKNAR | 0.63 | 4 | 2.51 | 9.3 | 161 |
| Q6UXT8 | Protein FAM 150A | AYYKRCARLLTRLA | 0.63 | 4 | 2.51 | 10.39 | 162 |
| Q4RU86 | Protein FAM150-like | AYYKRCARLLTRLA | 0.63 | 4 | 2.51 | 9.98 | 163 |
| I7GA36 | Macaca fascicularis brain cDNA clone: QtrA-18967, similar to human HSPCO39 protein (HSPC039), mRNA, RefSeq: NM_ 016097.2 | SQLRNLIRSVRTVMR | 0.62 | 4 | 2.49 | 8.59 | 164 |
| A0A093IPB5 | Interleukin-5 (Fragment) | KNATKFIEKLMTFIRRA | 0.62 | 4 | 2.48 | 9.2 | 165 |
| P81277 | Prolactin-releasing peptide (PrRP) (Prolactin-releasing hormone) [Cleaved into: Prolactin-releasing peptide | YASRGIRPVGRFGRR | 0.49 | 5 | 2.45 | 11.6 | 166 |

TABLE 4-continued

| | | Priority alpha core peptide sequences | | | | | |
|---|---|---|---|---|---|---|---|
| Accession # | Name | Comp Form Match | HM | Q | HM*Q | PI | SEQ ID NO: |
| | PrRP31; Prolactin-releasing peptide PrRP20] | | | | | | |
| P01574 | Interferon beta (IFN-beta) (Fibroblast interferon) | HLKRYYGRILHYLKA | 0.49 | 5 | 2.45 | 8.9 | 167 |
| Q80UG6 | Protein FAM150B | TIPAYYKRCARLLTRLA | 0.61 | 4 | 2.44 | 9.57 | 168 |
| B2RZ42 | Protein FAM150B | TIPAYYKRCARLLTRLA | 0.61 | 4 | 2.44 | 9.57 | 169 |
| Q6UX46 | Protein FAM150B | TIPAYYKRCARLLTRLA | 0.61 | 4 | 2.44 | 9.37 | 170 |
| P55897 | Histone H2A [Cleaved into: Buforin-1 (Buforin I); Buforin-2 (Buforin II)] (Fragment) | VGRVHRLLRKGN | 0.54 | 4.5 | 2.43 | 12.41 | 171 |
| P07815 | 50S ribosomal protein L36, chloroplastic | KVAASVRKICEKCR | 0.61 | 4 | 2.42 | 11.64 | 172 |
| Q95PE0 | Putative uncharacterized protein (Fragment) | IRKIAQLLNKVADAAKKG | 0.60 | 4 | 2.41 | 4.94 | 173 |
| Q2V364 | Putative defensin-like protein 23 | GGFCKRFAGGAKKCH | 0.54 | 4.5 | 2.41 | 9.14 | 174 |
| Q3E7A6 | Uncharacterized protein YML007C-A, mitochondrial | MRFMRRLVRNLQY | 0.60 | 4 | 2.40 | 12.18 | 175 |
| P04567 | Mast cell degranulating peptide (MCD peptide) (MCDP) | LPGFIGKICRKI | 0.80 | 3 | 2.39 | 9.5 | 176 |
| Q3E821 | Uncharacterized protein YBL008W-A | ILANIHKIIKAYQR | 0.68 | 3.5 | 2.38 | 11.19 | 177 |
| K4A4B8 | Uncharacterized protein | IFHGCKKVARVL | 0.68 | 3.5 | 2.37 | 9.19 | 178 |
| P01210 | Proenkephalin-A [Cleaved into: | LAKRYGGFMKRYGGFMKKM DELY | 0.58 | 4 | 2.34 | 5.3 | 179 |

47 48

TABLE 4-continued

Priority alpha core peptide sequences

| Accession # | Name | Comp Form Match | HM | Q | HM*Q | PI | SEQ ID NO: |
|---|---|---|---|---|---|---|---|
| | Synenkephalin; Met-enkephalin (Opioid growth factor) (OGF); PENK(114-133); PENK(143-183); Met-enkephalin-Arg-Gly-Leu; Leu-enkephalin; PENK(237-258); Met-enkephalin-Arg-Phe] | | | | | | |
| A0A085MM52 | Uncharacterized protein | QAIRCMQSLFRTVKR | 0.58 | 4 | 2.33 | 9.45 | 180 |
| Q8N729 | Neuropeptide W (Preproprotein L8) (hPPL8) [Cleaved into: Neuropeptide W-23 (NPW23) (hL8); Neuropeptide W-30 (NPW30) (hL8C)] | WRRALRAAAGPLAR | 0.58 | 4 | 2.33 | 11.4 | 181 |
| R0MAQ4 | NUDIX hydrolase | IKRIIRDVKEIVRA | 0.77 | 3 | 2.32 | 6.92 | 182 |
| A0A093C1K6 | Interleukin-21 (Fragment) | KEFLKSFEKLIQKVIR | 0.77 | 3 | 2.32 | 9.21 | 183 |
| R0M641 | Uncharacterized protein | EKVSNWWKRIWEKIKN | 0.77 | 3 | 2.31 | 5.8 | 184 |
| R0M5R6 | Uncharacterized protein | EKVSNWWKRIWEKIKN | 0.77 | 3 | 2.31 | 5.8 | 185 |
| M4BXP7 | Uncharacterized protein | IPSCVTRALSRAARSIWDALKKI | 0.58 | 4 | 2.31 | 9.89 | 186 |
| Q9NRR1 | Cytokine-like protein 1 (Protein C17) | ARKLYTIMNSFCRR | 0.58 | 4 | 2.31 | 8.22 | 187 |
| P81447 | Glycosylation-dependent cell adhesion molecule 1 (GlyCAM-1) (28 kDa milk glycoprotein PP3) (Lactophorin) (Proteose-peptone component 3) (PP3) | GKLMELGHKIMKNLENTVKEIIKYLKSLF | 0.66 | 3.5 | 2.29 | 5.13 | 188 |
| K7GRI1 | Interleukin | KPIKEFLERLKSLIQKMIHQ | 0.65 | 3.5 | 2.27 | 9.39 | 189 |

TABLE 4-continued

Priority alpha core peptide sequences

| Accession # | Name | Comp Form Match | HM | Q | HM*Q | PI | SEQ ID NO: |
|---|---|---|---|---|---|---|---|
| F1RQN2 | Interleukin | KPIKEFLERLKSLIQKMIH Q | 0.65 | 3.5 | 2.27 | 9.39 | 190 |
| Q76LU6 | Interleukin-21 (IL-21) | KPIKEFLERLKSLIQKMIH Q | 0.65 | 3.5 | 2.27 | 9.25 | 191 |
| A0A093G4B0 | Interleukin-21 (Fragment) | KEFLKSFAKLIQKVI | 0.76 | 3 | 2.27 | 9.49 | 192 |
| A0A091LQM6 | Interleukin-21 (Fragment) | KEFLKSFAKLIQKVI | 0.76 | 3 | 2.27 | 9.22 | 193 |
| Q09GK2 | C-type natriuretic peptide (CNP) | RRLKGVAKKGLG | 0.45 | 5 | 2.27 | 8.9 | 194 |
| H2QWB6 | Interleukin 7 (Uncharacterized protein) | FLKRLLQEIKTCWNKIL | 0.75 | 3 | 2.26 | 8.72 | 195 |
| P13232 | Interleukin-7 (IL-7) | FLKRLLQEIKTCWNKIL | 0.75 | 3 | 2.26 | 8.72 | 196 |
| Q5FBX5 | IL7 nirs variant 1 (Interleukin-7) | FLKRLLQEIKTCWNKIL | 0.75 | 3 | 2.26 | 6.14 | 197 |
| A8K673 | cDNAFLJ75417, highly similar to *Homo sapiens* interleukin 7, mRNA | FLKRLLQEIKTCWNKIL | 0.75 | 3 | 2.26 | 8.72 | 198 |
| H2PQM2 | Uncharacterized protein | FLKRLLQEIKTCWNKIL | 0.75 | 3 | 2.26 | 8.72 | 199 |
| G1QNL2 | Uncharacterized protein | FLKRLLQEIKTCWNKIL | 0.75 | 3 | 2.26 | 8.72 | 200 |
| G3QDY6 | Uncharacterized protein | FLKRLLQEIKTCWNKIL | 0.75 | 3 | 2.26 | 7.75 | 201 |
| F6TDR4 | Interleukin | KPLKEFLERLKSLIQKMIH Q | 0.64 | 3.5 | 2.26 | 9.66 | 202 |
| A0A093EHY0 | Interleukin-21 (Fragment) | KEFLKSFANLIKQVIR | 0.75 | 3 | 2.26 | 9.1 | 203 |
| L8I6N0 | Glycosylation-dependent cell adhesion molecule 1 | GKLMELGHKIMRNLENTVK ETIKYL KSLFSHASEWK | 0.56 | 4 | 2.25 | 5.98 | 204 |
| G3KFL3 | PexRD2 | HKMKKLLRYLNY | 0.50 | 4.5 | 2.24 | 9.52 | 205 |
| Q0ZCA0 | Putative accessory gland protein (Fragment) | KSFSSICKELCKLCQRC | 0.75 | 3 | 2.24 | 8.7 | 206 |

TABLE 4-continued

Priority alpha core peptide sequences

| Accession # | Name | Comp Form Match | HM | Q | HM*Q | PI | SEQ ID NO: |
|---|---|---|---|---|---|---|---|
| Q0ZC97 | Putative accessory gland protein (Fragment) | KSFSSICKELCKLCQRC | 0.75 | 3 | 2.24 | 8.64 | 207 |
| A0A091H9P3 | Interleukin-21 (Fragment) | KEFLQSFGKLINKVIR | 0.74 | 3 | 2.23 | 9.49 | 208 |
| A0A091V0J9 | Myelomonocytic growth factor (Fragment) | ILANFQRFLETAYRALRHL AR | 0.64 | 3.5 | 2.22 | 5.67 | 209 |
| A0A091J8M6 | Interleukin-21 (Fragment) | KEFLKSFAKLIQQVIR | 0.74 | 3 | 2.22 | 9.54 | 210 |
| A0A091K4W3 | Interleukin-21 (Fragment) | KEFLKSFAKLIQQVIR | 0.74 | 3 | 2.22 | 9.39 | 211 |
| A0A093PBX6 | Interleukin-21 (Fragment) | KEFLKSFAKLIQQVIR | 0.74 | 3 | 2.22 | 9.34 | 212 |
| A0A091SVN6 | Interleukin-21 (Fragment) | KEFLKSFAKLIQQVIR | 0.74 | 3 | 2.22 | 9.32 | 213 |
| U3IH11 | Interleukin | KEFLQSFSKLMKKV | 0.74 | 3 | 2.22 | 9.37 | 214 |
| A0A078J1N0 | BnaC02g44190D protein | KPLHTMVNHISRFATKMT | 0.55 | 4 | 2.21 | 4.97 | 215 |
| B3NKZ6 | Protein Turandot E (Protein Victoria) | GGKLFDVLKKIIKVI | 0.74 | 3 | 2.21 | 9.62 | 216 |
| A0A087VKZ4 | Interleukin-21 (Fragment) | KEFLQSFAKLIKQVIR | 0.73 | 3 | 2.19 | 9.34 | 217 |
| Q28540 | Interleukin-7 (IL-7) | LLQKIKTCWNKILRGITE | 0.73 | 3 | 2.19 | 8.89 | 218 |
| B9HA59 | Uncharacterized protein | RIRDVFSSIFRNIFNLFR | 0.73 | 3 | 2.19 | 10.7 | 219 |
| B6E474 | 8 kDa glycoprotein | QKIAQLVKKWIKTVLEAR | 0.54 | 4 | 2.17 | 9.78 | 220 |
| P80195 | Glycosylation-dependent cell adhesion molecule 1 (GlyCAM-1) (28 kDa milk glycoprotein PP3) (Lactophorin) (Proteose-peptone component 3) (PP3) | GKLMELGHKIMRNLENTVK ETIKYLKSLFSHAFEVVKT | 0.54 | 4 | 2.15 | 5.98 | 221 |
| S7MSM8 | Interleukin-13 | EVTRLAKDLLQQLRKGVRQ GK | 0.54 | 4 | 2.15 | 9.4 | 222 |
| L5M5Z7 | Interleukin-13 | EVTRLAKDLLQQLRKGVRQ GK | 0.54 | 4 | 2.15 | 9.1 | 223 |

TABLE 4-continued

| | | Priority alpha core peptide sequences | | | | | |
|---|---|---|---|---|---|---|---|
| Accession # | Name | Comp Form Match | HM | Q | HM*Q | PI | SEQ ID NO: |
| P0CY42 | ATP synthase protein 8 (A6L) (F-ATPase subunit 8) | LPRLLRTYISRI | 0.71 | 3 | 2.14 | 10.28 | 224 |
| P0CY41 | ATP synthase protein 8 (A6L) (F-ATPase subunit 8) | LPRLLRTYISRI | 0.71 | 3 | 2.14 | 10.28 | 225 |
| K0KI76 | Putative secreted protein | LKKLNQIVQKFHQLLQG | 0.61 | 3.5 | 2.14 | 4.85 | 226 |
| T1PF69 | Dynein heavy chain and region D6 of dynein motor | DFKNLIRKCVDVARKV | 0.71 | 3 | 2.14 | 8.71 | 227 |
| W2HGG0 | Uncharacterized protein | NATTYLKEALSRFKSWLKR | 0.53 | 4 | 2.13 | 10.07 | 228 |
| V9FSC7 | Uncharacterized protein | NATTYLKEALSRFKSWLKR | 0.53 | 4 | 2.13 | 10.07 | 229 |
| A0A081AW62 | Uncharacterized protein | NATTYLKEALSRFKSWLKR | 0.53 | 4 | 2.13 | 9.98 | 230 |
| P36925 | Interleukin-8 (IL-8) (C-X-C motif chemokine 8) (Chemokine (C-X-C motif) ligand 8) | KWVQKVVQAFLKRAEK | 0.53 | 4 | 2.12 | 9.03 | 231 |
| K7FKJ3 | Uncharacterized protein | ARKMVTRALRALQN | 0.53 | 4 | 2.12 | 8.24 | 232 |
| F7I3A3 | Interleukin | KEFLERFKSLLQKMIHR | 0.60 | 3.5 | 2.11 | 9.25 | 233 |
| Q9TJR5 | 50S ribosomal protein L32, plastid | AKKALAKAKTVLK | 0.42 | 5 | 2.10 | 11.45 | 234 |
| W2IIM7 | Uncharacterized protein | NGLWQRFLRWWNRLFTG | 0.70 | 3 | 2.10 | 10.1 | 235 |
| W2VQV4 | Uncharacterized protein | NGLWQRFLRWWNRLFTG | 0.70 | 3 | 2.10 | 10.1 | 236 |
| V9EMI9 | Uncharacterized protein | NGLWQRFLRWWNRLFTG | 0.70 | 3 | 2.10 | 10.1 | 237 |

TABLE 4-continued

Priority alpha core peptide sequences

| Accession # | Name | Comp Form Match | HM | Q | HM*Q | PI | SEQ ID NO: |
|---|---|---|---|---|---|---|---|
| D0N532 | Putative uncharacterized protein | ATKLSDAMQRIKTMFRNWYQK | 0.52 | 4 | 2.09 | 10.19 | 238 |
| P46690 | Gibberellin-regulated protein 4 (GAST1 protein *homolog* 4) | CITFCNKCCRKCL | 0.70 | 3 | 2.09 | 9.42 | 239 |
| C5YGU9 | Putative uncharacterized protein Sb07g003410 | CCDLIRKCWHDIKECWKRC | 0.83 | 2.5 | 2.08 | 9.02 | 240 |
| Q9GKA2 | Erythropoietin | KLFRIYSNFLRG | 0.69 | 3 | 2.08 | 8.89 | 241 |
| Q6H8T1 | Erythropoietin | KLFRIYSNFLRG | 0.69 | 3 | 2.08 | 8.74 | 242 |
| Q6H8S9 | Erythropoietin | KLFRIYSNFLRG | 0.69 | 3 | 2.08 | 8.74 | 243 |
| Q6H8T0 | Erythropoietin | KLFRIYSNFLRG | 0.69 | 3 | 2.08 | 8.74 | 244 |
| P33708 | Erythropoietin | KLFRIYSNFLRG | 0.69 | 3 | 2.08 | 8.68 | 245 |
| Q6H8T2 | Erythropoietin | KLFRIYSNFLRG | 0.69 | 3 | 2.08 | 8.42 | 246 |
| Q867B1 | Erythropoietin | KLFRIYSNFLRG | 0.69 | 3 | 2.08 | 8.35 | 247 |
| D7KU31 | Putative uncharacterized protein | EKFESCMKKCSKICNK | 0.69 | 3 | 2.08 | 6.62 | 248 |
| Q0Z956 | Erythropoietin | KLFRVYSNFLRG | 0.69 | 3 | 2.08 | 9.03 | 249 |
| P29676 | Erythropoietin | KLFRVYSNFLRG | 0.69 | 3 | 2.08 | 8.73 | 250 |
| Q28513 | Erythropoietin | KLFRVYSNFLRG | 0.69 | 3 | 2.08 | 8.35 | 251 |
| P07865 | Erythropoietin | KLFRVYSNFLRG | 0.69 | 3 | 2.08 | 8.35 | 252 |
| P38215 | Putative uncharacterized protein YBR013C | RKLYHRVGTCIQNIF | 0.59 | 3.5 | 2.07 | 6.07 | 253 |
| P06759 | Apolipoprotein C-III (Apo-CIII) (ApoC-III) (Apolipoprotein C3) | FKSLKGYWSKFT | 0.69 | 3 | 2.07 | 4.36 | 254 |
| B1GVZ6 | Interleukin 7 | ISSLRSCWNKFEKIISR | 0.69 | 3 | 2.06 | 8.91 | 255 |
| A8MRM1 | Protein RALF-like 16 | VNHYHRGCEKITRCARDAARY | 0.51 | 4 | 2.06 | 8.45 | 256 |
| U3K1R5 | Uncharacterized protein | ISSLRSCWNKFEKLISR | 0.69 | 3 | 2.06 | 8.91 | 257 |
| R4WCP1 | Cysteine rich secreted protein | CCRKVVKYWTHCCQEGLRCT | 0.59 | 3.5 | 2.06 | 8.72 | 258 |
| C1MNQ9 | Predicted protein | GRTFRSCARTAFRTAKL | 0.41 | 5 | 2.05 | 6.79 | 259 |
| P07321 | Erythropoietin | KLFRVYANFLRG | 0.68 | 3 | 2.05 | 7.87 | 260 |

TABLE 4-continued

| | | Priority alpha core peptide sequences | | | | | |
|---|---|---|---|---|---|---|---|
| Accession # | Name | Comp Form Match | HM | Q | HM*Q | PI | SEQ ID NO: |
| A0A061DMT2 | Uncharacterized protein | YGRGCRRCCSYL | 0.68 | 3 | 2.05 | 7.78 | 261 |
| F6PXB2 | Uncharacterized protein | FLKRLLQEIKTCWNKILSG | 0.68 | 3 | 2.03 | 8.71 | 262 |
| F6PXS2 | Uncharacterized protein (Fragment) | FLKRLLQEIKTCWNKILSG | 0.68 | 3 | 2.03 | 6.91 | 263 |
| F6PXG8 | Uncharacterized protein (Fragment) | FLKRLLQEIKTCWNKILSG | 0.68 | 3 | 2.03 | 5.68 | 264 |
| A0A094ICS8 | Uncharacterized protein | SVARHAARDLRRWM | 0.58 | 3.5 | 2.01 | 9.67 | 265 |
| F6U832 | Uncharacterized protein | LLQKIKTCWNKILRDAKE | 0.67 | 3 | 2.01 | 8.7 | 266 |
| P09641 | Peptide YY-like (PYY) | WAKYHAAVRHYVNLITR | 0.50 | 4 | 2.01 | 8.39 | 267 |
| P81028 | Peptide YY-like (PYY) | WAKYHAAVRHYVNLITR | 0.50 | 4 | 2.01 | 8.35 | 268 |
| G3VIZ8 | Uncharacterized protein | EEVFKKFKKVAKSFG | 0.67 | 3 | 2.01 | 7.83 | 269 |
| O61466 | FMRFamide-like neuropeptides 5 [Cleaved into: APKPKFIRF-amide; AGAKFIRF-amide; GAKFIRF-amide] | FGRAGAKFIRFGRS | 0.50 | 4 | 2.00 | 11.17 | 270 |
| C4V9A1 | Putative uncharacterized protein | DLKTLFTTIWKFIKK | 0.67 | 3 | 2.00 | 6.31 | 271 |
| P86730 | Perlwapin (Fragment) | KKCCGGCPRLCEK | 0.67 | 3 | 2.00 | 8.45 | 272 |
| A8MQM7 | Protein RALF-like 15 | KQVANPYRRGCGTIERCR | 0.49 | 4 | 1.97 | 9.96 | 273 |
| H3FNG9 | Uncharacterized protein | SDAKKLMRDLKRML | 0.66 | 3 | 1.97 | 5.38 | 274 |
| Q29614 | Beta-lactoglobulin (Beta-LG) | NKGMNEFKKILRTLA | 0.65 | 3 | 1.95 | 5.56 | 275 |
| Q7M747 | Secretoglobin family 2B member 24 (Allergen dI chain C2B) (Androgen-binding protein zeta) (Lacrimal androgen-binding protein zeta) | FTKIKDALKKISQ | 0.65 | 3 | 1.95 | 6.11 | 276 |

TABLE 4-continued

Priority alpha core peptide sequences

| Accession # | Name | Comp Form Match | HM | Q | HM*Q | PI | SEQ ID NO: |
|---|---|---|---|---|---|---|---|
| P15457 | 2S seed storage protein 1 (2S albumin storage protein) (NWMU2-2S albumin 1) [Cleaved into: 2S seed storage protein 1 small subunit; 2S seed storage protein 1 large subunit] | VRKIYQTAKHLP | 0.56 | 3.5 | 1.95 | 10.44 | 277 |
| Q0V822 | Protein RALF-like 26 | VHNYSRGCSRITRCR | 0.43 | 4.5 | 1.95 | 11.19 | 278 |
| J9P346 | Uncharacterized protein | KIKRIVQKILESAER | 0.65 | 3 | 1.95 | 8.73 | 279 |
| P49164 | 50S ribosomal protein L34, chloroplastic | ARMATKLGRKVLN | 0.48 | 4 | 1.93 | 12.23 | 280 |
| A5WYF5 | Putative 4.8 kDa secreted salivary gland protein | KTLVNLWSKLAQRIF | 0.64 | 3 | 1.93 | 4.53 | 281 |
| Q9GZZ8 | Extracellular glycoprotein lacritin | QALAKAGKGMHGGVPGGKQ FIENGS  EFAQKLLKKF | 0.43 | 4.5 | 1.93 | 5.17 | 282 |
| Q9FZA0 | Protein RALF-like 4 | NPYRRGCSAITHCYRYAR | 0.43 | 4.5 | 1.92 | 10.76 | 283 |
| K9JHY4 | Leptin | RVKQVLNQLLKNMDHLK | 0.55 | 3.5 | 1.92 | 9.15 | 284 |
| A0A076YJS8 | Interleukin 4/13-3 | VSSFLEHVKRCVRH | 0.63 | 3 | 1.90 | 8.59 | 285 |
| A0A023G9C2 | Putative secreted protein | LRTVTELLKKVVDAAKK | 0.63 | 3 | 1.90 | 5.02 | 286 |
| B4G535 | Protein Turandot Z | AKALFNKLTEYLKK | 0.63 | 3 | 1.90 | 5.25 | 287 |

TABLE 4-continued

Priority alpha core peptide sequences

| Accession # | Name | Comp Form Match | HM | Q | HM*Q | PI | SEQ ID NO: |
|---|---|---|---|---|---|---|---|
| B1MTQ2 | Interleukin 13 (Predicted) | EVAQFVKDLLRHLRKLFHQ G | 0.63 | 3 | 1.89 | 9.02 | 288 |
| B0KWP3 | Interleukin 13 (Interleukin 13 (Predicted)) | EVAQFVKDLLRHLRKLFHQ G | 0.63 | 3 | 1.89 | 8.78 | 289 |
| F7H944 | Uncharacterized protein (Fragment) | EVAQFVKDLLRHLRKLFHQ G | 0.63 | 3 | 1.89 | 8.69 | 290 |
| E9Q6L3 | Methylglutaconyl-CoA hydratase, mitochondrial | KNLLKMLSKAVDALKS | 0.62 | 3 | 1.87 | 9.72 | 291 |
| Q9P0W0 | Interferon kappa (IFN-kappa) | LRRYFHRIDNFLKE | 0.74 | 2.5 | 1.86 | 8.8 | 292 |
| O82377 | EMBRYO SURROUNDING FACTOR 1-like protein 6 | SRCYRSLYKCVA | 0.62 | 3 | 1.85 | 8.9 | 293 |
| G3V2A7 | Type II iodothyronine deiodinase | QWLTSCWSTLMRLIHQMAG RYR | 0.53 | 3.5 | 1.84 | 10.86 | 294 |
| P48131 | 50S ribosomal protein L36, cyanelle | ASVRKMCEKCRTIR | 0.46 | 4 | 1.84 | 11.64 | 295 |
| Q43194 | Non-specific lipid-transfer protein 2 (LTP 2) | CLKNAARGIRGLN | 0.61 | 3 | 1.83 | 9.45 | 296 |
| Q0IQK9 | Non-specific lipid-transfer protein 1 (LTP 1) (PAPI) | CLKNAARGIKGLN | 0.61 | 3 | 1.83 | 9.41 | 297 |
| B5FW67 | Interleukin 13 (Predicted) (Uncharacterized protein) | EVAQFIKDLLRHLKK | 0.72 | 2.5 | 1.81 | 9.42 | 298 |
| P58784 | Trp-Contryphan-P | GGAIGKFMNVLRR | 0.60 | 3 | 1.79 | 3.8 | 299 |
| O65919 | Protein RALF-like 10 | ANEYRRGCSKITRCK | 0.45 | 4 | 1.79 | 9.69 | 300 |
| P0C0P7 | Neuropeptide S | RSFRNGVGSGVKK | 0.45 | 4 | 1.78 | 12.31 | 301 |
| G2TRK4 | Uncharacterized protein C1399.06 | TILRKARNLLNHGI | 0.51 | 3.5 | 1.78 | 10.3 | 302 |

TABLE 4-continued

Priority alpha core peptide sequences

| Accession # | Name | Comp Form Match | HM | Q | HM*Q | PI | SEQ ID NO: |
|---|---|---|---|---|---|---|---|
| P86941 | Insulinotropic peptide 1 (FSIP) | AVWKDFLKNIGKAAGKAV | 0.59 | 3 | 1.78 | 8.47 | 303 |
| B4MKX9 | GK17255 | KHAHSMITSMLSFVNSVVN FGRSFV RN | 0.44 | 4 | 1.78 | 8.14 | 304 |
| A0A016W2T3 | Uncharacterized protein | VKKMLKDVPKLATS | 0.59 | 3 | 1.78 | 8.28 | 305 |
| Q5UW37 | VEGF coregulated chemokine 1 (13.6 kDa protein) (C-X-C motif chemokine 17) | RACQQFLKRCHL | 0.51 | 3.5 | 1.77 | 10.37 | 306 |
| Q9GLK4 | Natriuretic peptides B (Gamma-brain natriuretic peptide) [Cleaved into: Brain natriuretic peptide 32 (BNP-32)] | NVLRALRRLGSS | 0.59 | 3 | 1.77 | 7.09 | 307 |
| A0A074ZW10 | Uncharacterized protein | GKNWSEFVRSMLRAMSKVA A | 0.59 | 3 | 1.77 | 5.07 | 308 |
| G3T2N9 | Uncharacterized protein | ELITFMKNLLDHLRRIYR | 0.71 | 2.5 | 1.76 | 9.23 | 309 |
| Q2XPU9 | Vdg3 | ICKSFQSLVHRFGHVT | 0.58 | 3 | 1.75 | 5.32 | 310 |
| P22298 | Antileukoproteinase (ALP) (Secretory leukocyte protease inhibitor) (Fragment) | LKCCKSMCGKVC | 0.58 | 3 | 1.75 | 9.11 | 311 |
| O77234 | SPO-1 protein (Stage-specific protein SPO-1) (Stathmin-like protein) | KRMEYIAKKLDK | 0.58 | 3 | 1.74 | 8.92 | 312 |
| H2MKX6 | Uncharacterized protein | ASWQQIFQRIIRVLRS | 0.58 | 3 | 1.73 | 11.83 | 313 |
| P15696 | Interferon tan-1 (IFN-tau-1) (Antiluteolysin) (Trophoblast antiluteolytic protein) | KRLRKMGGDLNSL | 0.58 | 3 | 1.73 | 5.74 | 314 |

TABLE 4-continued

| | | Priority alpha core peptide sequences | | | | | |
|---|---|---|---|---|---|---|---|
| Accession # | Name | Comp Form Match | HM | Q | HM*Q | PI | SEQ ID NO: |
| | (Trophoblast protein 1) (TP-1) (Trophoblastin) | | | | | | |
| M4WK63 | Cul o 5 allergen | KSYVEKLTKALSTIRQCI | 0.57 | 3 | 1.72 | 9.23 | 315 |
| A8CL69 | PBAN-type neuropeptides (Pheromone/ pyrokinin biosynthesis- activating neuropeptide) [Cleaved into: TSQDITSGMWFGPRL- amide (Pyrokinin-1); QITQFTPRL-amide (Pyrokinin-2); IYLPLFASRL- amide; VPWTPSPRL-amide] | RLGRQLHNIVDK | 0.69 | 2.5 | 1.72 | 5.5 | 316 |
| F6R9B2 | Uncharacterized protein (Fragment) | SQLTNLIRSVRTVMR | 0.57 | 3 | 1.71 | 8.95 | 317 |
| Q3SYR5 | Apolipoprotein C-IV (Apo-CIV) (ApoC-IV) (Apolipoprotein C4) | LKDLGSRARAWLRS | 0.57 | 3 | 1.71 | 9.07 | 318 |
| P0C0P5 | Neuropeptide S | RSFRNGVGTGMKK | 0.43 | 4 | 1.71 | 12.31 | 319 |
| P0C0P6 | Neuropeptide S | RSFRNGVGTGMKK | 0.43 | 4 | 1.71 | 12.02 | 320 |
| Q6NME6 | Protein RALF-like 19 | YRRGCSVITHCYRQ | 0.49 | 3.5 | 1.71 | 10.75 | 321 |
| P07597 | Non-specific lipid-transfer protein 1 (LTP 1) (Probable amylase/protease inhibitor) | CLKGIARGIHNLN | 0.68 | 2.5 | 1.70 | 8.19 | 322 |
| Q9WVA9 | Pro-FMRFamide- related neuropeptide FF (FMRFamide-related peptides) [Cleaved into: Neuropeptide SF (NPSF); Neuropeptide FF (NPFF); | RFGRNAWGPWSK | 0.56 | 3 | 1.69 | 9.75 | 323 |

TABLE 4-continued

Priority alpha core peptide sequences

| Accession # | Name | Comp Form Match | HM | Q | HM*Q | PI | SEQ ID NO: |
|---|---|---|---|---|---|---|---|
| | Neuropeptide AF-like (NPAF)] | | | | | | |
| Q9SRY3 | Protein RALF-like 1 (Rapid alkalinization factor 1) (AtRALF1) | ANPYSRGCSKIARCR | 0.42 | 4 | 1.69 | 10.06 | 324 |
| A0A024GHZ6 | Albugo candida WGS project CAIX00000000 data, strain Ac Nc2, contig AcNc2 CONTIG 128 length 64418 | ILHSFLKVLHHL | 0.67 | 2.5 | 1.69 | 9.18 | 325 |
| Q91159 | Lysozyme C (EC 3.2.1.17) (1,4-beta-N-acetylmuramidase C) | IKCAKKIARDAHGLT | 0.48 | 3.5 | 1.69 | 5.11 | 326 |
| Q5DF01 | SJCHGC01792 protein | VLKLWNSVLKHICNLS | 0.67 | 2.5 | 1.69 | 4.41 | 327 |
| B5L332 | CSF3 (Uncharacterized protein) | LRQLRSFMQDVFRSLRC | 0.56 | 3 | 1.68 | 8.12 | 328 |
| Q70PW6 | Peptidoglycan-recognition protein SB2 (EC 3.5.1.28) | GRHLLNELKKWP | 0.67 | 2.5 | 1.68 | 11.06 | 329 |
| P24296 | Non-specific lipid-transfer protein (LTP) (Phospholipid transfer protein) (PLTP) (ns-LTP1) (Fragment) | NCLKGIARGIHNLN | 0.67 | 2.5 | 1.67 | 8.2 | 330 |
| K7M000 | Uncharacterized protein | WRRVMHCFSYCW | 0.67 | 2.5 | 1.67 | 8.35 | 331 |
| P0C0P8 | Neuropeptide S | RSFRNGVGSGAKK | 0.42 | 4 | 1.66 | 12.31 | 332 |
| B9RZ82 | Putative uncharacterized protein | DLTRALHDLVKALKKAYRT LD | 0.66 | 2.5 | 1.66 | 5.64 | 333 |

TABLE 4-continued

| Priority alpha core peptide sequences | | | | | | | |
|---|---|---|---|---|---|---|---|
| Accession # | Name | Comp Form Match | HM | Q | HM*Q | PI | SEQ ID NO: |
| O46633 | Interferon tan (IFN-tau) (Antiluteolysin) (Trophoblast antiluteolytic protein) (Trophoblast protein 1) (TP-1) (Trophoblastin) | KRLRKMGGDLNS | 0.55 | 3 | 1.66 | 6.57 | 334 |
| A0A093R5C1 | Uncharacterized protein (Fragment) | KNATTFIEKLMTFIRKA | 0.55 | 3 | 1.66 | 7.99 | 335 |
| M3VWX3 | Uncharacterized protein (Fragment) | EVIQLVKNLLNHLRR | 0.66 | 2.5 | 1.65 | 9.42 | 336 |
| G1T948 | Interleukin (Fragment) | LKEFLERLKSLIQKMIHQ | 0.66 | 2.5 | 1.65 | 9.67 | 337 |
| O64466 | Protein RALF-like 11 | VNEYSRGCSKIHRCR | 0.47 | 3.5 | 1.65 | 8.5 | 338 |
| F4ISE1 | Protein RALF-like 12 | VNEYSRGCSKIHRCR | 0.47 | 3.5 | 1.65 | 8.5 | 339 |
| F4ISE2 | Protein RALF-like 13 | VNEYSRGCSKIHRCR | 0.47 | 3.5 | 1.65 | 8.5 | 340 |
| M4QCE6 | Adipokinetic 3 | CGQFTRLCRHFVHELKQALTS | 0.55 | 3 | 1.65 | 6.45 | 341 |
| E9NX77 | AKH/corazonin-like hormone | CGQFTRLCRHFVHELKQALTS | 0.55 | 3 | 1.65 | 6.44 | 342 |
| Q9XSN5 | Apolipoprotein C-I (Apo-CI) (ApoC-I) (Apolipoprotein C1) [Cleaved into: Truncated apolipoprotein C-I] | DKAKKAIERIKQ | 0.55 | 3 | 1.64 | 9.11 | 343 |
| R0MG91 | Uncharacterized protein | EKISDWWKRIWEKIKN | 0.82 | 2 | 1.63 | 5.34 | 344 |
| P02815 | Mucin-like protein 2 (16.5 kDa submandibular gland glycoprotein) (Salivary protein 1) | LENMKTVIKSGVEKLKNFLQRG | 0.54 | 3 | 1.63 | 3.8 | 345 |
| A0A087VIJ1 | Uncharacterized protein | NATRFMEKLMTFVRKA | 0.54 | 3 | 1.62 | 8.87 | 346 |

TABLE 4-continued

Priority alpha core peptide sequences

| Accession # | Name | Comp Form Match | HM | Q | HM*Q | PI | SEQ ID NO: |
|---|---|---|---|---|---|---|---|
| Q4G392 | 50S ribosomal protein L34, chloroplastic | RMATKAGRRVINAR | 0.32 | 5 | 1.62 | 12.96 | 347 |
| U3JCF4 | Uncharacterized protein (Fragment) | ILANFQRFLETAYRALRHL | 0.64 | 2.5 | 1.61 | 5.39 | 348 |
| Q9WVA8 | Pro-FMRFamide-related neuropeptide FF (FMRFamide-related peptides) [Cleaved into: Neuropeptide SF (NPSF); Neuropeptide FF (NPFF); Neuropeptide AF-like (NPAF)] | RFGRSAWGSWSK | 0.54 | 3 | 1.61 | 9.47 | 349 |
| A0A061HZA0 | Ras-related and estrogen-regulated growth inhibitor-like protein | THVKQAINKMLTK1SS | 0.46 | 3.5 | 1.61 | 5.48 | 350 |
| A8XRC0 | Protein CBG17503 | RELPKVCRNIFSRVSL | 0.53 | 3 | 1.60 | 5.86 | 351 |
| Q9TLU9 | 50S ribosomal protein L36, chloroplastic | ASVRKICSRCVALK | 0.40 | 4 | 1.60 | 11.48 | 352 |
| P06833 | Caltrin (Calcium transport inhibitor) (Peptide YY-2) (Peptide YY2) (Seminalplasmin) (SPLN) | LSRYAKLANRLANP | 0.53 | 3 | 1.60 | 10.36 | 353 |
| V5IDJ5 | Putative secreted protein (Fragment) | DILRECAKGLEVRVAENQH LANETV  EYFFKKLWRGVKKVVKK | 0.35 | 4.5 | 1.60 | 5.86 | 354 |
| Q94CG1 | Glycine rich protein | YGCCRKGYNGCKRCCSYAG EAIDKV | 0.53 | 3 | 1.59 | 8.79 | 355 |
| D2K2T8 | Glycine-rich protein | YGCCRKGYNGCKRCCSYAG EAIDKV | 0.53 | 3 | 1.59 | 8.79 | 356 |
| G1NDN8 | Interleukin | QEFLNSFSKLMQKVIKIH | 0.64 | 2.5 | 1.59 | 9.07 | 357 |
| A4K2W7 | WAP four-disulfide core | RCLSPMNHLCHK | 0.53 | 3 | 1.59 | 8.73 | 358 |

TABLE 4-continued

Priority alpha core peptide sequences

| Accession # | Name | Comp Form Match | HM | Q | HM*Q | PI | SEQ ID NO: |
|---|---|---|---|---|---|---|---|
| | domain protein 5 | | | | | | |
| A4K2T2 | WAP four-disulfide core domain protein 5 | RCLSPMNHLCHK | 0.53 | 3 | 1.59 | 8.73 | 359 |
| F9X658 | Uncharacterized protein | AFNAVKRLLDQARQLGR | 0.53 | 3 | 1.58 | 9.3 | 360 |
| V5H076 | Putative secreted protein | AAKNALQKFIEEMKKIK | 0.53 | 3 | 1.58 | 6.14 | 361 |
| W2XXG7 | Uncharacterized protein | EVKKIWATIIERLYKLWRD W | 0.79 | 2 | 1.57 | 9.82 | 362 |
| P54615 | Osteocalcin-related protein (Gamma-carboxyglutamic acid-containing protein 3) (Nephrocalcin) (OC-X) | GLKTAYRRIYGI | 0.52 | 3 | 1.57 | 4.44 | 363 |
| P86546 | Osteocalcin (Bone Gla protein) (BGP) (Gamma-carboxyglutamic acid-containing protein) | GLKTAYKRIYGI | 0.52 | 3 | 1.56 | 4.44 | 364 |
| P86547 | Osteocalcin-2 (Bone Gla protein 2) (BGP2) (Gamma-carboxyglutamic acid-containing protein 2) | GLKTAYKRIYGI | 0.52 | 3 | 1.56 | 4.44 | 365 |
| V9NK57 | IL-4 delta 3 | LKDFLENLKRIMQK | 0.78 | 2 | 1.56 | 9.81 | 366 |
| V5H5J7 | Putative secreted protein | QVLHQVQKLANELLRKL | 0.62 | 2.5 | 1.56 | 9.69 | 367 |
| Q8GWK5 | Gibberellin-regulated protein 9 (GAST1 protein homolog 9) | CHRACGSCCAKC | 0.62 | 2.5 | 1.56 | 9.36 | 368 |
| P81765 | Tyrosinase inhibitor (Phenol oxidase | QCLANGSKCYSHDVCCTKR CHNYA | 0.31 | 5 | 1.56 | 8.32 | 369 |

TABLE 4-continued

| | | Priority alpha core peptide sequences | | | | | |
|---|---|---|---|---|---|---|---|
| Accession # | Name | Comp Form Match | HM | Q | HM*Q | PI | SEQ ID NO: |
| | inhibitor) (Phenoloxidase inhibitor) (POI) | KKCVT | | | | | |
| A0A091LH39 | Uncharacterized protein (Fragment) | KSATTFIEKLTTFIRKAS | 0.52 | 3 | 1.55 | 8.98 | 370 |
| Q7M1H2 | Glycine-rich protein | KGYYKGCKKCCSYAGQAMD KVTE | 0.52 | 3 | 1.55 | 9.28 | 371 |
| A0A091FKF3 | Myelomonocytic growth factor (Fragment) | ILANFQRFLETAYRALRHL A | 0.62 | 2.5 | 1.55 | 6.57 | 372 |
| G5E3B9 | Putative udp-n-acetyl-alpha-d-galactosamine polypeptide n-acetyl galactos aminyltransferase (Fragment) | EGWSTLMRTVHSVIKR | 0.62 | 2.5 | 1.55 | 5.04 | 373 |
| D7MAD4 | Putative uncharacterized protein | DLSSVAKTLIHRLHK | 0.51 | 3 | 1.54 | 4.77 | 374 |
| P23137 | Glycine-rich protein | YGCCRKGYNGCKRCCSYAG EAMDKV | 0.51 | 3 | 1.53 | 8.29 | 375 |
| Q9FXS8 | Glycine rich protein (Glycine-rich protein) | YGCCRKGYNGCKRCCSYAG EAMDKV | 0.51 | 3 | 1.53 | 8.27 | 376 |
| Q9LWA1 | Cell wall protein (Glycine-rich protein) | YGCCRKGYNGCKRCCSYAG EAMDKV | 0.51 | 3 | 1.53 | 7.8 | 377 |
| P15460 | 2S seed storage protein 4 (2S albumin storage protein) (NWMU2-2S albumin 4) [Cleaved into: 2S seed storage protein 4 small subunit; 2S seed storage protein 4 large subunit] | VRKIYQAAKYLP | 0.51 | 3 | 1.53 | 10.32 | 378 |

TABLE 4-continued

Priority alpha core peptide sequences

| Accession # | Name | Comp Form Match | HM | Q | HM*Q | PI | SEQ ID NO: |
|---|---|---|---|---|---|---|---|
| A9RBU6 | Uncharacterized protein | ASQLLKVLHKIWTQVP | 0.61 | 2.5 | 1.53 | 7.13 | 379 |
| Q4XR40 | Putative uncharacterized protein (Fragment) | VALVTGAGRGIGRSIAK TLAKSVSHVL | 0.34 | 4.5 | 1.52 | 9.95 | 380 |
| P01740 | T-cell receptor gamma chain V region V108A | RWSSGFHKVFAEGTKLI | 0.61 | 2.5 | 1.52 | 7.92 | 381 |
| G1LH25 | Interleukin | KEFLERLKSLIQRMIHQ | 0.60 | 2.5 | 1.50 | 9.66 | 382 |
| X2FJF4 | Interleukin-4 (Fragment) | KLSNMLRNLMHLVNQ | 0.60 | 2.5 | 1.50 | 6.13 | 383 |
| I3SFC2 | Uncharacterized protein | RVIKCIDHICQYARNL | 0.60 | 2.5 | 1.50 | 6.92 | 384 |
| A7KHG0 | Nodule Cysteine-Rich (NCR) secreted peptide (Nodule-specific cysteine-rich peptide 330) | RVIKCIDHICQYARNL | 0.60 | 2.5 | 1.50 | 6.06 | 385 |
| H2PE90 | Interleukin | KEFLERFKSLLQKMIHQ | 0.60 | 2.5 | 1.50 | 9.42 | 386 |
| H2QQ45 | Interleukin | KEFLERFKSLLQKMIHQ | 0.60 | 2.5 | 1.50 | 9.42 | 387 |
| G1RE48 | Interleukin | KEFLERFKSLLQKMIHQ | 0.60 | 2.5 | 1.50 | 9.42 | 388 |
| G3QY93 | Interleukin | KEFLERFKSLLQKMIHQ | 0.60 | 2.5 | 1.50 | 9.42 | 389 |
| Q9HBE4 | Interleukin-21 (IL-21) (Zall) | KEFLERFKSLLQKMIHQ | 0.60 | 2.5 | 1.50 | 9.42 | 390 |
| F7EGQ8 | Interleukin | KEFLERFKSLLQKMIHQ | 0.60 | 2.5 | 1.50 | 9.12 | 391 |
| G7P680 | Interleukin | KEFLERFKSLLQKMIHQ | 0.60 | 2.5 | 1.50 | 9.12 | 392 |
| A0A096N144 | Uncharacterized protein | KEFLERFKSLLQKMIHQ | 0.60 | 2.5 | 1.50 | 9.12 | 393 |
| M3W5A3 | Interleukin | KEFLERLKSLIQKMIHQ | 0.60 | 2.5 | 1.50 | 9.51 | 394 |
| Q6L7I9 | Interleukin-21 (IL-21) | KEFLERLKSLIQKMIHQ | 0.60 | 2.5 | 1.50 | 9.42 | 395 |
| A2D655 | IL10 (Fragment) | HMLRDLRDAFSRVKTFF | 0.60 | 2.5 | 1.49 | 9.49 | 396 |
| A2D4R8 | IL10 (Fragment) | HMLRDLRDAFSRVKTFF | 0.60 | 2.5 | 1.49 | 9.49 | 397 |
| A2T6I1 | IL10 (Fragment) | HMLRDLRDAFSRVKTFF | 0.60 | 2.5 | 1.49 | 9.49 | 398 |
| G3SXC9 | Interleukin | KEFLERLKSLLQKMIHQ | 0.60 | 2.5 | 1.49 | 9.73 | 399 |
| A0A078GU36 | BnaCnng05800D protein | KKAASVIQKILKDFGL | 0.49 | 3 | 1.48 | 9.75 | 400 |

TABLE 4-continued

| | | Priority alpha core peptide sequences | | | | | |
|---|---|---|---|---|---|---|---|
| Accession # | Name | Comp Form Match | HM | Q | HM*Q | PI | SEQ ID NO: |
| M4FHC5 | Uncharacterized protein | KKAASVIQKILKDFGL | 0.49 | 3 | 1.48 | 9.75 | 401 |
| Q2V2Y3 | Putative defensin-like protein 84 | CMKKGGGHCQAYIGR | 0.42 | 3.5 | 1.48 | 8.88 | 402 |
| Q6V9X0 | Antileukoproteinase (ALP) (Secretory leukocyte protease inhibitor) | GALKCCKAMCGKVC | 0.49 | 3 | 1.47 | 8.6 | 403 |
| E0W4Y8 | Avh313 | KTLARWAQNAFSKLL | 0.49 | 3 | 1.47 | 10.14 | 404 |
| G5A7V2 | Putative uncharacterized protein | KTLARWAQNAFSKLL | 0.49 | 3 | 1.47 | 10.14 | 405 |
| I3MIK7 | Interleukin | KEFLERLKSLLQKMVHQ | 0.59 | 2.5 | 1.46 | 9.69 | 406 |
| P0DKV5 | Apolipoprotein C-I (Apo-CI) (ApoC-I) (Apolipoprotein C1) [Cleaved into: Truncated apolipoprotein C-I] | DKVREFFKRIKE | 0.73 | 2 | 1.46 | 8.28 | 407 |
| Q66KU1 | C-type lectin domain family 3 member A *homo*log (C-type lectin superfamily member 1 *homo*log) | GKWVDEVCRSLKKYI | 0.73 | 2 | 1.46 | 8.96 | 408 |
| A0A078FAD2 | BnaA09g39310D protein | SAMERLNNWLKTFKH | 0.58 | 2.5 | 1.45 | 7.98 | 409 |
| H0GU2 | YJL160C-like protein | VVSHIVSQIGDGQ LQITTAKKCCHK VHNCCSK | 0.32 | 4.5 | 1.44 | 9.06 | 410 |
| L7JS03 | Uncharacterized protein (Fragment) | RRCVNNFDDVFNSVFRKL | 0.72 | 2 | 1.44 | 7.82 | 411 |
| D7REK7 | Interleukin-4 | STLRDFLERLKKIMKE | 0.72 | 2 | 1.44 | 9.46 | 412 |
| Q865X5 | Interleukin-4 (IL-4) (B-cell stimulatory factor 1) (BSF-1) (Lymphocyte stimulatory factor 1) | STLRDFLERLKKIMKE | 0.72 | 2 | 1.44 | 9.46 | 413 |

TABLE 4-continued

Priority alpha core peptide sequences

| Accession # | Name | Comp Form Match | HM | Q | HM*Q | PI | SEQ ID NO: |
|---|---|---|---|---|---|---|---|
| P51744 | Interleukin-4 (IL-4) (B-cell stimulatory factor 1) (BSF-1) (Lymphocyte stimulatory factor 1) | LKNLLERLKTIMKE | 0.72 | 2 | 1.44 | 9.51 | 414 |
| Q9EQ14 | Interleukin-23 subunit alpha (IL-23 subunit alpha) (IL-23-A) (Interleukin-23 subunit p19) (IL-23p19) | SKILRSLQAFLAIAARVFA HGAA | 0.41 | 3.5 | 1.43 | 5.85 | 415 |
| Q91Z84 | Interleukin-23 subunit alpha (IL-23 subunit alpha) (IL-23-A) (Interleukin-23 subunit p19) (IL-23p19) | SKILRSLQAFLAIAARVFA HGAA | 0.41 | 3.5 | 1.43 | 5.63 | 416 |
| P06307 | Cholecystokinin (CCK) [Cleaved into: Cholecystokinin-58 (CCK58); Cholecystokinin-58 desnonopeptide ((1-49)-CCK58); Cholecystokinin-39 (CCK39); Cholecystokinin-33 (CCK33); Cholecystokinin-25 (CCK25); Cholecystokinin-18 (CCK18); Cholecystokinin-12 (CCK12); Cholecystokinin-8 (CCK8); Cholecystokinin-7 (CCK7); Cholecystokinin-5 (CCK5)] | AHLGALLARYIQQARKA | 0.41 | 3.5 | 1.43 | 9.7 | 417 |
| Q3E7Z9 | Uncharacterized protein YOL038C-A | MKYMGSFLRKAAT | 0.48 | 3 | 1.43 | 11.76 | 418 |
| P32648 | VIP peptides [Cleaved into: | AVKKYLNSILNGK | 0.48 | 3 | 1.43 | 6.76 | 419 |

83  84

TABLE 4-continued

Priority alpha core peptide sequences

| Accession # | Name | Comp Form Match | HM | Q | HM*Q | PI | SEQ ID NO: |
|---|---|---|---|---|---|---|---|
| | Intestinal peptide PHI-42; Intestinal peptide PHI-27 (Peptide histidine isoleucinamide 27); Vasoactive intestinal peptide (VIP) (Vasoactive intestinal polypeptide)] | | | | | | |
| P01282 | VIP peptides [Cleaved into: Intestinal peptide PHV-42 (Peptide histidine valine 42); Intestinal peptide PHM-27 (Peptide histidine methioninamide 27); Vasoactive intestinal peptide (VIP) (Vasoactive intestinal polypeptide)] | AVKKYLNSILNGK | 0.48 | 3 | 1.43 | 6.76 | 420 |
| P01283 | VIP peptides [Cleaved into: Intestinal peptide PHV-42; Intestinal peptide PHI-27 (Peptide histidine isoleucinamide 27); Vasoactive intestinal peptide (VIP) (Vasoactive intestinal polypeptide)] | AVKKYLNSILNGK | 0.48 | 3 | 1.43 | 6.76 | 421 |
| P81401 | VIP peptides [Cleaved into: Intestinal | AVKKYLNSILNGK | 0.48 | 3 | 1.43 | 6.75 | 422 |

TABLE 4-continued

Priority alpha core peptide sequences

| Accession # | Name | Comp Form Match | HM | Q | HM*Q | PI | SEQ ID NO: |
|---|---|---|---|---|---|---|---|
| | peptide PHI-27 (Peptide histidine isoleucinamide 27); Vasoactive intestinal peptide (VIP) (Vasoactive intestinal polypeptide)] | | | | | | |
| Q76LU5 | Interleukin-21 (IL-21) | KEYLERLKSLIQKMIHQ | 0.57 | 2.5 | 1.43 | 9.46 | 423 |
| C7BVU1 | Putative DNA-binding response regulator CreB | KNVVEDIKKILQKMW | 0.71 | 2 | 1.43 | 4.56 | 424 |
| Q2V4J2 | Putative defensin-like protein 26 | QRCNRWCHNGCGNGKGGYY KSMSHGGQ | 0.29 | 5 | 1.43 | 8.46 | 425 |
| H0VLF2 | Interleukin | REFLERMKSLLQKMIHQ | 0.57 | 2.5 | 1.42 | 9.61 | 426 |
| D2HN52 | Interleukin (Fragment) | KEFLERLKSLIQRV | 0.71 | 2 | 1.42 | 9.66 | 427 |
| P01213 | Proenkephalin-B (Beta-neoendorphin-dynorphin) (Preprodynorphin) [Cleaved into: Alpha-neoendorphin; Beta-neoendorphin; Big dynorphin (Big Dyn); Dynorphin A(1-17) (Dyn-A17) (Dynorphin A); Dynorphin A(1-13); Dynorphin A (1-8); Leu-enkephalin; Rimorphin (Dynorphin B) (Dyn-B) (Dynorphin B (1-13)); Leumorphin (Dynorphin B-29)] | EDLYKRYGGFLRRI | 0.71 | 2 | 1.42 | 6.1 | 428 |
| P24514 | Chorion protein S18 | SSVAGVAKKGYRK | 0.35 | 4 | 1.42 | 9.82 | 429 |
| W9R9I1 | Uncharacterized protein | RRLLEAAKEIVSLMHK | 0.56 | 2.5 | 1.41 | 5.9 | 430 |

TABLE 4-continued

| | | Priority alpha core peptide sequences | | | | | |
|---|---|---|---|---|---|---|---|
| Accession # | Name | Comp Form Match | HM | Q | HM*Q | PI | SEQ ID NO: |
| G4LYD1 | MEG-5 | KTLGTAFKTLLHNLWDLLKQ | 0.56 | 2.5 | 1.40 | 8.18 | 431 |
| R7ULK2 | Uncharacterized protein (Fragment) | LIKRFSTLWRDIWQVASNF | 0.70 | 2 | 1.40 | 5.75 | 432 |
| P55030 | Interleukin-4 (IL-4) (B-cell stimulatory factor 1) (BSF-1) (Lymphocyte stimulatory factor 1) | LKDFLERLKAIMQK | 0.70 | 2 | 1.40 | 9.57 | 433 |
| Q3ECL0 | Protein RALF-like 9 | ANPYQRGCEKINRCR | 0.46 | 3 | 1.39 | 9.3 | 434 |
| B4LKD2 | GJ20154 | CRVARDFLRECMQHLKY | 0.56 | 2.5 | 1.39 | 5.49 | 435 |
| O95968 | Secretoglobin family ID member 1 (Lipophilin-A) | KTLGKIAEKCDR | 0.69 | 2 | 1.39 | 9.47 | 436 |
| Q2V392 | Putative defensin-like protein 25 | QRCNRWCHNGCGNGKG | 0.40 | 3.5 | 1.39 | 8.39 | 437 |
| J7HBR9 | Maxadilan related protein | SKAKDAIAGLFTKAKSALKDVL | 0.46 | 3 | 1.38 | 9.78 | 438 |
| M3Z119 | Interleukin | KEFLERLKSLIQRMI | 0.69 | 2 | 1.38 | 9.37 | 439 |
| Q9TV67 | Interferon gamma (IFN-gamma) | RKAISELIRVMKDL | 0.69 | 2 | 1.38 | 9.8 | 440 |
| Q22T52 | Transmembrane protein, putative | KTIQSWLNKFLSCLHI | 0.55 | 2.5 | 1.38 | 7.7 | 441 |
| P0C5M1 | Uncharacterized protein YDR371C-A | MSAIVKWSNIIRPL | 0.69 | 2 | 1.38 | 9.99 | 442 |
| D3GGX2 | Interleukin | QEFLNSFSKLMQKLFKN | 0.68 | 2 | 1.37 | 9.32 | 443 |
| Q58IU6 | Interleukin | QEFLNSFSKLMQKLFKN | 0.68 | 2 | 1.37 | 9.3 | 444 |
| L7MA95 | Putative secreted peptide | ADKCLRYLLKNI | 0.68 | 2 | 1.37 | 9.59 | 445 |
| A0CK36 | Chromosome undetermined scaffold_2, whole genome shotgun sequence | FKNCVKNILKDCQT | 0.68 | 2 | 1.36 | 5.87 | 446 |

TABLE 4-continued

| Priority alpha core peptide sequences | | | | | | | |
|---|---|---|---|---|---|---|---|
| Accession # | Name | Comp Form Match | HM | Q | HM*Q | PI | SEQ ID NO: |
| A0A061J336 | Pterin-4-alpha-carbinolamine dehydratase | LARRMNEVFKEMLRP | 0.68 | 2 | 1.36 | 6.19 | 447 |
| C4R2P5 | Long chronological lifespan protein 2 | CKWVEKAWKGLL | 0.68 | 2 | 1.35 | 5.24 | 448 |
| P05105 | Lysozyme (EC 3.2.1.17) (1,4-beta-N-acetylmuramidase) | ISVAATCAKKIYK | 0.45 | 3 | 1.35 | 8.8 | 449 |
| F4PF44 | Putative uncharacterized protein (Fragment) | NELKELVKKASDIIKK | 0.67 | 2 | 1.34 | 5 | 450 |
| P14730 | WAP four-disulfide core domain protein 18 (Extracellular peptidase inhibitor) (Protein WDNM1) (Fragment) | NIQKCCSNGCGHVCK | 0.54 | 2.5 | 1.34 | 8.77 | 451 |
| H3GQQ3 | Uncharacterized protein | NGLLQRIQSWWKNLFQHGAS | 0.54 | 2.5 | 1.34 | 9.29 | 452 |
| V9NJM6 | IL-4 delta 3 | TTLKDFLENLKRIMQK | 0.67 | 2 | 1.34 | 8.85 | 453 |
| A7KH73 | Nodule Cysteine-Rich (NCR) secreted peptide (Nodule-specific cysteine-rich peptide 54) (Uncharacterized protein) | FREIPQCINSICKCMKG | 0.67 | 2 | 1.34 | 6.5 | 454 |
| P48617 | Erythropoietin | DALSKLFRIYSNFLRG | 0.67 | 2 | 1.33 | 8.68 | 455 |
| P33709 | Erythropoietin | DALSKLFRIYSNFLRG | 0.67 | 2 | 1.33 | 8.68 | 456 |
| Q6QN06 | Matrix Gia protein (MGP) | GYNAAYNRYFRK | 0.44 | 3 | 1.33 | 9.39 | 457 |
| P08493 | Matrix Gia protein (MGP) (Cell growth-inhibiting gene 36 protein) | GYNAAYNRYFRK | 0.44 | 3 | 1.33 | 8.66 | 458 |
| W7XBW1 | Uncharacterized protein | DSIFSKMYNCWRKCA | 0.67 | 2 | 1.33 | 6.29 | 459 |

TABLE 4-continued

Priority alpha core peptide sequences

| Accession # | Name | Comp Form Match | HM | Q | HM*Q | PI | SEQ ID NO: |
|---|---|---|---|---|---|---|---|
| P33622 | Apolipoprotein C-III (Apo-CIII) (ApoC-III) (Apolipoprotein C3) | FRFLKGYWSKFTD | 0.66 | 2 | 1.33 | 4.35 | 460 |
| W5U2R0 | Pro-sepiatocin | QELFSLLKRLINKVN | 0.66 | 2 | 1.32 | 8.35 | 461 |
| W5U1W8 | Sepiatocin | QELFSLLKRLINKVN | 0.66 | 2 | 1.32 | 7.92 | 462 |
| Q4TJ01 | Chromosome undetermined SCAF1215, whole genome shotgun sequence | KLIDTVIKQLRNLIAT | 0.66 | 2 | 1.32 | 10.1 | 463 |
| G1QEP5 | Uncharacterized protein (Fragment) | LLEKIKTCWNKILSGT | 0.66 | 2 | 1.32 | 8.48 | 464 |
| P0C7P5 | Bradykinin-potentiating and C-type natriuretic peptides (BPP-CNP) [Cleaved into: Bradykinin-potentiating peptide Tfl; Bradykinin-potentiating peptide Tf2; Bradykinin-potentiating peptide Tf3; C-type natriuretic peptide Tf-CNP; C-type natriuretic peptide Tf-CNP(3-22); C-type natriuretic peptide Tf-CNP (6-22)] | GGGGGGGGGARRMKGLAKK AM | 0.26 | 5 | 1.32 | 11 | 465 |
| B7EY37 | cDNA clone:001-127-H01, full insert sequence | AAWFQFFNRFLKYITSL | 0.66 | 2 | 1.32 | 11.79 | 466 |
| G5ASQ0 | Interleukin-4 | TTLKDFLENLKTILKK | 0.66 | 2 | 1.31 | 8.78 | 467 |
| Q9FHA6 | Protein RALF-like 34 | VHPYSRGCSSITRCR | 0.37 | 3.5 | 1.31 | 10.63 | 468 |
| F7GL96 | Uncharacterized protein (Fragment) | LQS1LELVHRVLRHLAQ | 0.65 | 2 | 1.30 | 7.89 | 469 |

TABLE 4-continued

| | | Priority alpha core peptide sequences | | | | | |
|---|---|---|---|---|---|---|---|
| Accession # | Name | Comp Form Match | HM | Q | HM*Q | PI | SEQ ID NO: |
| H9KY95 | Uncharacterized protein (Fragment) | LQSFLELVHRVLRHLAQ | 0.65 | 2 | 1.30 | 6.4 | 470 |
| Q03461 | Non-specific lipid-transfer protein 2 (LTP 2) | CLKSAANAIKGI | 0.65 | 2 | 1.30 | 9.16 | 471 |
| V4MH62 | Uncharacterized protein | SVYAQLSSVARTMIKRLEH FI | 0.52 | 2.5 | 1.30 | 8.52 | 472 |
| P63291 | Vasoactive intestinal peptide (VIP) (Vasoactive intestinal polypeptide) | AVKKYLNSILN | 0.65 | 2 | 1.29 | 9.82 | 473 |
| P63290 | Vasoactive intestinal peptide (VIP) (Vasoactive intestinal polypeptide) | AVKKYLNSILN | 0.65 | 2 | 1.29 | 9.82 | 474 |
| P84488 | Vasoactive intestinal peptide (VIP) (Vasoactive intestinal polypeptide) | AVKKYLNSILN | 0.65 | 2 | 1.29 | 9.82 | 475 |
| P63289 | Vasoactive intestinal peptide (VIP) (Vasoactive intestinal polypeptide) | AVKKYLNSILN | 0.65 | 2 | 1.29 | 9.82 | 476 |
| V5HF12 | Putative secreted protein | QVGQILRECAKNLKN | 0.65 | 2 | 1.29 | 4.75 | 477 |
| P01581 | Interferon gamma (IFN-gamma) | HKAVNELIRVIHQL | 0.65 | 2 | 1.29 | 9.48 | 478 |
| L7M2P0 | Uncharacterized protein | RLLHGLLHSLLHS FSHKFLDSFMRH MCTVCRNM | 0.23 | 5.5 | 1.29 | 9.84 | 479 |
| D8TM42 | Putative uncharacterized protein | YWIHMLRYVAKT | 0.52 | 2.5 | 1.29 | 9.58 | 480 |
| P13589 | Pituitary adenylate cyclase-activating polypeptide (PACAP) [Cleaved into: PACAP-related peptide (PRP-48); | AVKKYLAAVLGK | 0.43 | 3 | 1.29 | 5.61 | 481 |

TABLE 4-continued

Priority alpha core peptide sequences

| Accession # | Name | Comp Form Match | HM | Q | HM*Q | PI | SEQ ID NO: |
|---|---|---|---|---|---|---|---|
| | Pituitary adenylate cyclase-activating polypeptide 27 (PACAP-27) (PACAP27); Pituitary adenylate cyclase-activating polypeptide 38 (PACAP-38) (PACAP38)] | | | | | | |
| P41535 | Pituitary adenylate cyclase-activating polypeptide (PACAP) [Cleaved into: PACAP-related peptide (PRP-48); Pituitary adenylate cyclase-activating polypeptide 27 (PACAP-27) (PACAP27); Pituitary adenylate cyclase-activating polypeptide 38 (PACAP-38) (PACAP38)] | AVKKYLAAVLGK | 0.43 | 3 | 1.29 | 5.57 | 482 |
| P16613 | Pituitary adenylate cyclase-activating polypeptide (PACAP) [Cleaved into: PACAP-related peptide (PRP-48); Pituitary adenylate cyclase-activating polypeptide 27 (PACAP-27) (PACAP27); Pituitary adenylate cyclase-activating polypeptide 38 (PACAP-38) (PACAP38)] | AVKKYLAAVLGK | 0.43 | 3 | 1.29 | 5.54 | 483 |

TABLE 4-continued

Priority alpha core peptide sequences

| Accession # | Name | Comp Form Match | HM | Q | HM*Q | PI | SEQ ID NO: |
|---|---|---|---|---|---|---|---|
| P18509 | Pituitary adenylate cyclase-activating polypeptide (PACAP) [Cleaved into: PACAP-related peptide (PRP-48); Pituitary adenylate cyclase-activating polypeptide 27 (PACAP-27) (PACAP27); Pituitary adenylate cyclase-activating polypeptide 38 (PACAP-38) (PACAP38)] | AVKKYLAAVLGK | 0.43 | 3 | 1.29 | 5.38 | 484 |
| O70176 | Pituitary adenylate cyclase-activating polypeptide (PACAP) [Cleaved into: PACAP-related peptide (PRP-48); Pituitary adenylate cyclase-activating polypeptide 27 (PACAP-27) (PACAP27); Pituitary adenylate cyclase-activating polypeptide 38 (PACAP-38) (PACAP38)] | AVKKYLAAVLGK | 0.43 | 3 | 1.29 | 5 | 485 |
| Q29W19 | Pituitary adenylate cyclase-activating polypeptide (PACAP) [Cleaved into: PACAP-related peptide (PRP-48); Pituitary adenylate cyclase-activating polypeptide 27 (PACAP-27) (PACAP27); Pituitary adenylate cyclase-activating polypeptide 38 (PACAP-38) (PACAP38)] | AVKKYLAAVLGK | 0.43 | 3 | 1.29 | 4.91 | 486 |

TABLE 4-continued

Priority alpha core peptide sequences

| Accession # | Name | Comp Form Match | HM | Q | HM*Q | PI | SEQ ID NO: |
|---|---|---|---|---|---|---|---|
| P41534 | Glucagon family neuropeptides [Cleaved into: Growth hormone-releasing factor 1-46 (GRF) (Growth hormone-releasing hormone) (GHRH); Pituitary adenylate cyclase-activating polypeptide 27 (PACAP-27) (PACAP27); Pituitary adenylate cyclase-activating polypeptide 38 (PACAP-38) (PACAP38)] | AVKKYLAAVLGK | 0.43 | 3 | 1.29 | 9.4 | 487 |
| P41585 | Glucagon family neuropeptides [Cleaved into: Growth hormone-releasing factor (GRF) (Growth hormone-releasing hormone) (GHRH); Pituitary adenylate cyclase-activating polypeptide (PACAP)] | AVKKYLAAVLGK | 0.43 | 3 | 1.29 | 9.31 | 488 |
| Q09169 | Glucagon family neuropeptides [Cleaved into: Growth hormone-releasing factor (GRF) (Growth hormone-releasing hormone) (GHRH); Pituitary adenylate cyclase-activating polypeptide 27 (PACAP-27) (PACAP27); | AVKKYLAAVLGK | 0.43 | 3 | 1.29 | 6.28 | 489 |

TABLE 4-continued

Priority alpha core peptide sequences

| Accession # | Name | Comp Form Match | HM | Q | HM*Q | PI | SEQ ID NO: |
|---|---|---|---|---|---|---|---|
| | Pituitary adenylate cyclase-activating polypeptide 38 (PACAP-38) (PACAP38)] | | | | | | |
| V9LKT2 | Interleukin | LKKFLQFIYYCC | 0.64 | 2 | 1.28 | 5.61 | 490 |
| D0N540 | Secreted RxLR effector peptide protein, putative (Fragment) | LSDAKQWIKTMFKNW | 0.64 | 2 | 1.28 | 5.96 | 491 |
| C9X4J0 | Bradykinin-potentiating peptide (BPP) (TdBPP) | AKGKQMLKEYANKV | 0.43 | 3 | 1.28 | 10 | 492 |
| P42692 | Somatoliberin (Growth hormone-releasing factor) (GRF) (Growth hormone-releasing hormone) (GHRH) | GMFNKAYRKALGQLSA | 0.43 | 3 | 1.28 | 9.31 | 493 |
| A8MQI8 | Protein RALF-like 5 | GGLSTWKKLLDTILKIP | 0.64 | 2 | 1.27 | 9.79 | 494 |
| A2ZAS9 | Non-specific lipid-transfer protein 3 (LTP 3) | CLKNMASSFRNLN | 0.63 | 2 | 1.27 | 8.92 | 495 |
| Q2QYL3 | Non-specific lipid-transfer protein 3 (LTP 3) | CLKNMASSFRNLN | 0.63 | 2 | 1.27 | 8.92 | 496 |
| L0GB04 | Lal-like protein 15 | VTCASQALKRGCKSV | 0.42 | 3 | 1.27 | 9.03 | 497 |
| G1TIN8 | Uncharacterized protein | CSSWPHLLREILRAARL | 0.51 | 2.5 | 1.27 | 7.83 | 498 |
| O35735 | Interferon gamma (IFN-gamma) | RKAVSELKKVMNDLL | 0.63 | 2 | 1.27 | 9.84 | 499 |
| B4LY36 | GJ24431 | GQVRNFGNACEKIVHSCKTG | 0.51 | 2.5 | 1.26 | 5.29 | 500 |

TABLE 4-continued

| | | Priority alpha core peptide sequences | | | | | |
|---|---|---|---|---|---|---|---|
| Accession # | Name | Comp Form Match | HM | Q | HM*Q | PI | SEQ ID NO: |
| Q99935 | Opiorphin prepropeptide (Basic proline-rich lacrimal protein) (Proline-rich protein 1) (PRL1) [Cleaved into: Opiorphin] | AFKSFWQKLFAIFG | 0.63 | 2 | 1.26 | 10.7 | 501 |
| P02659 | Apovitellenin-1 (Apo-VLDL-II) (Apo-II) (Apovitellenin I) (Very low density lipoprotein II) | ARLTKLAEQLMEKIKNLC | 0.63 | 2 | 1.26 | 9.21 | 502 |
| Q9YGI2 | Probable weak neurotoxin NN AMI | GKRYIRGCADTC | 0.63 | 2 | 1.26 | 8.99 | 503 |
| O49320 | Protein RALF-like 18 | NKYRRGCSAATGCYRF | 0.32 | 4 | 1.26 | 9.7 | 504 |
| Q29146 | Beta-lactoglobulin (Beta-LG) | NKGMEEFKKIVRTLT | 0.63 | 2 | 1.26 | 4.91 | 505 |
| Q9TWH3 | Venom peptide isomerase light chain | VATVKNCGKKLLAT | 0.42 | 3 | 1.26 | 9.79 | 506 |
| A1YEU0 | IL10 (Fragment) | NMLRDLRDAFSRVKTFF | 0.63 | 2 | 1.26 | 7.99 | 507 |
| Q6LBF4 | Interleukin-10 (Fragment) | NMLRDLRDAFSRVKTFF | 0.63 | 2 | 1.26 | 7.97 | 508 |
| Q9BDX4 | Interleukin-3 (IL-3) (Hematopoietic growth factor) (Mast cell growth factor) (MCGF) (Multipotential colony-stimulating factor) (P-cell-stimulating factor) | RKLKKYLEALDNFLNF | 0.63 | 2 | 1.26 | 5.45 | 509 |
| Q29FI2 | GA12182 | KHAHSMITSMLTFVSSVMN FGRSFV KD | 0.42 | 3 | 1.26 | 9.52 | 510 |
| B4H186 | GL22527 | KHAHSMITSMLTFVSSVMN FGRSFV KD | 0.42 | 3 | 1.26 | 9.52 | 511 |

TABLE 4-continued

Priority alpha core peptide sequences

| Accession # | Name | Comp Form Match | HM | Q | HM*Q | PI | SEQ ID NO: |
|---|---|---|---|---|---|---|---|
| O77559 | ADM [Cleaved into: Adrenomedullin (AM); Proadrenomedullin N-20 terminal peptide (ProAM N-terminal 20 peptide) (PAMP) (ProAM-N20)] | RAHQVLANLLKM | 0.50 | 2.5 | 1.26 | 11 | 512 |
| O97944 | Alpha-S2-casein | QKFLNKIYQYYQTFL | 0.63 | 2 | 1.25 | 5.8 | 513 |
| Q8WT56 | Fatty-acid and retinol-binding protein 1 (Ls-FAR-1) | EKFKRIANSFLQ | 0.63 | 2 | 1.25 | 8.81 | 514 |
| Q25619 | Fatty-acid and retinol-binding protein 1 (Antigen maltose-binding protein) (Ov-FAR-1) (Ov20) (OvMBP/11) (OvS1) (S1 protein) | EKFKRIANSFLQ | 0.63 | 2 | 1.25 | 8.62 | 515 |
| O43555 | Progonadoliberin-2 (Progonadoliberin II) [Cleaved into: Gonadoliberin-2 (Gonadoliberin II) (Gonadotropin-releasing hormone II) (GnRH II) (Luliberin II) (Luteinizing hormone-releasing hormone II) (LH-RH II); GnRH-associated peptide 2 (GnRH-associated peptide II)] | RHLARTLLTAARE | 0.42 | 2.5 | 1.06 | 10.8 | 516 |
| K9M1U5 | Interferon lambda-4 (IFN-lambda-4) | CARLRHVARGIADAQAVLS GL | 0.36 | 2.5 | 0.89 | 11.3 | 517 |

Figure 9:
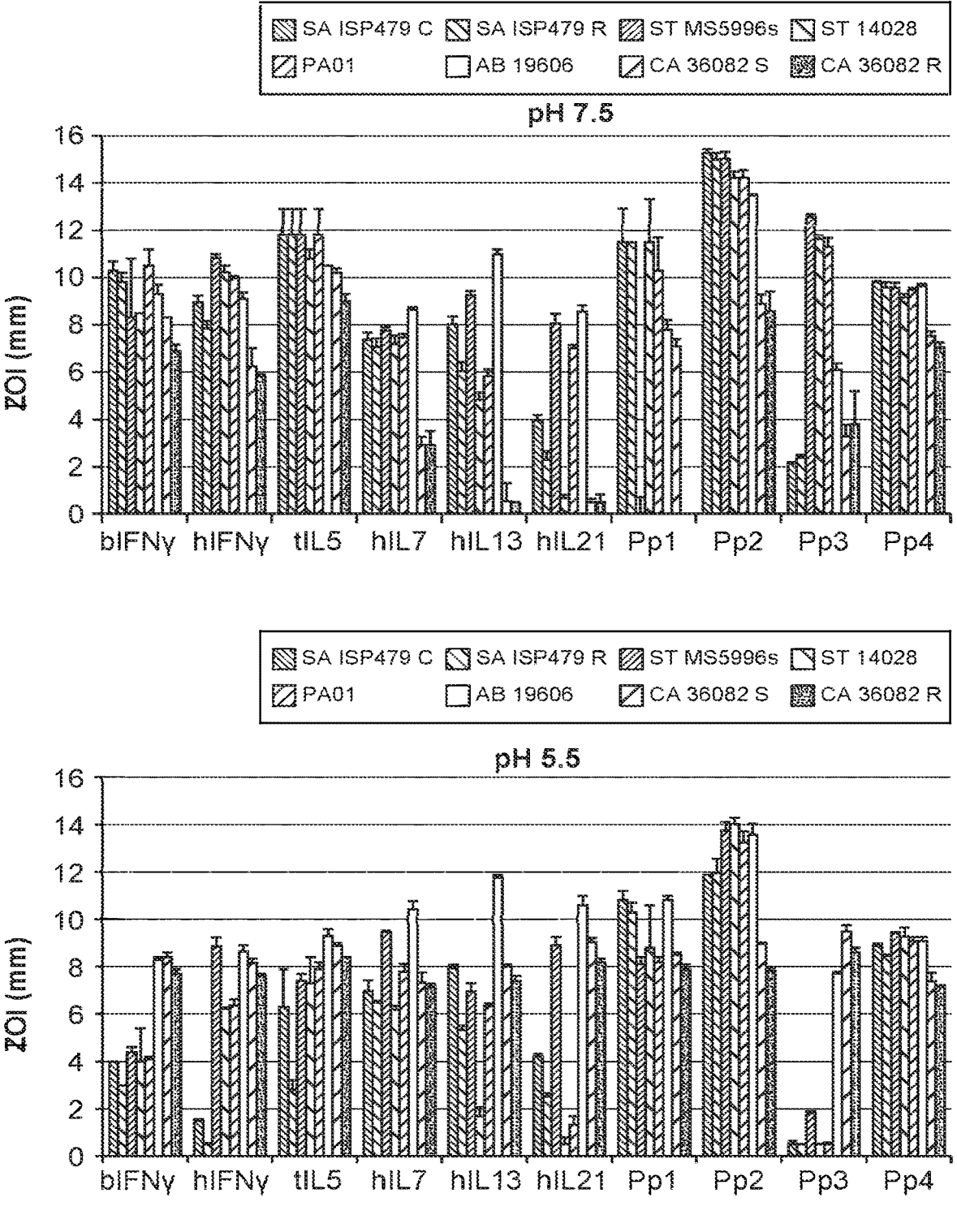
FIG. 9 shows the antimicrobial activity of study test peptides (IL-5 (SEQ ID NO:1); IL-7 (SEQ ID NO:2); IL-13 (SEQ ID NO:3); IL-21 (SEQ ID NO:4); bIFN-γ (SEQ ID NO:5); hIFN-γ (SEQ ID NO:6); Pp-1 (SEQ ID NO:7); Pp-2 (SEQ ID NO:8); Pp-3 (SEQ ID NO:9); Pp-4 (SEQ ID NO:10)). Microbicidal activity of study test peptides versus a panel of prototypic gram-positive (*S. aureus*), gram-negative (*S. typhimurium, P. aeruginosa, A. baumannii*) and fungal (*C. albicans*) pathogens at two pH's representing native physiologic (pH 7.5) or phagolysosomal (pH 5.5) environments.

When assessed against a panel of prototypic and important human pathogens, it was found that the study test peptides had potent activity against nearly all of the organisms considered (FIG. 9). In particular, of the interleukins, sequences derived from turkey IL-5 (tIL-5) were markedly potent against all organisms at pH's representative of physiologic (pH 7.5) and septic/wound (pH 5.5) environments. Sequences derived from human interleukins (hIL-7, hIL-13, hIL-21) were somewhat less potent at pH 7.5, though retained significant activity at the physiologically important pH 5.5. Likewise, the peptides derived from human and bat IFN-γ had significant activity against most organisms, being somewhat more potent at pH 7.5 than 5.5. Of the study test peptides, perhaps some of the most impressive were derived from *Phytophthora*. While Pp-1 and Pp-4 had significant activity against many organisms, Pp-2 was particularly potent against bacteria and fungi, activities that were retained at pH 5.5.

This example has utilized an alternate computational approach to screen for conserved elements common to a singular class of AHAPs as a means towards discovering universal sequence and structural elements that may confer microbicidal activity. Here, this example first identified a consensus sequence that was common to a majority of known AHAPs. This consensus was then subjected to an iterative refinement, based on alignments with both sequence and structure databases, to generate a linear formula that described an amphipathic helical span that was representative of most known AHAPs. In particular, this sequence formula consisted of a 18 residue span that included the following polar [EDKRHQNTS(AG)] and nonpolar [VMCILFWY(AG)] residues. When translated into a three dimensional radial array, this α-core formula describes an idealized amphipathic helix comprised of equivalent polar and non-polar facets (FIGS. 1A-B and 2).

One component of the iterative optimization of the α-core formula involved queries against a control AHAP dataset. These studies revealed that glycine and alanine were critical elements found within AHAP amphipathic domains, as preliminary versions of the formula lacking these residues were largely unsuccessful, retrieving fewer than 10% of control AHAP sequences. Given the inherent amphipathic frequency of the α-core formula, it was possible to assess the positional requirement for specific residues on either the polar or non-polar face of an amphipathic helix. Initial studies with glycine indicated that it was essential that this residue be included with both the polar and non-polar residue search terms, as omission from either group dramatically reduced the number of returned sequences from the control dataset. Likewise, similar studies with alanine, revealed that it was important to include this residue with both the polar and non-polar residue groups to efficiently retrieve most AHAPs from the control dataset. As the α-core formula is translated into a three dimensional helical array, these studies further indicated that alanine and glycine are likely to be found on either the polar or non-polar face of AHAP amphipathic helices.

Similar to the above sequence-based optimization studies, structure-based alignments with the PDB database were also carried out. These studies revealed that while the inclusion of proline in the formula dramatically reduced the number of retrieved helices, glycine and alanine were tolerated and were commonly found in helical spans. These studies further revealed that the α-core sequence formula retrieved helical spans with a high degree of fidelity, correctly identifying such domains more than 90% of the time. While the α-core formula was not designed as a secondary structure characterization tool, its efficiency in identifying helical spans compares favorably with such tools which correctly identify helices with frequencies ranging from xx to 81.5%.

Database Searches

Once the α-core formula was refined, it was used as a query against the SwissProt database. These studies revealed that it retrieved nearly all classes of AHAPs (94%) and approximately 89% of all known individual AHAPs with a relatively high degree of specificity. Upon examination, those individual peptides or peptide families that were not retrieved by the formula were often found to have relatively short stretches of amphipathicity or interrupted helical domains, such as the "ranabox" peptides of amphibians which are characterized as having a C-terminal helix-turn-helix domain.

It is noteworthy that while the formula describes an idealized perfectly amphipathic helix, it successfully retrieved nearly all classes, and most individual AHAPs. This suggests that nearly all AHAPs have a span of near perfect amphipathicity for at least a 12 residue span representing the size of the domain queried in these studies. Given this observation, it supports the current hypothesis that amphipathicity is a critical component of microbicidal activity and is likely essential for the membrane permeabilizing properties of AHAPs.

Residue Frequency within AHAP Helices

As the α-core sequence formula returns aligned datasets, it was possible to assess the relative frequency of various residues within AHAP α-helical spans. Moreover, these data allowed for some generalizations to be made regarding universal features common to AHAP helices. Overall, beyond the inherent amphipathicity found within AHAPs, these data revealed that several residues were strongly favored within amphipathic helices derived from various classes of organisms.

Glycine

One notable finding from these studies was that glycine is highly represented in AHAP helices from arthropods and amphibians (30-35% of all residues), whereas it occurs less frequently in mammals (15% of all residues).

Glycine in AHAP Helices of Arthropods and Amphibians

The presence of glycine within a majority of known AHAP helices would not initially be expected as this residue is known to destabilize α-helical structures. However, as was demonstrated by a large body of empirical evidence, many α-helical peptides are unstructured in aqueous environments, only to adopt an α-helical conformation in hydrophobic milieus. While the mechanism by which this occurs is not known, it is possible that peptides may become organized at the target as the relatively electronegative microbial surface may help to orient the cationic and other polar residues to one face of the amphipathic helical structure. In a similar fashion, the hydrophobic interior of the microbial plasma membrane may also help to organize the random coil structure by selectively interacting with hydrophobic residues within the peptide.

This lack of amphipathic organization prior to interaction with the target may be an important mechanism behind the selective toxicity of AHAPs that allows them to limit activity towards the host while still being able to adopt a microbicidal conformation as necessary when interacting with the target microbe.

Glycine in AHAP Helices of Higher Eukaryotes

One caveat regarding the presence of glycine in AHAP helices is that while it is common in the short peptides found within lower organisms, it occurs less frequently in the longer AHAPs of higher eukaryotes as well as in proteins with mixed domain architectures such as the chemokines, granulysin and NK lysin. If the supposition that glycine is an important means to keep AHAPs in an unstructured and inactive state prior to interaction with their microbial target, the lack of glycine in these larger peptides suggests that they may use an alternate means of microbicidal dampening to limit toxicity towards the host.

Cationic Residues in AHAP Helices of Arthropods and Amphibians

Beyond demonstrating an abundance of glycine in AHAP helices, residue frequency studies also revealed that lysine is highly favored over arginine in the amphipathic helices of the AHAPs considered in this study. Lysine was the most abundant cationic residue in study AHAP helices, where it was strongly preferred over arginine in non-mammalian peptides at a 12:1 ratio. In mammals, lysine was still preferred over arginine, but to a lesser extent with a 3:1 ratio. By comparison, lysine was less abundant in toxins where it was preferred over arginine at a 2:1 ratio.

It may be of some relevance that biophysical measures have demonstrated lysine is less efficient at generating membrane destabilizing NGC than arginine, as it can only interact with a single lipid head group at a time. Because of this, AHAPs that are rich in lysine often compensate for this lack of permeabilizing ability by having an increased mean hydrophobicity, in what has been termed the 'saddle-splay curvature selection' rule. In the current study, AHAP helices largely support this rule with the finding that, as the relative abundance of lysine is increased ($N_K/N_K+N_R$), mean peptide hydrophobicity is also increased.

Biophysical Properties of AHAP Helices as Compared with Other α-Helical Domains

Beyond measurements of residue frequency, a number of additional properties of helices retrieved by the α-core formula were determined including: Q, µH, H. When averaged across families, these quantitative data revealed a number of insights regarding the biophysical properties of retrieved AHAP helices versus those of toxins and other groups.

One defining characteristic of AHAPs is that they are typically cationic in nature, a property that has been shown to enhance their selectivity towards the relatively electronegative surface of many microorganisms. The universality of this biophysical property is supported by findings from the current study, where amphipathic helices derived from AHAPs had an average net charge of +2.0 over a twelve residue span. Moreover, if only cationic AHAPs are considered (Q≥0.5 for 707 of 803 retrieved sequences), this value rises to +2.7. By comparison the average charge for toxin and other helices retrieved in these studies was +1.3 and +0.6 respectively, suggesting that cationicity may be selectively favored in AHAPs as compared with other amphipathic peptides.

Another characteristic feature of AHAPs is that they are frequently amphipathic in nature, a property that has been deemed essential for their membrane permeabilizing activities towards microbes. As the α-core formula searches for amphipathic sequences, all of the helices returned by these queries were a priori amphipathic in nature. However, it was still of interest to compare the relative amphipathicity, as quantitated by µH, of identified helices between various classes of peptides. Results from the current study support the theory that amphipathicity is an essential biophysical property of AHAPs as the average hydrophobic moment for study AHAP helices was 0.52, a relatively high value when compared to archetypal amphipathic helices such as cecropin A ($\mu H_{max}$=0.61) or LL-37 ($\mu H_{max}$=0.78). In comparison, the amphipathicity of helices derived from toxins and other proteins were somewhat lower at µH=0.42 and 0.39 respectively.

In addition, mean hydrophobicity (H) was somewhat greater for AHAPs (0.42) than for toxins (0.34) or other study peptides (0.39). This observation suggests that a moderate level of hydrophobicity may be essential for the membrane permeabilizing properties of AHAPs.

Identify New Antimicrobial Sequences

The α-core sequence formula also retrieved a large number of uncharacterized sequences as well as proteins with an alternate primary function. Given the fidelity of retrieving antimicrobial sequences, it was of interest to determine whether some of these alternate sequences might also possess antimicrobial properties. As described, putative microbicidal sequences were scored for properties that were most discriminative at separating AHAPs from other sequences (µH*Q or µH*PI) and lead candidates of biological interest were synthesized for further study.

Representative peptide helices from three separate high-scoring groups, interleukins (tIL-5, hIL-7, hIL-13 and hIL-21), interferons (bIFN-γ, hIFN-γ) and uncharacterized sequences from *P. parasitica* were synthesized and tested for their microbicidal activity. Notably, all of these peptides displayed potent microbicidal activity, which in many cases was greater than that of classic AHAPs such as LL-37. These data strongly suggest that the amphipathic sequence formula can successfully identify amphipathic helices with antimicrobial properties.

Unless otherwise defined, all technical and scientific terms used herein have the same meaning as commonly understood by one of ordinary skill in the art to which this disclosure belongs.

The disclosures illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the disclosure claimed.

Thus, it should be understood that although the present disclosure has been specifically disclosed by preferred embodiments and optional features, modification, improvement and variation of the disclosures embodied therein herein disclosed may be resorted to by those skilled in the art, and that such modifications, improvements and variations are considered to be within the scope of this disclosure. The materials, methods, and examples provided here are representative of preferred embodiments, are exemplary, and are not intended as limitations on the scope of the disclosure.

The disclosure has been described broadly and generically herein. Each of the narrower species and subgeneric groupings falling within the generic disclosure also form part of the disclosure. This includes the generic description of the disclosure with a proviso or negative limitation removing any subject matter from the genus, regardless of whether or not the excised material is specifically recited herein.

In addition, where features or aspects of the disclosure are described in terms of Markush groups, those skilled in the art will recognize that the disclosure is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

It is to be understood that while the disclosure has been described in conjunction with the above embodiments, that the foregoing description and examples are intended to illustrate and not limit the scope of the disclosure. Other aspects, advantages and modifications within the scope of the disclosure will be apparent to those skilled in the art to which the disclosure pertains.

---

SEQUENCE LISTING

The patent contains a lengthy sequence listing. A copy of the sequence listing is available in electronic form from the USPTO web site (https://seqdata.uspto.gov/docdetail?docId=US12590131B2). An electronic copy of the sequence listing will also be available from the USPTO upon request and payment of the fee set forth in 37 CFR 1.19(b)(3).

---

The invention claimed is:

1. A method for treating an infection in a patient in need thereof, comprising administering to the patient a peptide comprising the amino acid sequence of SEQ ID NO:1, wherein the peptide is not longer than 60 amino acid residues in length.

2. The method of claim 1, wherein the peptide is not longer than 50 amino acid residues in length.

3. The method of claim 1, further comprising administering to the patient an antimicrobial agent.

4. The method of claim 3, wherein the antimicrobial agent is selected from the group consisting of imipenem, ceftazidime, colistin, chloroquine, artemisinin, vancomycin and daptomycin.

5. The method of claim 1, wherein the infection is caused by a Gram-negative bacterium, a Gram-positive bacterium or a fungus.

6. The method of claim 1, wherein the administration is subcutaneous, intravenous, intramuscular, intra-articular, intra-synovial, intrasternal, intrathecal, intrahepatic, intralesional, or intracranial injection, or infusion.

7. The method of claim 1, wherein the patient is a mammal.

8. The method of claim 7, wherein the patient is a human.

* * * * *